United States Patent
Matray et al.

(10) Patent No.: US 12,018,159 B2
(45) Date of Patent: Jun. 25, 2024

(54) ULTRA BRIGHT DIMERIC OR POLYMERIC DYES AND METHODS FOR PREPARATION OF THE SAME

(71) Applicant: SONY GROUP CORPORATION, Tokyo (JP)

(72) Inventors: Tracy Matray, Snohomish, WA (US); Michael VanBrunt, Covington, WA (US)

(73) Assignee: SONY GROUP CORPORATION, Tokyo (JP)

( * ) Notice: Subject to any disclaimer, the term of this patent is extended or adjusted under 35 U.S.C. 154(b) by 1092 days.

(21) Appl. No.: 16/321,764

(22) PCT Filed: Jul. 27, 2017

(86) PCT No.: PCT/US2017/044233
§ 371 (c)(1),
(2) Date: Jan. 29, 2019

(87) PCT Pub. No.: WO2018/022925
PCT Pub. Date: Feb. 1, 2018

(65) Prior Publication Data
US 2019/0177549 A1    Jun. 13, 2019

Related U.S. Application Data

(60) Provisional application No. 62/368,819, filed on Jul. 29, 2016.

(51) Int. Cl.
| C09B 69/10 | (2006.01) |
| G01N 1/30 | (2006.01) |
| G01N 33/58 | (2006.01) |

(52) U.S. Cl.
CPC ............ *C09B 69/109* (2013.01); *C09B 69/10* (2013.01); *C09B 69/106* (2013.01); *G01N 1/30* (2013.01); *G01N 33/582* (2013.01); *G01N 33/583* (2013.01); *G01N 2001/302* (2013.01)

(58) Field of Classification Search
CPC ........ C09B 69/10; C09B 69/109; G01N 1/30; G01N 2001/30; G01N 33/58
See application file for complete search history.

(56) References Cited

U.S. PATENT DOCUMENTS

| 4,450,305 A | 5/1984 | Kamhi |
| 4,476,229 A | 10/1984 | Fino et al. |
| 4,778,753 A | 10/1988 | Yamanishi et al. |
| 5,053,054 A | 10/1991 | Kirchanski |
| 5,268,486 A | 12/1993 | Waggoner et al. |
| 5,318,894 A | 6/1994 | Pugia |
| 5,582,977 A | 12/1996 | Yue et al. |
| 5,698,391 A | 12/1997 | Cook et al. |
| 5,886,177 A | 3/1999 | Cook et al. |
| 5,994,143 A | 11/1999 | Bieniarz et al. |
| 6,005,093 A | 12/1999 | Wood et al. |
| 6,140,480 A | 10/2000 | Kool |
| 6,171,859 B1 | 1/2001 | Herrnstadt et al. |
| 6,218,108 B1 | 4/2001 | Kool |
| 6,365,730 B1 | 4/2002 | Jennings et al. |
| 6,380,431 B1 | 4/2002 | Whipple et al. |
| 6,479,650 B1 | 11/2002 | Kool |
| 6,514,700 B1 | 2/2003 | Singh |
| 6,534,041 B1 | 3/2003 | Licha et al. |
| 6,627,400 B1 | 9/2003 | Singh et al. |
| 6,670,193 B2 | 12/2003 | Kool |
| 6,716,452 B1 | 4/2004 | Piccariello et al. |
| 6,852,709 B2 | 2/2005 | Leong et al. |
| 7,038,063 B2 | 5/2006 | Lee et al. |
| 7,060,708 B2 | 6/2006 | Piccariello et al. |
| 7,172,907 B2 | 2/2007 | Chen et al. |
| 7,423,133 B2 | 9/2008 | Kool et al. |
| 7,667,024 B2 | 2/2010 | Mao et al. |
| 7,897,684 B2 | 3/2011 | Bazan et al. |
| 8,008,522 B2 | 8/2011 | Luktanov et al. |
| 8,101,776 B2 | 1/2012 | Berens et al. |
| 8,153,706 B2 | 4/2012 | Vasudevan |
| 8,217,389 B2 | 7/2012 | Nakano et al. |
| 8,293,700 B2 | 10/2012 | Arranz |
| 8,349,308 B2 | 1/2013 | Yurkovetskiy et al. |
| 8,354,515 B2 | 1/2013 | Ueno et al. |
| 8,431,545 B2 | 4/2013 | Kataoka et al. |
| 8,491,993 B2 | 7/2013 | Nguyen et al. |
| 8,546,590 B2 | 10/2013 | Gall |
| 8,632,947 B2 | 1/2014 | Bentley et al. |
| 8,802,738 B2 | 8/2014 | Emrick |
| 8,895,023 B2 | 11/2014 | Rademacher et al. |
| 8,906,603 B2 | 12/2014 | Castro et al. |
| 8,946,394 B2 | 2/2015 | Na et al. |

(Continued)

FOREIGN PATENT DOCUMENTS

| CA | 2263671 A1 | 2/1998 |
| CN | 102174078 A | 9/2011 |

(Continued)

OTHER PUBLICATIONS

"What is an Analyte?, Google Search, dated Mar. 22, 2018, retrieved from https://www.google.com/search?q=what+is+an+analyte&rlz=ICIGCEB_enUS775US775&oq=what+is+an+analyte&aqs=chrome..69i57j015.32311j0j7&s . . . " 2 pages.

Arian et al., "1,9-Dialkoxyanthracene as a $^1O_2$-Sensitive Linker," *J. Am. Chem. Soc.* 133:3972-3980, 2011.

Babitskaya et al., "Bromoacyl Analogues of Phosphatidylcholine with Intramolecular Fluorescence Quenching and Their Use as Substrates for Continuous Monitoring of Phospholipase $A_2$ Activity," *Applied Biochemistry and Microbiology* 40(4):351-356, 2004.

(Continued)

*Primary Examiner* — Theodore R. Howell
(74) *Attorney, Agent, or Firm* — Seed IP Law Group LLP

(57) ABSTRACT

Dimeric and/or polymeric dyes and compounds and methods for preparation of the same are disclosed.

18 Claims, No Drawings

(56) References Cited

U.S. PATENT DOCUMENTS

| | | |
|---|---|---|
| 9,029,537 B2 | 5/2015 | Koch |
| 9,085,799 B2 | 7/2015 | Bazan et al. |
| 9,150,782 B2 | 10/2015 | Lee et al. |
| 9,400,273 B1 | 7/2016 | Liu et al. |
| 9,545,447 B2 | 1/2017 | Wooley et al. |
| 9,649,389 B2 | 5/2017 | Groves et al. |
| 9,687,291 B2 | 6/2017 | Shimizu et al. |
| 9,689,877 B2 | 6/2017 | Matray et al. |
| 9,696,310 B2 | 7/2017 | Margulies et al. |
| 9,714,946 B2 | 7/2017 | Bradner et al. |
| 9,765,220 B2 | 9/2017 | Matray et al. |
| 9,822,134 B2 | 11/2017 | Segev |
| 9,851,359 B2 | 12/2017 | Matray et al. |
| 9,884,070 B2 | 2/2018 | Denardo et al. |
| 9,910,051 B2 | 3/2018 | Beacham et al. |
| 9,913,992 B2 | 3/2018 | Demarest et al. |
| 9,932,578 B2 | 4/2018 | Feinstein et al. |
| 9,939,454 B2 | 4/2018 | Dzubay et al. |
| 10,036,754 B2 | 7/2018 | Matray et al. |
| 10,191,060 B2 | 1/2019 | Chiu et al. |
| 10,435,563 B2 | 10/2019 | Matray et al. |
| 10,617,670 B2 | 4/2020 | Sapra et al. |
| 10,709,791 B2 | 7/2020 | Stayton et al. |
| 10,834,091 B2 | 11/2020 | Deninno et al. |
| 10,865,310 B2 | 12/2020 | Matray et al. |
| 10,866,244 B2 | 12/2020 | Matray et al. |
| 10,954,391 B2 | 3/2021 | Matray et al. |
| 10,989,715 B2 | 4/2021 | Matray et al. |
| 11,013,756 B2 | 5/2021 | Haruta et al. |
| 11,084,932 B2 | 8/2021 | Battrell et al. |
| 11,142,647 B2 | 10/2021 | Matray et al. |
| 11,312,736 B1 | 4/2022 | Matray et al. |
| 11,352,502 B2 | 6/2022 | Matray et al. |
| 11,370,922 B2 | 6/2022 | Matray et al. |
| 11,377,563 B2 | 7/2022 | Matray et al. |
| 11,390,754 B2 | 7/2022 | Singh et al. |
| 11,434,374 B2 | 9/2022 | Matray et al. |
| 11,434,377 B2 | 9/2022 | Matray et al. |
| 11,453,783 B2 | 9/2022 | Matray et al. |
| 11,685,835 B2 | 6/2023 | Matray |
| 11,874,280 B2 | 1/2024 | Jackson et al. |
| 2001/0018503 A1 | 8/2001 | Whipple et al. |
| 2002/0012947 A1 | 1/2002 | Bevers et al. |
| 2002/0099013 A1 | 7/2002 | Piccariello et al. |
| 2002/0142329 A1 | 10/2002 | Matray et al. |
| 2003/0054361 A1 | 3/2003 | Heller |
| 2003/0207208 A1 | 11/2003 | Uenishi |
| 2003/0207264 A1 | 11/2003 | Packard et al. |
| 2004/0014981 A1 | 1/2004 | Lugade et al. |
| 2004/0067498 A1 | 4/2004 | Chenna et al. |
| 2004/0096825 A1 | 5/2004 | Chenna et al. |
| 2004/0138467 A1 | 7/2004 | French et al. |
| 2004/0224372 A1 | 11/2004 | Li et al. |
| 2004/0241768 A1 | 12/2004 | Whitten et al. |
| 2005/0054024 A1 | 3/2005 | Lawrence |
| 2005/0123935 A1 | 6/2005 | Haugland et al. |
| 2006/0008822 A1 | 1/2006 | Manoharan et al. |
| 2006/0035302 A1 | 2/2006 | Lee |
| 2006/0063186 A1 | 3/2006 | Benson et al. |
| 2007/0042398 A1 | 2/2007 | Peng et al. |
| 2007/0077549 A1 | 4/2007 | Buller et al. |
| 2007/0148094 A1 | 6/2007 | Uzgiris |
| 2007/0269902 A1 | 11/2007 | Beechem et al. |
| 2008/0227939 A1 | 9/2008 | Mizoshita et al. |
| 2009/0253792 A1 | 10/2009 | Mickle et al. |
| 2009/0299070 A1 | 12/2009 | Berens et al. |
| 2010/0039684 A1 | 2/2010 | Kolb et al. |
| 2010/0092386 A1 | 4/2010 | Segev |
| 2010/0129800 A1 | 5/2010 | Aymami Bofarull et al. |
| 2010/0192312 A1 | 8/2010 | Cremer et al. |
| 2011/0224516 A1 | 9/2011 | Romey et al. |
| 2012/0021454 A1 | 1/2012 | Bikker et al. |
| 2012/0116079 A1 | 5/2012 | Lukhtanov et al. |
| 2013/0059343 A1 | 3/2013 | Cheung |
| 2013/0102021 A1 | 4/2013 | Beacham et al. |
| 2013/0119363 A1 | 5/2013 | Sasaki et al. |
| 2013/0137755 A1 | 5/2013 | Segev |
| 2013/0202536 A1 | 8/2013 | Mustaev et al. |
| 2013/0244891 A1 | 9/2013 | Waggoner et al. |
| 2014/0023590 A1 | 1/2014 | Gao et al. |
| 2014/0193504 A1 | 7/2014 | Wooley et al. |
| 2014/0275508 A1 | 9/2014 | Scarr et al. |
| 2015/0030541 A1 | 1/2015 | Rogers |
| 2015/0110715 A1 | 4/2015 | Eder et al. |
| 2015/0159198 A1 | 6/2015 | McGall et al. |
| 2015/0232615 A1 | 8/2015 | Kwiatkowski |
| 2015/0258217 A1 | 9/2015 | Caravan |
| 2016/0039850 A1 | 2/2016 | Segev |
| 2016/0176903 A1 | 6/2016 | Segev |
| 2016/0264737 A1 | 9/2016 | Bartholomew et al. |
| 2016/0327859 A1 | 11/2016 | Idei et al. |
| 2016/0347907 A1 | 12/2016 | Dose |
| 2017/0326233 A1 | 11/2017 | Demeule et al. |
| 2018/0065998 A1 | 3/2018 | Battrell et al. |
| 2018/0079909 A1 | 3/2018 | Matray et al. |
| 2018/0092993 A1 | 4/2018 | Desai et al. |
| 2018/0141935 A1 | 5/2018 | Josel et al. |
| 2018/0163052 A1 | 6/2018 | Matray et al. |
| 2018/0164322 A1 | 6/2018 | Matray et al. |
| 2018/0237641 A1 | 8/2018 | Matray et al. |
| 2018/0312468 A1 | 11/2018 | Zhang et al. |
| 2019/0016898 A1 | 1/2019 | Matray et al. |
| 2019/0136065 A1 | 5/2019 | Singh et al. |
| 2019/0144678 A1 | 5/2019 | Matray et al. |
| 2019/0153232 A1 | 5/2019 | Matray et al. |
| 2019/0300716 A1 | 10/2019 | Matray et al. |
| 2020/0032139 A1 | 1/2020 | Behrendt et al. |
| 2020/0109287 A1 | 4/2020 | Matray et al. |
| 2020/0164085 A1 | 5/2020 | Brandish et al. |
| 2020/0222554 A1 | 7/2020 | Matray et al. |
| 2020/0284798 A1 | 9/2020 | Matray et al. |
| 2020/0330610 A1 | 10/2020 | Desai et al. |
| 2020/0353089 A1 | 11/2020 | Matray |
| 2020/0353094 A1 | 11/2020 | Matray |
| 2020/0360526 A1 | 11/2020 | Matray |
| 2020/0392345 A1 | 12/2020 | Matray et al. |
| 2021/0032277 A1 | 2/2021 | Matray et al. |
| 2021/0032474 A1 | 2/2021 | Matray et al. |
| 2021/0095130 A1 | 4/2021 | Matray et al. |
| 2021/0096135 A1 | 4/2021 | Matray et al. |
| 2021/0109104 A1 | 4/2021 | Jackson et al. |
| 2021/0128591 A1 | 5/2021 | Matray |
| 2021/0128739 A1 | 5/2021 | Matray |
| 2021/0139440 A1 | 5/2021 | Ramsden et al. |
| 2021/0253864 A1 | 8/2021 | Matray et al. |
| 2021/0261782 A1 | 8/2021 | Matray et al. |
| 2021/0285953 A1 | 9/2021 | Matray et al. |
| 2021/0340380 A1 | 11/2021 | Matray et al. |
| 2021/0395530 A1 | 12/2021 | Matray et al. |
| 2022/0160887 A1 | 5/2022 | Matray et al. |
| 2022/0168433 A1 | 6/2022 | Matray et al. |
| 2022/0168435 A1 | 6/2022 | Matray et al. |
| 2022/0175951 A1 | 6/2022 | Boitano et al. |
| 2022/0220314 A1 | 7/2022 | Singh et al. |
| 2022/0227794 A1 | 7/2022 | Matray et al. |
| 2022/0305127 A1 | 9/2022 | Thomas et al. |
| 2022/0372297 A1 | 11/2022 | Matray et al. |
| 2022/0380603 A1 | 12/2022 | Matray et al. |
| 2022/0402963 A1 | 12/2022 | Matray et al. |
| 2023/0012304 A1 | 1/2023 | Matray et al. |
| 2023/0129481 A1 | 4/2023 | Matray et al. |

FOREIGN PATENT DOCUMENTS

| | | |
|---|---|---|
| CN | 103319378 A | 9/2013 |
| CN | 104072727 A | 10/2014 |
| CN | 106589005 A | 4/2017 |
| GB | 2 372 256 A | 8/2002 |
| GB | 2 554 666 A | 4/2018 |
| JP | S61-207395 A | 9/1986 |
| JP | S61207395 A | 9/1986 |
| JP | 4-282391 A | 10/1992 |
| JP | 2000-17183 A | 1/2000 |
| JP | 2016534107 A | 11/2016 |

(56) References Cited

FOREIGN PATENT DOCUMENTS

| | | |
|---|---|---|
| JP | 2017504659 A | 2/2017 |
| JP | 2017124994 A | 7/2017 |
| KR | 10-1041446 B1 | 6/2011 |
| KR | 101041446 B1 | 6/2011 |
| KR | 10-2015-0007795 A | 1/2015 |
| SU | 1121931 A | 4/1988 |
| SU | 1121931 A1 | 4/1988 |
| WO | 95/02700 A1 | 1/1995 |
| WO | WO 9506731 A2 | 3/1995 |
| WO | 98/07449 A2 | 2/1998 |
| WO | WO 9807449 A2 | 2/1998 |
| WO | WO 9832463 A2 | 7/1998 |
| WO | 01/73123 A2 | 10/2001 |
| WO | WO 0173123 A2 | 10/2001 |
| WO | 02/22883 A1 | 3/2002 |
| WO | 02/083954 A1 | 10/2002 |
| WO | 2004/007751 A2 | 1/2004 |
| WO | WO 2007094135 A1 | 8/2007 |
| WO | 2010/026957 A1 | 3/2010 |
| WO | 2013/012687 A2 | 1/2013 |
| WO | 2014/147642 A1 | 9/2014 |
| WO | WO-2015027176 A1 | 2/2015 |
| WO | WO 2015091953 A1 | 6/2015 |
| WO | WO-2015109136 A2 | 7/2015 |
| WO | WO 2015155753 A2 | 10/2015 |
| WO | 2017/003639 A2 | 1/2017 |
| WO | WO 2017062271 A1 | 4/2017 |
| WO | 2017/089890 A1 | 6/2017 |
| WO | WO 2017089890 A1 | 6/2017 |
| WO | 2017/173348 A1 | 10/2017 |
| WO | 2017/177065 A2 | 10/2017 |
| WO | 2018/060722 A1 | 4/2018 |
| WO | 2019/071208 A1 | 4/2019 |
| WO | WO 2019126691 A1 | 6/2019 |
| WO | WO 2019182765 A1 | 9/2019 |
| WO | WO 2020219959 A1 | 10/2020 |

OTHER PUBLICATIONS

Becker et al., "New Thermotropic Dyes on Amino-Substituted Perylendicarboximides," *Chem. Eur. J.* 6(21):3984-3990, 2000.
Bergstrom et al., "A NaPi2b Antibody-Drug Conjugate Induces Durable Complete Tumor Regressions in Patient-Derived Xenograft Models of Nsclc," *IASLC 17th World Conference on Lung Cancer*, Vienna, Austria, Dec. 4-7, 2016. (8 pages).
Bergstrom et al., "A novel, highly potent HER2-targeted antibody-drug conjugate (ADC) for the treatment of low HER2-expressing tumors and combination with trastuzumab-based regimens in HER2-driven tumors," Mersana Therapeutics, Abstract LBA-231, 2015, 1 page.
Bergstrom et al., "Potent Promise," *Innovations in Pharmaceutical Technology* 49:16-20, 2014.
Bergstrom et al., "XMT-1522 induces tumor regressions in preclinical models representing HER2-positive and HER2 low-expressing breast cancer," Mersana Therapeutics, Abstract P4-14-28, 2015, 1 page.
Braeckmans et al., "Three-dimensional fluorescence recovery after photobleaching with the confocal scanning laser microscope," *Biophysical Journal* 85:2240-2252, 2003.
Braga et al., "Intracellular macromolecular mobility measured by fluorescence recovery after photobleaching with confocal laser scanning microscopes," *Molecular Biology of the Cell* 15:4749-4760, 2004.
Brinkley, "A brief survey of methods for preparing protein conjugates with dyes, haptens and crosslinking reagents," *Bioconjugate Chem* 3:2-13, 1992.
CAPLUS Accession No. 1975: 171341, Holy, "Nucleic acid components and their analogs. CLXXII. Aliphatic analogs of nucleosides, nucleotides, and oligonucleotides," Collection of Czechoslovak Chemical Communications 40(1):187-214, 1975. (1 page).
Chong et al., "Oxygen Quenching of Pyrene-Lipid Fluorescence in Phosphatidylcholine Vesicles—A Probe for Membrane Organization," *Biophys. J.* 47:613-621, 1985.
Dai et al., "DNA-polyfluorophore excimers as sensitive reporters for esterases and lipases," *Chemical Communications* 46:1221-1223, 2010.
DiVittorio et al., "Synthetic peptides with selective affinity for apoptotic cells," *Organic & Biomolecular Chemistry* 4:1966-1976, 2006.
Gao et al., "Libraries of Composite Polyfluors Built from Fluorescent Deoxyribosides," *Jorunal of the American Chemical Society* 124:11590-11591, 2002.
Gao et al., "Modified DNA Analogues That Sense Light Exposure with Color Changes," *Journal of the American Chemical Society* 126:12748-12749, 2004.
Gordon et al., "Analysis of simulated and experimental fluorescence recovery after photobleaching. Data for two diffusing components," *Biophysical Journal* 68:766-778, 1995.
Hanhela et al., "Synthesis and Evaluation of Fluorescent Materials for Colour Control of Peroxyoxalate Chemiluminescence. III. Yellow and Red Fluorescent Emitters," *Australian Journal of Chemistry* 34:1701-1717, 1981.
Haraguchi, "Live Cell Imaging: Approaches for Studying Protein Dynamics in Living Cells," *Cell Structure And Function* 27:333-334, 2002.
Koo et al., "Fluorescent DNA chemosensors: identification of bacterial species by their volatile metabolites," *Chemical Communications* 47:11435-11437, 2011.
Lee et al., "Monitoring the Hydrophobic Interactions of Internally Pyrene-Labeled Poly(ethylene oxide)s in Water by Fluorescence Spectroscopy," *Macromolecules* 31:9193-9200, 1998.
Liu et al., "Detection of prostate-specific membrane antigen on HUVECs in response to breast tumor-conditioned medium," *International Journal of Oncology* 38:1349-1355, 2011.
Liu et al., "DNA-Based Micelles: Synthesis, Micellar Properties and Size-Dependent Cell Permeability," *Chem. Eur. J.* 16:3791-3797, 2010. (14 Pages).
Mersana Therapeutics, URL= http://www.mersana.com, download date Jan. 3, 2019, 9 pages.
Molotkovsky et al., "Perylenoyl- and Anthrylvinyl-Labeled Lipids as Membrane Probes," *Biochimica et Biophysica Acta* 778:281-288, 1984.
Nussbaumer et al., "Amplification of Chirality by Supramolecular Polymerization of Pyrene Oligomers," *Angewandte Chemie International Edition* 50:5490-5494, 2011.
Pownall et al., "Kinetics of Spontaneous and Plasma-Stimulated Sphingomyelin Transfer," *Biochimica et Biophysica Acta* 712:169-176, 1982.
PubChem, "US20100012929A1-20100121-C00010_4," SID No. 140452858, retrieved Mar. 29, 2016 from URL https://pubchem.ncbi.nlm.nih.gov/substance/140452858, 6 pages.
Wang et al., "Cruciforms: Assembling Single Crystal Micro- and Nanostructures from One to Three Dimensions and Their Applications in Organic Field-Effect Transistors," *Chem. Mater.* 21:2840-2845, 2009.
Wang et al., "DNA Polyfluorophores for Real-Time Multicolor Tracking of Dynamic Biological Systems," *Angew. Chem. Int. Ed.* 51:7176-7180, 2012.
Wilson et al., "Efficient Quenching of Oligomeric Fluorophores on a DNA Backbone," *Journal of the American Chemical Society* 129(50):15426-15427, 2007.
Wilson et al., "Oligodeoxyfluorosides: Strong Sequence of Dependence of Fluorescence Emission," *Tetrahedron* 63(17):3427-3433, 2007. (18 Pages).
Yurkovetskiy et al., "Advantages of Polyacetal Polymer-based Antibody Drug Conjugates: Application to Low Expression Targets," Mersana Therapeutics, technical paper #2645, 2014, 1 page.
Buckhout-White et al., "Assembling programmable FRET-based photonic networks using designer DNA scaffolds," *Nature Communications* 5:5615, Dec. 11, 2014. (16 pages).
Doi et al., "Hetero-Selective DNA-Like Duplex Stabilized by Donor-Acceptor Interactions," *Chem. Eur. J.* 21:15974-15980, 2015.
Franceschin et al., "Synthesis of a Dibromoperylene Phosphoramidite Building Block and Its Incorporation at the 5' End of a G-Quadruplex

(56) References Cited

OTHER PUBLICATIONS

Forming Oligonucleotide: Spectroscopic Properties and Structural Studies of the Resulting Dibromoperylene Conjugate," *Bioconjugate Chem* 22:1309-1319, 2011.
Johansson, "Choosing Reporter-Quencher Pairs for Efficient Quenching Through Formation of Intramolecular Dimers," *Methods in Molecular Biology* 335:17-29, 2006.
Masuko et al., "Fluorescence resonance energy transfer from pyrene to perylene labels for nucleic acid hybridization assays under homogenous solution conditions," *Nucleic Acids Research* 28(8):e34, 2000 (8 pages).
Saito et al., "Dual-labeled oligonucleotide probe for sensing adenosine via FRET: A novel alternative to SNPs genotyping," *Chem. Commun.*:2133-2135, 2007.
Takakusa et al., "Design and Synthesis of an Enzyme-Cleavable Sensor Molecule for Phosphodiesterase Activity Based on Fluorescence Resonance Energy Transfer," *J. Am. Chem. Soc.* 124(8):1653-1657, 2002.
Vinogradov et al., "Total synthesis and biochemical characterization of mirror image barnase," *Chem Sci.* 6: 2997-3002, 2015.
Beaucage et al., "The Functionalization of Oligonucleotides Via Phosphoramidite Derivatives," *Tetrahedron* 49(10):1925-1963, 1993.
Chattopadhyay et al., "Brilliant Violet Fluorophores: A New Class of Ultrabright Fluorescent Compounds for Immunofluorescence Experiments," *Cytometry Part A* 81A:456-466, 2012.
Cuppoletti et al., "Oligomeric fluorescent labels for DNA," *Bioconjug. Chem.* 16(3):528-534, 2005.
Dioubankova et al., "Oligonucleotides containing new fluorescent 1-phenylethynylpyrene and 9,10-bis(phenylethynyl)anthracene uridine-2'-carbamates: synthesis and properties," *Tetrahedron* 60:4617-4626, 2004.
Dubrovsky, "Semiconductor nanoparticles as reporters in multiplexed immunoassay and cell analysis," *International Journal of Nanoscience* 8(1 & 2):163-167, 2009.
Jain et al. "Current ADC Linker Chemistry," *Pharm. Res.* 32:3526-3540, 2015.
Kozma et al., "Fluorescent Ligands for Adenosine Receptors," *Bioorganic & Medicinal Chemistry Letters* 23: 26-36, 2013.
Leung et al., "7-Amino-4-Methyl-6-Sulfocoumarin-3-Acetic Acid: A Novel Blue Fluorescent Dye for Protein Labeling," *Bioorganic & Medicinal Chemistry Letters* 9: 2229-2232, 1999.
Li et al., "Polymeric Drugs: Advances in the development of pharmacologically active polymers," *Journal of Controlled Release* 219:360-382, 2015.
Luo et al., "Sensitive and rapid quantification of C-reactive protein using quantum dot-labeled microplate immunoassay," *Journal of Translational Medicine* 10(24):1-9, 2012.
Malakhov et al., "1-(Phenylethynyl)pyrene and 9,10-Bis(phenylethynyl)anthracene, Useful Fluorescent Dyes for DNA Labeling: Excimer Formation and Energy Transfer," *Eur. J. Org. Chem*: 1298-1307, 2004.
Paris et al., "Probing DNA sequences in solution with a monomer-excimer fluorescence color change," *Nucleic Acids Research* 26(16):3789-3793, 1998.
Petreus et al., "Polyester imides containing main-chain phosphorus," *Revue Roumaine de Chimie* 34(8):971-978, 1994 (with English Abstract).
Ren et al., "An Antisense Oligodeoxynucleotide-Doxorubicin Conjugate: Preparation and Its Reversal Multidrug Resistance of Human Carcinoma Cell Line In Vitro," *Nucleosides, Nucleotides & Nucleic Acids* 23(10):1595-1607, 2004.
RN 230952-79-1, Registry Database Compound, 1999.
Singh et al., "Multiplexed measurement of membrane protein populations," *Caplus* 2003:769075, 2003. (2 pages).
Stuart et al., "Site-Specific DNA-Doxorubicin Conjugates Display Enhanced Cytotoxicity to Breast Cancer Cells," *Bioconjugate Chemistry* 25:406-413, 2014.

Teo et al., "Polyfluorophores on a DNA Backbone: A Multicolor Set of Labels Excited at One Wavelength," *J. Am. Chem. Soc.* 131(11):3923-3933, 2009. (NIH Public Access Author Manuscript, available in PMC Mar. 25, 2010, 23 pages).
Tram et al., "Oligonucleotide Labeling Using BODIPY Phosphoramidite," *Nucleosides, Nucleotides & Nucleic Acids* 30(1):1-11, 2011.
U.S. Appl. No. 17/735,947, filed May 3, 2022.
U.S. Appl. No. 17/869,366, filed Jul. 20, 2022.
U.S. Appl. No. 17/764,874, filed Mar. 29, 2022.
U.S. Appl. No. 17/891,807, filed Aug. 19, 2022.
Avirah et al., "Infrared Absorbing Croconaine Dyes: Synthesis and Metal Ion Binding Properties," *J. Org. Chem.* 73(1):274-279, 2008.
Li et al., "Responsive nanogel-based dual fluorescent sensors for temperature and $Hg^{2+}$ ions with enhanced detection sensitivity," *J. Mater. Chem.* 20:10716-10723, 2010.
Stewart et al., "The Fluorescence of a Chelating Two-Photon-Absorbing Dye is Enhanced with the Addition of Transition Metal Ions but Quenched in the Presence of Acid," *Proc. Of SPIE* 9939(993904):1-10, 2016.
Zhang et al., "FRET Imaging of Enzyme-Responsive HPMA Copolymer Conjugate," *Macromolecular Bioscience* 17(1600215):1-8, 2017.
Aviñó et al., "Solid-phase synthesis of oligomers carrying several chromophore units linked by phosphodiester backbones," *Bioorganic & Medicinal Chemistry Letters* 18:2306-2310, 2008.
Bag et al., "Triazolyl-donor-acceptor chromophore-decorated unnatural amino acids and peptides: FRET events in a β-turn conformation," *Chem. Commun.* 50:433-435, 2014.
Boldyrev et al., "Synthesis and Characteristics of New Fluorescent Probes Based on Cardiolipin," *Russian Journal of Bioorganic Chemistry* 35(2):219-224, 2009.
Breul et al., "Fluorescent monomers as building blocks for dye labeled polymers: synthesis and application in energy conversion, biolabeling and sensors," Chem. Soc. Rev. 42(12):5366-5407, 2013.
CAS Registry No. 862288-26-4, American Chemical Society, 2021. (1 page).
Chang et al., "A General Approach for Generating Fluorescent Probes to Visualize Piconewton Forces at the Cell Surface," *J. Am. Chem. Soc.* 138:2901-2904, 2016. (4 pages).
Damian et al., "Synthesis and DNA Interaction of Platinum Complex/Peptide Chimera as Potential Drug Candidates," *Eur. J. Org. Chem.* 6161-6170, 2010.
De Vos et al., "New Non Nucleosidic Phosphoramidites for the Solid Phase Multi-Labelling of Oligonucleotides: Comb- and Multifork-Like Structures," *Nucleosides & Nucleotides* 13(10):2245-2265, 1994.
Drescher et al., "General Synthesis and Aggregation Behaviour of New Single-Chain Bolaphospholipids: Variations in Chain and Headgroup Structures," *Chemistry—A European Journal* 14(22):6796-6804, 2008.
Dropulic et al., "Update on New Antivirals Under Development for the Treatment of Double-Stranded DNA Virus Infections," Clinical Pharmacology & Therapeutics 88(5):610-619, Nov. 2010.
Finniss et al., "A versatile acid-labile linker for antibody-drug conjugates," Med. Chem, Commun; 5; Apr. 1, 2014, 4 pages.
Griesang et al., "Four-Color, Enzyme-Free Interrogation of DNA Sequences with Chemically Activated, 3'-Fluorphore-Labeled Nucleotides," *Angew. Chem. Int. Ed.* 45:6144-6148, 2006.
Guryev et al., "Control of the Fluorescence of Dye-Antibody Conjugates by (2-Hydroxypropyl)-β-cyclodextrin in Fluorescence Microscopy and Flow Cytometry," *Analytical Chemistry* 83:7109-7114, Aug. 16, 2011.
Irani et al., "Molecular properties of human IgG subclasses and their implications for designing therapeutic monoclonal antibodies against infectious diseases," *Molecular Immunology* 67:171-182, 2015.
Kashida et al., "A Cationic Dye Triplet as a Unique "Glue" That Can Connect Fully Matched Termini of DNA Duplexes," *Chem. Eur. J.* 17:2614-2622, 2011.
Khanna et al., "2,6-Diarylethynylanthracenes: synthesis, morphology, and electro-optical properties," *Tetrahedron Letters* 53:6383-6387, 2012.

(56) References Cited

OTHER PUBLICATIONS

Krueger at al., "Fluorescent Amino Acids: Modular Building Blocks for the Assembly of New Tools for Chemical Biology," *ChemBioChem* 14:788-799, 2013.
Lapeyre et al., "Aryldithioethyloxycarbonyl (Ardec): A New Family of Amine Protecting Groups Removable under Mild Reducing Conditions and Their Applications to Peptide Synthesis," *Chem. Eur. J.* 12:3655-3671, 2006.
Lewis et al., "Orientation Control of Fluorescence Resonance Energy Transfer Using DNA as a Helical Scaffold," *J. Am. Chem. Soc.* 127(28):10002-10003, 2005.
McKinlay et al., "Cell-Penetrating, Guanidinium-Rich Oligophosphoesters: Effective and Versatile Molecular Transporters for Drug and Probe Delivery," *J. Am. Chem. Soc.* 138:3510-3517, Feb. 22, 2016.
Mthembu et al., "Breaking a Couple: Disulfide Reducing Agents," *ChemBioChem* 21, 2020. (10 pages).
Moss, "Nomenclature of Fused and Bridged Fused Ring Systems," *Pure & Appl. Chem.* 70(1):143-216, 1998.
Nolting, "Linker Technology for Antibody-Drug Conjugates," in Ducry (ed.), *Antibody-Drug Conjugates*, Humana Press, Totowa, NJ, 2013, Ch. 5, pp. 71-100.
Pelegrin et al., "Antiviral Monoclonal Antibodies: Can They Be More Than Simple Neutralizing Agents?" *Trends in Microbiology* 23(10):653-665, Oct. 2015.
Phares et al., "Improving the Stability and Sensing of Electrochemical Biosensors by Employing Trithiol-Anchoring Groups in a Six-Carbon Self-Assembled Monolayer," *Anal. Chem.* 81(3):1095-1100, Feb. 1, 2009.
Poupart et al., "Aminopropargyl derivative of terpyridine-bis(methylenamine) tetraacetic acid chelate of europium (Eu (TMT)-AP3): a new reagent for fluorescent labelling of proteins and peptides," *Org. Biomol. Chem.* 4:4165-4177, Oct. 2006.
Rochat et al., "Water-Soluble Cationic Conjugated Polymers: Response to Electron-Rich Bioanalytes," *J. Am. Chem. Soc.* 135:17703-17706, 2013.
Rupcich et al., "Quenching of Fluorophore-Labeled DNA Oligonucleotides by Divalent Metal Ions: Implications for Selection, Design, and Applications of Signaling Aptamers and Signaling Deoxyribozymes," J. Am. Chem. Soc. 126(3):780-790, 2006.
Shuman et al., "Bacterial DNA repair by non-homologous end joining," *Nature Reviews Microbiology* 5:852-861, Nov. 2007.
Sun et al., "Dual-Color Fluorescence Imaging of Magnetic Nanoparticles in Live Cancer Cells Using Conjugated Polymer Probes," *Scientific Reports* 6:22368, 2016. (12 pages).
Sun et al., "High yield production of high molecular weight poly(ethylene glycol)/ α-cyclodextrin polyrotaxanes by aqueous one-pot approach," *Polymer* 53:2884-2889, 2012.
Sun et al., "Ultrabright and Multicolorful Fluorescence of Amphiphilic Polyethyleneimine Polymer Dots for Efficiently Combined Imaging and Therapy," *Scientific Reports* 3:3036, 2013. (6 pages).
Teyssot et al., "Aromatic Nitrogen Donors for Efficient Copper(1)-NHC CuAAC under Reductant-Free Conditions," *Eur. J. Org. Chem.* 3507-3515, 2010.
Vybornyi et al., "Formation of Two-Dimensional Supramolecular Polymers by Amphiphilic Pyrene Oligomers," *Angew. Chem. Int. Ed.* 52:114488-11493, 2013.
Wang et al., "Fluorescence-Based Evaluation of the Partitioning of Lipids and Lipidated Peptides into Liquid-Ordered Lipid Microdomains: A Model for Molecular Partitioning into Lipid Rafts," *Biophysical Journal* 79:919-933, Aug. 2000.
Winiger et al., "Long-Distance Electronic Energy Transfer in Light-Harvesting Supramolecular Polymers," *Angew. Chem. Int. Ed.* 53:13609-13613, 2014.
Yu et al., "Targeted Delivery of an Anti-Inflammatory PDE4 Inhibitor to Immune Cells via an Antibody-drug Conjugate," Molecular Therapy 24(12):2078-2089, Dec. 2016.
Zhao et al., "Mussel-Inspired One-Pot Synthesis of a Fluorescent and Water-Soluble Polydopamine-Polyethyleneimine Copolymer," Macromol. Rapid Commun. 36:909-915, 2015.

U.S. Appl. No. 17/458,149, filed Aug. 26, 2021.
U.S. Appl. No. 17/458,938, filed Aug. 27, 2021.
U.S. Appl. No. 17/602,689, filed Oct. 8, 2021.
U.S. Appl. No. 17/602,722, filed Oct. 8, 2021.
U.S. Appl. No. 17/602,718, filed Oct. 8, 2021.
U.S. Appl. No. 16/090,560, filed Oct. 1, 2018.
U.S. Appl. No. 16/639,496, filed Feb. 14, 2020.
U.S. Appl. No. 16/763,922, filed May 13, 2020.
U.S. Appl. No. 16/771,185, filed Jun. 9, 2020.
U.S. Appl. No. 16/879,572, filed May 20, 2020.
U.S. Appl. No. 16/934,912, filed Jul. 21, 2020.
U.S. Appl. No. 16/961,403, filed Jul. 10, 2020.
U.S. Appl. No. 16/961,414, filed Jul. 10, 2020.
U.S. Appl. No. 16/961,429, filed Jul. 10, 2020.
Chen et al., "Synthesis and properties of new segmented block poly(urethane-urea)s containing phosphatidylcholine analogues and polybutadienes," *Macro-Molecular Chemistry and Physics* 197(5):1587-1597, May 1996. (11 pages).
Ciccotelli et al., "Polyguanine-conjugated antigens for scavenger receptor targeting and self-adjuvanting vaccines (VAC13P.1125)," *The Journal of Immunology* 194(Suppl. 1):214.5, May 1, 2015 [Abstract]. (1 page).
Franzini et al., "Identification of Structure-Activity Relationships from Screening a Structurally Compact DNA-Encoded Chemical Library," *Angewandte Chemie International Edition* 54:3927-3931, Feb. 3, 2015 [with supporting information]. (41 pages).
Gupta et al., "Dendrimers: Novel Polymeric Nanoarchitectures for Solubility Enhancement," *Biomacromolecules* 7(3):649-658, Mar. 2006 [Published online Feb. 15, 2006]. (10 pages).
Hasegawa et al., "Cysteine, histidine and glycine exhibit anti-inflammatory effects in human coronary arterial endothelial cells," *Clinical and Experimental Immunology* 167:269-274, Jan. 11, 2012. (6 pages).
Khandare et al., "Polymer-drug conjugates: Progress in polymeric prodrugs," *Progress in Polymer Science* 31(4):359-397, Apr. 2006. (39 pages).
Liu et al., "Increased Cytotoxicity and Decreased In Vivo Toxicity of FdUMP[10] Relative to 5-FU," *Nucleosides & Nucleotides* 18(8):1789-1802, Aug. 1999. (14 pages).
Liu et al., "Structure-based programming of lymph-node targeting in molecular vaccines," *Nature* 507:519-522, Mar. 27, 2014 [Published online Feb. 16, 2014]. (15 pages).
Midoux et al., "Chemical vectors for gene delivery: a current review on polymers, peptides and lipids containing histidine or imidazole as nucleic acids carriers," *British Journal of Pharmacology* 157:166-178, May 2009. (13 pages).
Mielewczyk et al., "5' end fluorescent labelling of oligonucleotides with riboflavin-derived phosphitylating reagent," *Acta Biochimica Polonica* 36(3-4):225-233, 1989. (9 pages).
Oh et al., "Low-dose guanidine and pyridostigmine: relatively safe and effective long-term symptomatic therapy in Lambert-Eaton myasthenic syndrome," *Muscle & Nerve* 20:1146-1152, Sep. 1997. (7 pages).
Petersen et al., "Acyclic, achiral enamide nucleoside analogues. The importance of the C=C bond in the analogue for its ability to mimic natural nucleosides," *Organic & Biomolecular Chemistry* 1:3293-3296, Sep. 4, 2003. (4 pages).
Reed et al., "Structure-activity relationships of cytotoxic cholesterol-modified DNA duplexes," *Journal of Medicinal Chemistry* 38(22):4587-4596, Oct. 27, 1995. (10 pages).
Samal et al., "Cationic polymers and their therapeutic potential," *Chemical Society Reviews* 41:7147-7194, Aug. 2012. (48 pages).
Shuey et al., "Cyclohexanediol Bisphosphates as Models for Phospholipid-Metal Ion Binding Sites," *Bioorganic Chemistry* 21:95-108, Mar. 1993. (14 pages).
STIC Search Report from American Chemical Society, for U.S. Appl. No. 17/255,353, dated Sep. 7, 2023. (143 pages).
Striebel et al., "Enhancing sensitivity of human herpes virus diagnosis with DNA microarrays using dendrimers," *Experimental and Molecular Pathology* 77:89-97, Oct. 2004 [Published online Jul. 15, 2004]. (9 pages).

(56) References Cited

OTHER PUBLICATIONS

Sun et al., "Self-assembled biodegradable micellar nanoparticles of amphiphilic and cationic block copolymer for siRNA delivery," *Biomaterials* 29:4348-4355, available online Aug. 2008. (8 pages).
Tabujew et al., "Chapter One: Functionalization of Cationic Polymers for Drug Delivery Applications," *RSC Polymer Chemistry Series 13*, 2015. (29 pages).
Wu Yi et al., "$^{Py}$A-Modified Oligodeoxyadenylates: Expanded Fluorescence Phenomena and Structural Formation," *Chemistry—An Asian Journal* 7:60-63, Nov. 2011. (4 pages).
U.S. Appl. No. 18/425,634, filed Jan. 29, 2024.
U.S. Appl. No. 18/570,283, filed Dec. 14, 2023.
U.S. Appl. No. 18/412,316, filed Jan. 12, 2024.
U.S. Appl. No. 18/436,594, filed Feb. 8, 2024.
U.S. Appl. No. 18/256,125, filed Jun. 6, 2023.
U.S. Appl. No. 18/481,045, filed Oct. 4, 2023.
U.S. Appl. No. 18/438,105, filed Feb. 9, 2024.
U.S. Appl. No. 16/982,341, filed Sep. 18, 2020.
U.S. Appl. No. 16/982,355, filed Sep. 18, 2020.
U.S. Appl. No. 17/121,596, filed Dec. 14, 2020.
U.S. Appl. No. 17/255,353, filed Dec. 22, 2020.

ULTRA BRIGHT DIMERIC OR POLYMERIC DYES AND METHODS FOR PREPARATION OF THE SAME

BACKGROUND

Field

Embodiments of the present invention are generally directed to methods for preparation of dimeric and polymeric fluorescent or colored dyes and compounds useful for the same.

Description of the Related Art

Fluorescent and/or colored dyes are known to be particularly suitable for applications in which a highly sensitive detection reagent is desirable. Dyes that are able to preferentially label a specific ingredient or component in a sample enable the researcher to determine the presence, quantity and/or location of that specific ingredient or component. In addition, specific systems can be monitored with respect to their spatial and temporal distribution in diverse environments.

Fluorescence and colorimetric methods are extremely widespread in chemistry and biology. These methods give useful information on the presence, structure, distance, orientation, complexation and/or location for biomolecules. In addition, time-resolved methods are increasingly used in measurements of dynamics and kinetics. As a result, many strategies for fluorescence or color labeling of biomolecules, such as nucleic acids and protein, have been developed. Since analysis of biomolecules typically occurs in an aqueous environment, the focus has been on development and use of water soluble dyes.

Highly fluorescent or colored dyes are desirable since use of such dyes increases the signal to noise ratio and provides other related benefits. Accordingly, attempts have been made to increase the signal from known fluorescent and/or colored moieties. For example, dimeric and polymeric compounds comprising two or more fluorescent and/or colored moieties have been prepared in anticipation that such compounds would result in brighter dyes. However, as a result of intramolecular fluorescence quenching, the known dimeric and polymeric dyes have not achieved the desired increase in brightness.

There is thus a need in the art for methods for preparation of water soluble dyes having an increased molar brightness. Ideally, such dyes and biomarkers should be intensely colored or fluorescent and should be available in a variety of colors and fluorescent wavelengths. The present invention fulfills this need and provides further related advantages.

BRIEF SUMMARY

In brief, embodiments of the present invention are generally directed to compounds useful as water soluble, fluorescent and/or colored dyes and/or probes that enable visual detection of analyte molecules, such as biomolecules, as well as reagents for their preparation. Methods for visually detecting analyte molecules using the dyes are also described. Further embodiments include methods and compounds useful for preparation of such fluorescent and/or colored dyes.

The water soluble, fluorescent or colored dyes of embodiments of the invention are intensely colored and/or fluorescent and can be readily observed by visual inspection or other means. In some embodiments the compounds may be observed without prior illumination or chemical or enzymatic activation. By appropriate selection of the dye, as described herein, visually detectable analyte molecules of a variety of colors may be obtained.

In one embodiment, is provided a method for preparing a dimeric or polymeric dye, the method comprising reacting a first and second compound of structure (I):

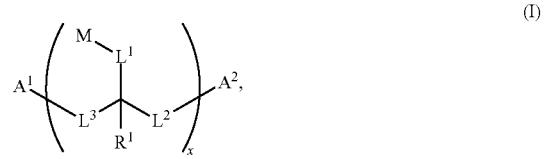

with a compound of structure (II):

$$(B^1)_y L^4 (B^2)_z,\qquad (II)$$

wherein $A^1$, $A^2$, $B^1$, $B^2$, $L^1$, $L^2$, $L^3$, $L^4$, M, $R^1$, x, y and z are as defined herein.

In a different embodiment is provided a method for preparing a dimeric or polymeric dye, the method comprising reacting a first compound of structure (I):

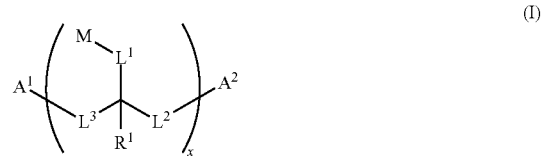

with a second compound of structure (I), wherein $A^1$, $A^2$, $L^1$, $L^2$, $L^3$, M, $R^1$ and x are as defined herein.

Other embodiments are directed to a compound having one of the following structures (III), (IV) or (V):

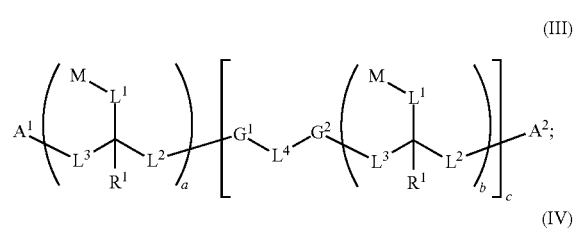

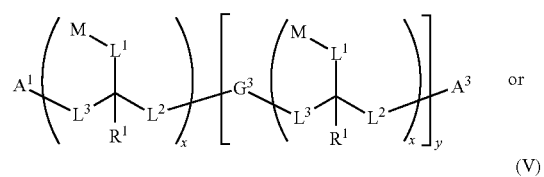

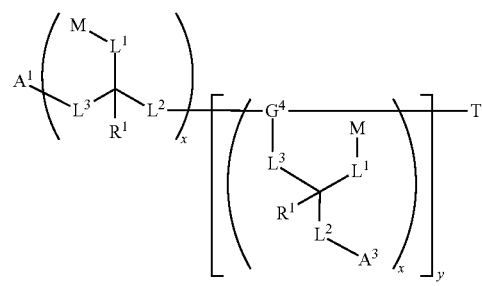

wherein $A^1$, $A^2$, A3, $G^1$, $G^2$, G3, G4, $L^1$, $L^2$, $L^3$, $L^4$, M, $R^1$, T, a, b, c, x and y are as defined herein.

In another embodiment, a method for staining a sample is provided, the method comprises adding to said sample a compound of structure (III), (IV) or (V) in an amount sufficient to produce an optical response when said sample is illuminated at an appropriate wavelength.

In still other embodiments, the present disclosure provides a method for visually detecting an analyte molecule, comprising:
  (a) providing a compound of (III), (IV) or (V); and
  (b) detecting the compound by its visible properties.

Other disclosed methods include a method for visually detecting a biomolecule, the method comprising:
  (a) admixing a compound of structure (III), (IV) or (V) with one or more biomolecules; and
  (b) detecting the compound by its visible properties.

Other embodiments provide a method for visually detecting an analyte, the method comprising:
  (a) providing a compound of structure (III), (IV) or (V), wherein $A^1$ or $A^2$ comprises a linker comprising a covalent bond to a targeting moiety having specificity for the analyte;
  (b) admixing the compound and the analyte, thereby associating the targeting moiety and the analyte; and
  (c) detecting the compound by its visible properties.

Other embodiments are directed to a composition comprising a compound of structure (III), (IV) or (V) and one or more analyte molecule, such as a biomolecule. Use of such compositions in analytical methods for detection of the one or more biomolecules is also provided.

These and other aspects of the invention will be apparent upon reference to the following detailed description.

DETAILED DESCRIPTION

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —NH$_2$ group.
"Carboxy" refers to the —CO$_2$H group.
"Cyano" refers to the —CN group.
"Formyl" refers to the —C(=O)H group.
"Hydroxy" or "hydroxyl" refers to the —OH group.
"Imino" refers to the =NH group.
"Nitro" refers to the —NO$_2$ group.
"Oxo" refers to the =O substituent group.
"Sulfhydryl" refers to the —SH group.
"Thioxo" refers to the =S group.

"Alkyl" refers to a straight or branched hydrocarbon chain group consisting solely of carbon and hydrogen atoms, containing no unsaturation, having from one to twelve carbon atoms ($C_1$-$C_{12}$ alkyl), one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, alkyl groups are optionally substituted.

"Alkylene" or "alkylene chain" refers to a straight or branched divalent hydrocarbon chain linking the rest of the molecule to a radical group, consisting solely of carbon and hydrogen, containing no unsaturation, and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, alkylene is optionally substituted.

"Alkenylene" or "alkenylene chain" refers to a straight or branched divalent hydrocarbon chain linking the rest of the molecule to a radical group, consisting solely of carbon and hydrogen, containing at least one carbon-carbon double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain. Unless stated otherwise specifically in the specification, alkenylene is optionally substituted.

"Alkynylene" or "alkynylene chain" refers to a straight or branched divalent hydrocarbon chain linking the rest of the molecule to a radical group, consisting solely of carbon and hydrogen, containing at least one carbon-carbon triple bond and having from two to twelve carbon atoms, e.g., ethenylene, propenylene, n-butenylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain. Unless stated otherwise specifically in the specification, alkynylene is optionally substituted.

"Alkylether" refers to any alkyl group as defined above, wherein at least one carbon-carbon bond is replaced with a carbon-oxygen bond. The carbon-oxygen bond may be on the terminal end (as in an alkoxy group) or the carbon oxygen bond may be internal (i.e., C—O—C). Alkylethers include at least one carbon oxygen bond, but may include more than one. For example, polyethylene glycol (PEG) is included within the meaning of alkylether. Unless stated otherwise specifically in the specification, an alkylether group is optionally substituted. For example, in some embodiments an alkylether is substituted with an alcohol or —OP(=$R_a$)($R_b$)$R_c$, wherein each of $R_a$, $R_b$ and $R_c$ is as defined for compounds of structure (I).

"Alkoxy" refers to a group of the formula —OR$_a$ where R$_a$ is an alkyl group as defined above containing one to twelve carbon atoms. Unless stated otherwise specifically in the specification, an alkoxy group is optionally substituted.

"Alkoxyalkylether" refers to a group of the formula —$OR_aR_b$ where $R_a$ is an alkylene group as defined above containing one to twelve carbon atoms, and $R_b$ is an alkylether group as defined herein. Unless stated otherwise specifically in the specification, an alkoxyalkylether group is optionally substituted, for example substituted with an alcohol or —OP(=$R_a$)($R_b$)$R_c$, wherein each of $R_a$, $R_b$ and $R_c$ is as defined for compounds of structure (I).

"Heteroalkyl" refers to an alkyl group, as defined above, comprising at least one heteroatom (e.g., N, O, P or S) within the alkyl group or at a terminus of the alkyl group. In some embodiments, the heteroatom is within the alkyl group (i.e., the heteroalkyl comprises at least one carbon-[heteroatom]$_x$-carbon bond, where x is 1, 2 or 3). In other embodiments, the heteroatom is at a terminus of the alkyl group and thus serves to join the alkyl group to the remainder of the molecule (e.g., M1-H-A), where M1 is a portion of the molecule, H is a heteroatom and A is an alkyl group). Unless stated otherwise specifically in the specification, a heteroalkyl group is optionally substituted. Exemplary heteroalkyl groups include ethylene oxide (e.g., polyethylene oxide), optionally including phosphorous-oxygen bonds, such as phosphodiester bonds.

"Heteroalkoxy" refers to a group of the formula —$OR_a$ where $R_a$ is a heteroalkyl group as defined above containing one to twelve carbon atoms. Unless stated otherwise specifically in the specification, a heteroalkoxy group is optionally substituted.

"Heteroalkylene" refers to an alkylene group, as defined above, comprising at least one heteroatom (e.g., N, O, P or S) within the alkylene chain or at a terminus of the alkylene chain. In some embodiments, the heteroatom is within the alkylene chain (i.e., the heteroalkylene comprises at least one carbon-[heteroatom]-carbon bond, where x is 1, 2 or 3). In other embodiments, the heteroatom is at a terminus of the alkylene and thus serves to join the alkylene to the remainder of the molecule (e.g., M1-H-A-M2, where M1 and M2 are portions of the molecule, H is a heteroatom and A is an alkylene). Unless stated otherwise specifically in the specification, a heteroalkylene group is optionally substituted. Exemplary heteroalkylene groups include ethylene oxide (e.g., polyethylene oxide) and the "C" linking group illustrated below:

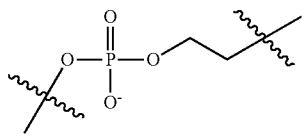

"C linker"

Multimers of the above C-linker are included in various embodiments of heteroalkylene linkers.

"Heteroalkenylene" is a heteroalkylene, as defined above, comprising at least one carbon-carbon double bond. Unless stated otherwise specifically in the specification, a heteroalkenylene group is optionally substituted.

"Heteroalkynylene" is a heteroalkylene comprising at least one carbon-carbon triple bond. Unless stated otherwise specifically in the specification, a heteroalkynylene group is optionally substituted.

"Heteroatomic" in reference to a "heteroatomic linker" refers to a linker group consisting of one or more heteroatoms. Exemplary heteroatomic linkers include single atoms selected from the group consisting of O, N, P and S, and multiple heteroatoms for example a linker having the formula —P(O$^-$)(=O)O— or —OP(O$^-$)(=O)O— and multimers and combinations thereof.

"Phosphate" refers to the —OP(=O)($R_a$)$R_b$ group, wherein $R_a$ is OH, O$^-$ or O$R_c$; and $R_b$ is OH, O$^-$, O$R_c$, a thiophosphate group or a further phosphate group, wherein $R_c$ is a counter ion (e.g., Na+ and the like).

"Phosphoalkyl" refers to the —OP(=O)($R_a$)$R_b$ group, wherein $R_a$ is OH, O$^-$ or O$R_c$; and $R_b$ is —Oalkyl, wherein $R_c$ is a counter ion (e.g., Na+ and the like). Unless stated otherwise specifically in the specification, a phosphoalkyl group is optionally substituted. For example, in certain embodiments, the —Oalkyl moiety in a phosphoalkyl group is optionally substituted with one or more of hydroxyl, amino, sulfhydryl, phosphate, thiophosphate, phosphoalkyl, thiophosphoalkyl, phosphoalkylether, thiophosphoalkylether or —OP(=$R_a$)($R_b$)$R_c$, wherein each of $R_a$, $R_b$ and $R_c$ is as defined for compounds of structure (I).

"Phosphoalkylether" refers to the —OP(=O)($R_a$)$R_b$ group, wherein $R_a$ is OH, O$^-$ or O$R_c$; and $R_b$ is —Oalkylether, wherein $R_c$ is a counter ion (e.g., Na+ and the like). Unless stated otherwise specifically in the specification, a phosphoalkylether group is optionally substituted. For example, in certain embodiments, the —Oalkylether moiety in a phosphoalkylether group is optionally substituted with one or more of hydroxyl, amino, sulfhydryl, phosphate, thiophosphate, phosphoalkyl, thiophosphoalkyl, phosphoalkylether, thiophosphoalkylether or —OP(=$R_a$)($R_b$)$R_c$, wherein each of $R_a$, $R_b$ and $R_c$ is as defined for compounds of structure (I).

"Thiophosphate" refers to the —OP(=$R_a$)($R_b$)$R_c$ group, wherein $R_a$ is O or S, $R_b$ is OH, O$^-$, S$^-$, O$R_d$ or S$R_d$; and $R_c$ is OH, SH, O$^-$, S$^-$, O$R_d$, S$R_d$, a phosphate group or a further thiophosphate group, wherein $R_d$ is a counter ion (e.g., Na+ and the like) and provided that: i) $R_a$ is S; ii) $R_b$ is S$^-$ or S$R_d$; iii) $R_c$ is SH, S$^-$ or S$R_d$; or iv) a combination of i), ii) and/or iii).

"Thiophosphoalkyl" refers to the —OP(=$R_a$)($R_b$)$R_c$ group, wherein $R_a$ is O or S, $R_b$ is OH, O$^-$, S$^-$, O$R_d$ or S$R_d$; and $R_c$ is —Oalkyl, wherein $R_d$ is a counter ion (e.g., Na+ and the like) and provided that: i) $R_a$ is S; ii) $R_b$ is S$^-$ or S$R_d$; or iii) $R_a$ is S and $R_b$ is S$^-$ or S$R_d$. Unless stated otherwise specifically in the specification, a thiophosphoalkyl group is optionally substituted. For example, in certain embodiments, the —Oalkyl moiety in a thiophosphoalkyl group is optionally substituted with one or more of hydroxyl, amino, sulfhydryl, phosphate, thiophosphate, phosphoalkyl, thiophosphoalkyl, phosphoalkylether, thiophosphoalkylether or —OP(=$R_a$)($R_b$)$R_c$, wherein each of $R_a$, $R_b$ and $R_c$ is as defined for compounds of structure (I).

"Thiophosphoalkylether" refers to the —OP(=$R_a$)($R_b$)$R_c$ group, wherein $R_a$ is O or S, $R_b$ is OH, O$^-$, S$^-$, O$R_d$ or S$R_d$; and $R_c$ is —Oalkylether, wherein $R_d$ is a counter ion (e.g., Na+ and the like) and provided that: i) $R_a$ is S; ii) $R_b$ is S$^-$ or S$R_d$; or iii) $R_a$ is S and $R_b$ is S$^-$ or S$R_d$. Unless stated otherwise specifically in the specification, a thiophosphoalkylether group is optionally substituted. For example, in certain embodiments, the —Oalkylether moiety in a thiophosphoalkyl group is optionally substituted with one or more of hydroxyl, amino, sulfhydryl, phosphate, thiophosphate, phosphoalkyl, thiophosphoalkyl, phosphoalkylether, thiophosphoalkylether or —OP(=$R_a$)($R_b$)$R_c$, wherein each of $R_a$, $R_b$ and $R_c$ is as defined for compounds of structure (I).

"Carbocyclic" refers to a stable 3- to 18-membered aromatic or non-aromatic ring comprising 3 to 18 carbon atoms.

Unless stated otherwise specifically in the specification, a carbocyclic ring may be a monocyclic, bicyclic, tricyclic or tetracyclic ring system, which may include fused or bridged ring systems, and may be partially or fully saturated. Non-aromatic carbocyclyl radicals include cycloalkyl, while aromatic carbocyclyl radicals include aryl. Unless stated otherwise specifically in the specification, a carbocyclic group is optionally substituted.

"Cycloalkyl" refers to a stable non-aromatic monocyclic or polycyclic carbocyclic ring, which may include fused or bridged ring systems, having from three to fifteen carbon atoms, preferably having from three to ten carbon atoms, and which is saturated or unsaturated and attached to the rest of the molecule by a single bond. Monocyclic cycloalkyls include, for example, cyclopropyl, cyclobutyl, cyclopentyl, cyclohexyl, cycloheptly, and cyclooctyl. Polycyclic cycloalkyls include, for example, adamantyl, norbornyl, decalinyl, 7,7-dimethyl-bicyclo-[2.2.1]heptanyl, and the like. Unless stated otherwise specifically in the specification, a cycloalkyl group is optionally substituted.

"Aryl" refers to a ring system comprising at least one carbocyclic aromatic ring. In some embodiments, an aryl comprises from 6 to 18 carbon atoms. The aryl ring may be a monocyclic, bicyclic, tricyclic or tetracyclic ring system, which may include fused or bridged ring systems. Aryls include, but are not limited to, aryls derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl group is optionally substituted.

"Heterocyclic" refers to a stable 3- to 18-membered aromatic or non-aromatic ring comprising one to twelve carbon atoms and from one to six heteroatoms selected from the group consisting of nitrogen, oxygen and sulfur. Unless stated otherwise specifically in the specification, the heterocyclic ring may be a monocyclic, bicyclic, tricyclic or tetracyclic ring system, which may include fused or bridged ring systems; and the nitrogen, carbon or sulfur atoms in the heterocyclic ring may be optionally oxidized; the nitrogen atom may be optionally quaternized; and the heterocyclic ring may be partially or fully saturated. Examples of aromatic heterocyclic rings are listed below in the definition of heteroaryls (i.e., heteroaryl being a subset of heterocyclic). Examples of non-aromatic heterocyclic rings include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, pyrazolopyrimidinyl, quinuclidinyl, thiazolidinyl, tetrahydrofuryl, trioxanyl, trithianyl, triazinanyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclic group is optionally substituted.

"Heteroaryl" refers to a 5- to 14-membered ring system comprising one to thirteen carbon atoms, one to six heteroatoms selected from the group consisting of nitrogen, oxygen and sulfur, and at least one aromatic ring. For purposes of certain embodiments of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrrolyl, pyrido[2,3-d]pyrimidinonyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e. thienyl). Unless stated otherwise specifically in the specification, a heteroaryl group is optionally substituted.

"Fused" refers to a ring system comprising at least two rings, wherein the two rings share at least one common ring atom, for example two common ring atoms. When the fused ring is a heterocyclyl ring or a heteroaryl ring, the common ring atom(s) may be carbon or nitrogen. Fused rings include bicyclic, tricyclic, tertracyclic, and the like.

The term "substituted" used herein means any of the above groups (e.g., alkyl, alkylene, alkenylene, alkynylene, heteroalkylene, heteroalkenylene, heteroalkynylene, alkoxy, alkylether, alkoxyalkylether, heteroalkyl, heteroalkoxy, phosphoalkyl, phosphoalkylether, thiophosphoalkyl, thiophosphoalkylether, carbocyclic, cycloalkyl, aryl, heterocyclic and/or heteroaryl) wherein at least one hydrogen atom (e.g., 1, 2, 3 or all hydrogen atoms) is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In some embodiments, the optional substituent is —OP(=$R_a$)($R_b$)$R_c$, wherein each of $R_a$, $R_b$ and $R_c$ is as defined for compounds of structure (I). In addition, each of the foregoing substituents may also be optionally substituted with one or more of the above substituents.

"Conjugation" refers to the overlap of one p-orbital with another p-orbital across an intervening sigma bond. Conjugation may occur in cyclic or acyclic compounds. A "degree of conjugation" refers to the overlap of at least one p-orbital with another p-orbital across an intervening sigma bond. For example, 1, 3-butadine has one degree of conjugation, while benzene and other aromatic compounds typically have multiple degrees of conjugation. Fluorescent and colored compounds typically comprise at least one degree of conjugation.

"Fluorescent" refers to a molecule which is capable of absorbing light of a particular frequency and emitting light of a different frequency. Fluorescence is well-known to those of ordinary skill in the art.

"Colored" refers to a molecule which absorbs light within the colored spectrum (i.e., red, yellow, blue and the like).

A "linker" refers to a contiguous chain of at least one atom, such as carbon, oxygen, nitrogen, sulfur, phosphorous and combinations thereof, which connects a portion of a molecule to another portion of the same molecule or to a different molecule, moiety or solid support (e.g., microparticle). Linkers may connect the molecule via a covalent bond or other means, such as ionic or hydrogen bond interactions.

The term "biomolecule" refers to any of a variety of biological materials, including nucleic acids, carbohydrates, amino acids, polypeptides, glycoproteins, hormones, aptamers and mixtures thereof. More specifically, the term is intended to include, without limitation, RNA, DNA, oligonucleotides, modified or derivatized nucleotides, enzymes, receptors, prions, receptor ligands (including hormones), antibodies, antigens, and toxins, as well as bacteria, viruses, blood cells, and tissue cells. The visually detectable biomolecules of the invention (e.g., compounds of structure (I) having a biomolecule linked thereto) are prepared, as further described herein, by contacting a biomolecule with a compound having a reactive group that enables attachment of the biomolecule to the compound via any available atom or functional group, such as an amino, hydroxy, carboxyl, or sulfhydryl group on the biomolecule.

A "reactive group" is a moiety capable of reacting with a second reactive groups (e.g., a "complementary reactive group") to form one or more covalent bonds, for example by a displacement, oxidation, reduction, addition or cycloaddition reaction. Exemplary reactive groups are provided in Table 1, and include for example, nucleophiles, electrophiles, dienes, dienophiles, aldehyde, oxime, hydrazone, alkyne, amine, azide, acylazide, acylhalide, nitrile, nitrone, sulfhydryl, disulfide, sulfonyl halide, isothiocyanate, imidoester, activated ester, ketone, α,β-unsaturated carbonyl, alkene, maleimide, α-haloimide, epoxide, aziridine, tetrazine, tetrazole, phosphine, biotin, thiirane and the like.

The terms "visible" and "visually detectable" are used herein to refer to substances that are observable by visual inspection, without prior illumination, or chemical or enzymatic activation. Such visually detectable substances absorb and emit light in a region of the spectrum ranging from about 300 to about 900 nm. Preferably, such substances are intensely colored, preferably having a molar extinction coefficient of at least about 40,000, more preferably at least about 50,000, still more preferably at least about 60,000, yet still more preferably at least about 70,000, and most preferably at least about 80,000 $M^{-1}$ $cm^{-1}$. The compounds of embodiments of the invention may be detected by observation with the naked eye, or with the aid of an optically based detection device, including, without limitation, absorption spectrophotometers, transmission light microscopes, digital cameras and scanners. Visually detectable substances are not limited to those which emit and/or absorb light in the visible spectrum. Substances which emit and/or absorb light in the ultraviolet (UV) region (about 10 nm to about 400 nm), infrared (IR) region (about 700 nm to about 1 mm), and substances emitting and/or absorbing in other regions of the electromagnetic spectrum are also included with the scope of "visually detectable" substances.

For purposes of embodiments of the invention, the term "photostable visible dye" refers to a chemical moiety that is visually detectable, as defined hereinabove, and is not significantly altered or decomposed upon exposure to light. Preferably, the photostable visible dye does not exhibit significant bleaching or decomposition after being exposed to light for at least one hour. More preferably, the visible dye is stable after exposure to light for at least 12 hours, still more preferably at least 24 hours, still yet more preferably at least one week, and most preferably at least one month. Nonlimiting examples of photostable visible dyes suitable for use in the compounds and methods of the invention include azo dyes, thioindigo dyes, quinacridone pigments, dioxazine, phthalocyanine, perinone, diketopyrrolopyrrole, quinophthalone, and truarycarbonium.

As used herein, the term "perylene derivative" is intended to include any substituted perylene that is visually detectable. However, the term is not intended to include perylene itself. The terms "anthracene derivative", "naphthalene derivative", and "pyrene derivative" are used analogously. In some preferred embodiments, a derivative (e.g., perylene, pyrene, anthracene or naphthalene derivative) is an imide, bisimide or hydrazamimide derivative of perylene, anthracene, naphthalene, or pyrene.

The visually detectable molecules of various embodiments of the invention are useful for a wide variety of analytical applications, such as biochemical and biomedical applications, in which there is a need to determine the presence, location, or quantity of a particular analyte (e.g., biomolecule). In another aspect, therefore, the invention provides a method for visually detecting a biomolecule, comprising: (a) providing a biological system with a visually detectable biomolecule comprising the compound of structure (I) linked to a biomolecule; and (b) detecting the biomolecule by its visible properties. For purposes of the invention, the phrase "detecting the biomolecule by its visible properties" means that the biomolecule, without illumination or chemical or enzymatic activation, is observed with the naked eye, or with the aid of a optically based detection device, including, without limitation, absorption spectrophotometers, transmission light microscopes, digital cameras and scanners. A densitometer may be used to quantify the amount of visually detectable biomolecule present. For example, the relative quantity of the biomolecule in two samples can be determined by measuring relative optical density. If the stoichiometry of dye molecules per biomolecule is known, and the extinction coefficient of the dye molecule is known, then the absolute concentration of the biomolecule can also be determined from a measurement of optical density. As used herein, the term "biological system" is used to refer to any solution or mixture comprising one or more biomolecules in addition to the visually detectable biomolecule. Nonlimiting examples of such biological systems include cells, cell extracts, tissue samples, electrophoretic gels, assay mixtures, and hybridization reaction mixtures.

"Solid support" refers to any solid substrate known in the art for solid-phase support of molecules, for example a "microparticle" refers to any of a number of small particles useful for attachment to compounds of the invention, including, but not limited to, glass beads, magnetic beads, polymeric beads, nonpolymeric beads, and the like. In certain embodiments, a microparticle comprises polystyrene beads.

A "solid support reside" refers to the functional group remaining attached to a molecule when the molecule is cleaved from the solid support. Solid support residues are known in the art and can be easily derived based on the structure of the solid support and the group linking the molecule thereto.

A "targeting moiety" is a moiety that selectively binds or associates with a particular target, such as an analyte molecule. "Selectively" binding or associating means a targeting moiety preferentially associates or binds with the desired target relative to other targets. In some embodiments the compounds disclosed herein include linkages to targeting moieties for the purpose of selectively binding or associating the compound with an analyte of interest (i.e., the target of the targeting moiety), thus allowing detection of the analyte. Exemplary targeting moieties include, but are not limited to, antibodies, antigens, nucleic acid sequences, enzymes, proteins, cell surface receptor antagonists, and the like. In some embodiments, the targeting moiety is a moiety, such as an antibody, that selectively binds or associates with a target feature on or in a cell, for example a target feature on a cell membrane or other cellular structure, thus allowing for detection of cells of interest. Small molecules that selectively bind or associate with a desired analyte are also contemplated as targeting moieties in certain embodiments. One of skill in the art will understand other analytes, and the corresponding targeting moiety, that will be useful in various embodiments.

"Base pairing moiety" refers to a heterocyclic moiety capable of hybridizing with a complementary heterocyclic moiety via hydrogen bonds (e.g., Watson-Crick base pairing). Base pairing moieties include natural and unnatural bases. Non-limiting examples of base pairing moieties are RNA and DNA bases such adenosine, guanosine, thymidine, cytosine and uridine and analogues thereof.

Embodiments of the invention disclosed herein are also meant to encompass all compounds of structure (I) or (II) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively.

Isotopically-labeled compounds of structure (I) or (II) can generally be prepared by conventional techniques known to those skilled in the art or by processes analogous to those described below and in the following Examples using an appropriate isotopically-labeled reagent in place of the non-labeled reagent previously employed.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event or circumstances may or may not occur, and that the description includes instances where said event or circumstance occurs and instances in which it does not. For example, "optionally substituted alkyl" means that the alkyl group may or may not be substituted and that the description includes both substituted alkyl groups and alkyl groups having no substitution.

"Salt" includes both acid and base addition salts.

"Acid addition salt" refers to those salts which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Base addition salt" refers to those salts which are prepared from addition of an inorganic base or an organic base to the free acid. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Crystallizations may produce a solvate of the compounds described herein. Embodiments of the present invention include all solvates of the described compounds. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compounds of the invention may be true solvates, while in other cases the compounds of the invention may merely retain adventitious water or another solvent or be a mixture of water plus some adventitious solvent.

Embodiments of the compounds of the invention (e.g., compounds of structure I, II, III, IV or V), or their salts, tautomers or solvates may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. Embodiments of the present invention are meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposable mirror images of one another.

A "tautomer" refers to a proton shift from one atom of a molecule to another atom of the same molecule. The present invention includes tautomers of any said compounds. Various tautomeric forms of the compounds are easily derivable by those of ordinary skill in the art.

The chemical naming protocol and structure diagrams used herein are a modified form of the I.U.P.A.C. nomenclature system, using the ACD/Name Version 9.07 software program and/or ChemDraw Ultra Version 11.0 software naming program (CambridgeSoft). Common names familiar to one of ordinary skill in the art are also used.

In one embodiment is provided a method ("Method 1") for preparing a dimeric or polymeric dye, the method comprising reacting a first and second compound of structure (I):

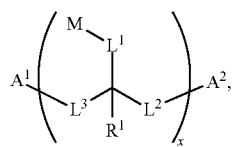

(I)

with a compound of structure (II):

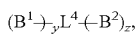

(II)

wherein:

A$^1$ and A$^2$ are each independently H, OH, SH, alkyl, alkoxy, alkylthio, alkylether, —OP(=R$_a$)(R$_b$)R$_c$, Q, L' or a moiety comprising a first functional group having complementary reactivity to B$^1$, B$^2$ or both, provided at least one of A$^1$ and A$^2$ is a moiety comprising a first functional group having complementary reactivity to B$^1$, B$^2$ or both, wherein: R$_a$ is O or S; R$_b$ is OH, SH, O$^-$, S$^-$, OR$_d$ or SR$_d$; R$_c$ is OH, SH, O$^-$, S$^-$, OR$_d$, OL', SR$_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether; and R$_d$ is a counter ion;

B$^1$ and B$^2$ are each independently a second functional group having complementary reactivity to the first functional group;

M is, at each occurrence, independently a fluorescent or colored dye moiety or Q, provided at least one occurrence of M is a fluorescent or colored dye moiety;

R$^1$ is, at each occurrence, independently H, alkyl or alkoxy;

Q is, at each occurrence, independently a moiety comprising a reactive group, or protected analogue thereof, capable of forming a covalent bond with an analyte molecule, a targeting moiety, a solid support or a complementary reactive group Q';

L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (I);

L$^1$, L$^2$ and L$^3$ are, at each occurrence, independently optional bivalent linker moieties;

L$^4$ is an optional multivalent linker moiety; and x, y and z are independently an integer of 1 or greater, thereby: i) forming a first bond between the first compound of structure (I) and the compound of structure (II) by reaction of B$^1$ with the first functional group of the first compound of structure (I); and ii) forming a second bond between the second compound of structure (I) and the compound of structure (II) by reaction of B$^2$ with the first functional group of the second compound of structure (I).

In other embodiments of Method 1:

A$^1$ and A$^2$ are each independently H, OH, SH, alkyl, alkoxy, alkylthio, alkylether, —OP(=R$_a$)(R$_b$)R$_c$, Q, a linker comprising a covalent bond to Q, a linker comprising a covalent bond to an analyte molecule, a linker comprising a covalent bond to a solid support, a linker comprising a covalent bond to a further compound of structure (I) or a moiety comprising a first functional group having complementary reactivity to B$^1$, B$^2$ or both, provided at least one of A$^1$ and A$^2$ is a moiety comprising a first functional group having complementary reactivity to B$^1$, B$^2$ or both, wherein: R$_a$ is O or S; R$_b$ is OH, SH, O$^-$, S$^-$, OR$_d$ or SR$_d$; R$_c$ is OH, SH, O$^-$, S$^-$, OR$_d$, SR$_d$, alkyl, alkoxy, alkylether, alkoxyalkylether, phosphate, thiophosphate, phosphoalkyl, thiophosphoalkyl, phosphoalkylether or thiophosphoalkylether; and R$_d$ is a counter ion;

B$^1$ and B$^2$ are each independently a second functional group having complementary reactivity to the first functional group;

M is, at each occurrence, independently a fluorescent or colored dye moiety or Q, provided at least one occurrence of M is a fluorescent or colored dye moiety;

$R^1$ is, at each occurrence, independently H, alkyl or alkoxy;

$L^1$, $L^2$ and $L^3$ are, at each occurrence, independently optional bivalent linker moieties;

$L^4$ is an optional multivalent linker moiety; and x, y and z are independently an integer of 1 or greater.

In some embodiments of Method 1, the dimeric or polymeric dye has the following structure (III):

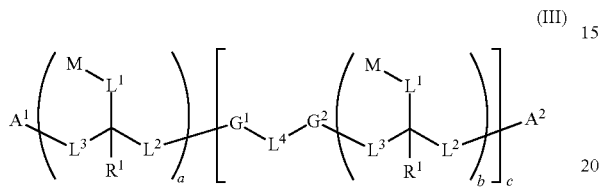

(III)

wherein:

$A^1$ and $A^2$ are each independently H, OH, SH, alkyl, alkoxy, alkylthio, alkylether, —OP(=$R_a$)($R_b$)$R_c$, Q, L' or a first functional group having complementary reactivity to $B^1$, $B^2$ or both, wherein: $R_a$ is O or S; $R_b$ is OH, SH, O⁻, S⁻, $OR_d$ or $SR_d$; $R_c$ is OH, SH, O⁻, S⁻, $OR_d$, $SR_d$, OL', $SR_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether; and $R_d$ is a counter ion;

$G^1$ and $G^2$ are each independently moieties comprising functional groups resulting from reaction of the first functional group with $B^1$ or $B^2$, respectively;

M is, at each occurrence, independently a fluorescent or colored dye moiety or Q, provided at least one occurrence of M is a fluorescent or colored dye moiety for at least one integral value of a and b;

$R^1$ is, at each occurrence, independently H, alkyl or alkoxy;

Q is, at each occurrence, independently a moiety comprising a reactive group, or protected analogue thereof, capable of forming a covalent bond with an analyte molecule, a targeting moiety, a solid support or a complementary reactive group Q';

L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (III);

$L^1$, $L^2$ and $L^3$ are, at each occurrence, independently optional bivalent linker moieties;

$L^4$ is an optional multivalent linker moiety; and a, b and c are independently an integer of 1 or greater.

In other embodiments of structure (III):

$A^1$ and $A^2$ are each independently H, OH, SH, alkyl, alkoxy, alkylthio, alkylether, —OP(=$R_a$)($R_b$)$R_c$, Q, a linker comprising a covalent bond to Q, a linker comprising a covalent bond to an analyte molecule, a linker comprising a covalent bond to a solid support, a linker comprising a covalent bond to a further compound of structure (III) or a first functional group having complementary reactivity to $B^1$, $B^2$ or both, wherein: $R_a$ is O or S; $R_b$ is OH, SH, O⁻, S⁻, $OR_d$ or $SR_d$; $R_c$ is OH, SH, O⁻, S⁻, $OR_d$, $SR_d$, alkyl, alkoxy, alkylether, alkoxyalkylether, phosphate, thiophosphate, phosphoalkyl, thiophosphoalkyl, phosphoalkylether or thiophosphoalkylether; and $R_d$ is a counter ion;

$G^1$ and $G^2$ are each independently moieties comprising functional groups resulting from reaction of the first functional group with $B^1$ or $B^2$, respectively;

M is, at each occurrence, independently a fluorescent or colored dye moiety or Q, provided at least one occurrence of M is a fluorescent or colored dye moiety for at least one integral value of a and b;

$R^1$ is, at each occurrence, independently H, alkyl or alkoxy;

$L^1$, $L^2$ and $L^3$ are, at each occurrence, independently optional bivalent linker moieties;

$L^4$ is an optional multivalent linker moiety; and a, b and c are independently an integer of 1 or greater.

In different embodiments of Method 1, $A^1$ and $A^2$ are each independently a first functional group having complementary reactivity to $B^1$, $B^2$ or both. For example, in some embodiments $A^1$, $A^2$ are each independently a nucleophilic functional group. The nucleophilic functional group can, in some embodiments, be amino, alkylamino, sulfhydryl or hydroxyl.

In other embodiments of Method 1, $B^1$ and $B^2$ are each independently an electrophilic functional group. In some embodiments the electrophilic functional group is an acid halide, N-hydroxysuccinimide ester, isocycanate, isothiocyanate, epoxide, halide, tosylate, mesylate, triflate, maleimide, phosphate or alkene.

In some different embodiments of Method 1, $A^1$, $A^2$ are each independently an electrophilic functional group. For example, in some embodiments the electrophilic functional group is an N-hydroxysuccinimide ester, phenolate ester, halide, tosylate, mesylate, phosphate or triflate.

In other different embodiments of Method 1, $B^1$ and $B^2$ are each independently nucleophilic functional group. In certain embodiments, the nucleophilic functional group is amino, alkylamino, sulfhydryl or hydroxyl.

In yet more embodiments of Method 1, $A^1$, $A^2$, $B^1$ and $B^2$ are each independently nucleic acid sequences, and $A^1$ is complementary to $B^1$, and $A^2$ is complementary to $B^2$.

In some more embodiments of Method 1, $A^1$ and $A^2$ are each independently an alkyne and $B^1$ and $B^2$ are each independently an azide.

In other embodiments of Method 1, $A^1$ and $A^2$ are each independently an azide and $B^1$ and $B^2$ are each independently an alkyne.

In still more embodiments of Method 1, at least one of $A^1$ and $A^2$ comprises a cycloaddition reactive functional group, and each of $B^1$ and $B^2$ are complementary cycloaddition reactive functional groups. For example, in some embodiments each cycloaddition reactive functional group comprises an alkene.

In more embodiments of Method 1, $A^1$ and $A^2$ comprise an aryl halide, and each of $B^1$ and $B^2$ are alkene or alkyne functional groups.

In other different embodiments of Method 1, $A^1$ and $A^2$ comprise a boronic acid or boronic ester, and each of $B^1$ and $B^2$ are aryl halide or alkyl halide functional groups.

In some embodiments of Method 1, $A^1$ and $A^2$ comprise an alkylstannane or arylstannane, and each of $B^1$ and $B^2$ are aryl halide or alkyl halide functional groups.

In some other different embodiments of Method 1, $A^1$ and $A^2$ comprise an amine, and each of $B^1$ and $B^2$ are aryl halide or alkyl halide functional groups.

In still other different embodiments, $G^1$ and $G^2$ each independently comprise an amide, urea, carbamate, urethane, thiocarbamate, amino-alcohol, thioether-alcohol, ether-alcohol, amine, thioether, thioester, double-stranded nucleic acid, phosphodiester, alkene, alkyne or a triazole.

In any of the foregoing embodiments of Method 1, $L^4$ is alkylene.

In other of any of the foregoing embodiments of Method 1, $L^3$, at each occurrence, independently has the following structure:

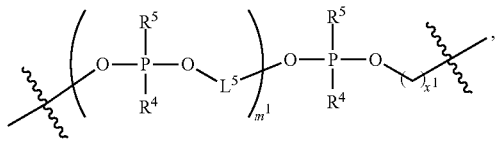

wherein:
$R^4$ is, at each occurrence, independently OH, SH, O⁻, S⁻, $OR_d$ or $SR_d$;
$R^5$ is, at each occurrence, independently oxo, thioxo or absent;
$m^1$ and $x^1$ are, at each occurrence, independently an integer from 0 to 10; and
$L^5$ is an alkylene, alkenylene, alkynylene, heteroalkylene, heteroalkenylene, heteroalkynylene, carbocyclic or heterocyclic linker. For example, in some embodiments heteroalkylene is alkylene oxide, such as a polyethylene oxide.

In other embodiments of Method 1, $L^3$ is, at each occurrence, independently an amino acid or peptide linker.

In more embodiments of Method 1, $L^3$ is, at each occurrence, independently a linker comprising one or more charged moieties.

In another aspect, the invention provides a method ("Method 2") for preparing a dimeric or polymeric dye, the method comprising reacting a first compound of structure (I):

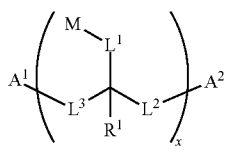

with a second compound of structure (I), wherein:
$A^1$ is H, OH, SH, alkyl, alkoxy, alkylthio, alkylether, —OP(=$R_a$)($R_b$)$R_c$, Q, L' or a moiety comprising a first functional group having complementary reactivity to a second functional group, wherein: $R_a$ is O or S; $R_b$ is OH, SH, O⁻, S⁻, $OR_d$ or $SR_d$; $R_c$ is OH, SH, O⁻, S⁻, $OR_d$, OL', $SR_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether; and $R_d$ is a counter ion;
$A^2$ is a moiety comprising the second functional group, wherein the second functional group has reactivity complementary to itself or reactivity complementary to the first functional group;
M is, at each occurrence, independently a fluorescent or colored dye moiety or Q, provided at least one occurrence of M is a fluorescent or colored dye moiety;
$R^1$ is, at each occurrence, independently H, alkyl or alkoxy;
Q is, at each occurrence, independently a moiety comprising a reactive group, or protected analogue thereof, capable of forming a covalent bond with an analyte molecule, a targeting moiety, a solid support or a complementary reactive group Q';
L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (I);
$L^1$, $L^2$ and $L^3$ are, at each occurrence, independently optional bivalent linker moieties; and
x is an integer of 1 or greater,
thereby forming a bond between the first and second compounds of structure (I) by reaction of: i) the first functional group on the first compound of structure (I) and the second functional group on the second compound of structure (I); or ii) the second functional group on the first compound of structure (I) and the second functional group on the second compound of structure (I).

In other embodiments of Method 2:
$A^1$ is H, OH, SH, alkyl, alkoxy, alkylthio, alkylether, —OP(=$R_a$)($R_b$)$R_c$, Q, a linker comprising a covalent bond to Q, a linker comprising a covalent bond to an analyte molecule, a linker comprising a covalent bond to a solid support, a linker comprising a covalent bond to a further compound of structure (I) or a moiety comprising a first functional group having complementary reactivity to a second functional group, wherein: $R_a$ is O or S; $R_b$ is OH, SH, O⁻, S⁻, $OR_d$ or $SR_d$; $R_c$ is OH, SH, O⁻, S⁻, $OR_d$, $SR_d$, alkyl, alkoxy, alkylether, alkoxyalkylether, phosphate, thiophosphate, phosphoalkyl, thiophosphoalkyl, phosphoalkylether or thiophosphoalkylether; and $R_d$ is a counter ion;
$A^2$ is a moiety comprising the second functional group, wherein the second functional group has reactivity complementary to itself or reactivity complementary to the first functional group;
M is, at each occurrence, independently a fluorescent or colored dye moiety or Q, provided at least one occurrence of M is a fluorescent or colored dye moiety;
$R^1$ is, at each occurrence, independently H, alkyl or alkoxy;
$L^1$, $L^2$ and $L^3$ are, at each occurrence, independently optional bivalent linker moieties; and
x is an integer of 1 or greater,
thereby forming a bond between the first and second compounds of structure (I) by reaction of: i) the first functional group on the first compound of structure (I) and the second functional group on the second compound of structure (I); or ii) the second functional group on the first compound of structure (I) and the second functional group on the second compound of structure (I).

In some embodiments of Method 2, the bond is formed between the first and second compounds of structure (I) by reaction of the first functional group on the first compound of structure (I) and the second functional group on the second compound of structure (I). For example, in some embodiments the dimeric or polymeric dye has the following structure (IV):

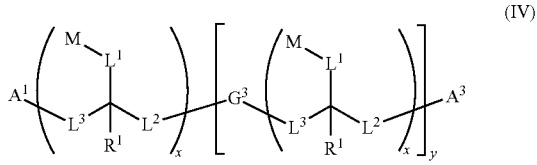

wherein:
- $A^1$ is H, OH, SH, alkyl, alkoxy, alkylthio, alkylether, —OP(=$R_a$)($R_b$)$R_c$, Q, L' or a moiety comprising a first functional group having complementary reactivity to a second functional group, wherein: $R_a$ is O or S; $R_b$ is OH, SH, O⁻, S⁻, $OR_d$ or $SR_d$; $R_c$ is OH, SH, O⁻, S⁻, $OR_d$, OL', $SR_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether; and $R_d$ is a counter ion;
- $A^3$ is H, OH, SH, alkyl, alkoxy, alkylthio, alkylether, —OP(=$R_a$)($R_b$)$R_c$, Q, a linker comprising a covalent bond to Q, a linker comprising a covalent bond to an analyte molecule, a linker comprising a covalent bond to a solid support, a linker comprising a covalent bond to a further compound of structure (I) or a moiety comprising the second functional group, wherein: $R_a$ is O or S; $R_b$ is OH, SH, O⁻, S⁻, $OR_d$ or $SR_d$; $R_c$ is OH, SH,
  O⁻, S⁻, $OR_d$, $SR_d$, alkyl, alkoxy, alkylether, alkoxyalkylether, phosphate, thiophosphate, phosphoalkyl, thiophosphoalkyl, phosphoalkylether or thiophosphoalkylether; and $R_d$ is a counter ion;
- $G^3$ is a moiety comprising a functional group resulting from reaction of the first functional group with the second functional group;
- M is, at each occurrence, independently a fluorescent or colored dye moiety or Q, provided at least one occurrence of M is a fluorescent or colored dye moiety;
- $R^1$ is, at each occurrence, independently H, alkyl or alkoxy;
- Q is, at each occurrence, independently a moiety comprising a reactive group, or protected analogue thereof, capable of forming a covalent bond with an analyte molecule, a targeting moiety, a solid support or a complementary reactive group Q';
- L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (IV);
- $L^1$, $L^2$ and $L^3$ are, at each occurrence, independently optional bivalent linker moieties; and
- each x is independently an integer of 1 or greater; and y is an integer of 1 or greater.

In other embodiments of structure (IV):
- $A^1$ is H, OH, SH, alkyl, alkoxy, alkylthio, alkylether, —OP(=$R_a$)($R_b$)$R_c$, Q, a linker comprising a covalent bond to Q, a linker comprising a covalent bond to an analyte molecule, a linker comprising a covalent bond to a solid support, a linker comprising a covalent bond to a further compound of structure (IV) or a moiety comprising a first functional group having complementary reactivity to a second functional group, wherein: $R_a$ is O or S; $R_b$ is OH, SH, O⁻, S⁻, $OR_d$ or $SR_d$; $R_c$ is OH, SH, O⁻, S⁻, $OR_d$, $SR_d$, alkyl, alkoxy, alkylether, alkoxyalkylether, phosphate, thiophosphate, phosphoalkyl, thiophosphoalkyl, phosphoalkylether or thiophosphoalkylether; and $R_d$ is a counter ion;
- $A^3$ is H, OH, SH, alkyl, alkoxy, alkylthio, alkylether, —OP(=$R_a$)($R_b$)$R_c$, Q, a linker comprising a covalent bond to Q, a linker comprising a covalent bond to an analyte molecule, a linker comprising a covalent bond to a solid support, a linker comprising a covalent bond to a further compound of structure (I) or a moiety comprising the second functional group, wherein: $R_a$ is O or S; $R_b$ is OH, SH, O⁻, S⁻, $OR_d$ or $SR_d$; $R_c$ is OH, SH,
  O⁻, S⁻, $OR_d$, $SR_d$, alkyl, alkoxy, alkylether, alkoxyalkylether, phosphate, thiophosphate, phosphoalkyl, thiophosphoalkyl, phosphoalkylether or thiophosphoalkylether; and $R_d$ is a counter ion;
- $G^3$ is a moiety comprising a functional group resulting from reaction of the first functional group with the second functional group;
- M is, at each occurrence, independently a fluorescent or colored dye moiety or Q, provided at least one occurrence of M is a fluorescent or colored dye moiety;
- $R^1$ is, at each occurrence, independently H, alkyl or alkoxy;
- $L^1$, $L^2$ and $L^3$ are, at each occurrence, independently optional bivalent linker moieties; and
- each x is independently an integer of 1 or greater; and y is an integer of 1 or greater.

In any of the foregoing embodiments of Method 1 or Method 2, $A^1$, $A^2$ an $A^3$ are independently selected from a moiety comprising a functional groups for use in a reaction selected from amine/carboxylate condensation, 3+2 cycloaddition and other cycloaddition reactions, ring opening metathesis, olefin cross metathesis, Staudinger reaction, aromatic diazonium reactions; thiol-ene reaction; Diels-Alder reaction, Hydrazine/Hydrazide/Hydroxylamine condensation to carbonyls; Sonogashira reaction, Heck coupling, Suzuki coupling, Stille coupling, Glaser coupling and Amine/epoxide ring opening. Such functional groups will be apparent to one of ordinary skill in the art.

In different embodiment of Method 2, the first functional group is a nucleophilic functional group. For example, the nucleophilic functional group may be amino, alkylamino, sulfhydryl or hydroxyl in various embodiments.

In other embodiments of Method 2, the second functional group is an electrophilic functional group. For example, the electrophilic functional group may be an acid halide, N-hydroxysuccinimide ester, isocyanate, isothiocyanate, epoxide, halide, tosylate, mesylate, triflate, maleimide, phosphate or alkene in various embodiments.

In other embodiments of Method 2, the first and second functional groups are each independently nucleic acid sequences, and the first functional group is complementary to the second functional group.

In different embodiments of Method 2, the first functional group is an alkyne and the second functional group is an azide.

In some other embodiments of Method 2, the first functional group is a cycloaddition reactive functional group, and the second functional group is a complementary cycloaddition reactive functional group.

In other embodiments of Method 2, the first functional group is an aryl halide, and the second functional group is an alkene or alkyne functional group.

In still more embodiments of Method 2, the first functional group is a boronic acid or boronic ester, and the second functional group is an aryl halide or alkyl halide functional group.

In yet more embodiments of Method 2, the first functional group is an alkylstannane or arylstannane, and the second functional group is an aryl halide or alkyl halide functional group.

In some other different embodiments of Method 2, the first functional group is an amine, and the second functional group is an aryl halide or alkyl halide functional group.

In some embodiments of Method 2, $G^3$ comprises an amide, urea, carbamate, urethane, thiocarbamate, aminoalcohol, thioether-alcohol, ether-alcohol, amine, thioether, thioester, double-stranded nucleic acid, phosphodiester, alkene, alkyne or a triazole.

In any of the foregoing embodiments of Method 2, $L^3$, at each occurrence, independently has the following structure:

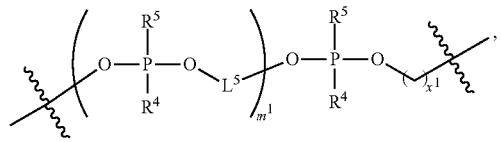

wherein:
$R^4$ is, at each occurrence, independently OH, SH, O$^-$, S$^-$, OR$_d$ or SR$_d$;

$R^5$ is, at each occurrence, independently oxo, thioxo or absent;

$m^1$ and $x^1$ are, at each occurrence, independently an integer from 0 to 10; and $L^5$ is an alkylene, alkenylene, alkynylene, heteroalkylene, heteroalkenylene, heteroalkynylene, carbocyclic or heterocyclic linker. For example, in some embodiments heteroalkylene is alkylene oxide, such as a polyethylene oxide.

In other of the foregoing embodiments of Method 2, $L^3$ is, at each occurrence, independently an amino acid or peptide linker.

In still other of the foregoing embodiments of Method 2, $L^3$ is, at each occurrence, independently a linker comprising one or more charged moieties.

In other embodiments of Method 2, the bond is formed between the first and second compounds of structure (I) by reaction of the second functional group on the first compound of structure (I) and the functional group on the second compound of structure (I).

In some other specific embodiments of Method 2, the dimeric or polymeric dye has the following structure (V):

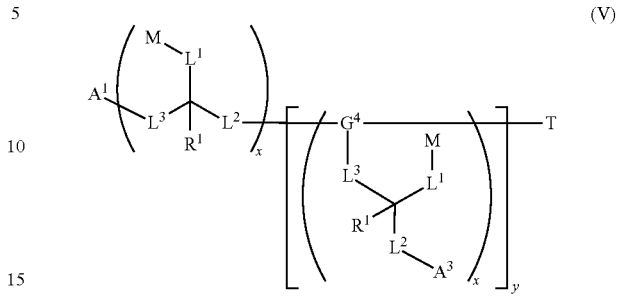

wherein:
$A^1$ is H, OH, SH, alkyl, alkoxy, alkylthio, alkylether, —OP(=R$_a$)(R$_b$)R$_c$, Q, L' or a moiety comprising a first functional group having complementary reactivity to a second functional group, wherein: R$_a$ is O or S; R$_b$ is OH, SH, O$^-$, S$^-$, OR$_d$ or SR$_d$; R$_c$ is OH, SH, O$^-$, S$^-$, OR$_d$, OL', SR$_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether; and R$_d$ is a counter ion;

T is absent or a polymer terminating group;

$G^4$ is a moiety comprising a functional group resulting from reaction of the second functional group on the first compound of structure (I) and the second functional group on the second compound of structure (I);

M is, at each occurrence, independently a fluorescent or colored dye moiety or Q, provided at least one occurrence of M is a fluorescent or colored dye moiety;

$R^1$ is, at each occurrence, independently H, alkyl or alkoxy;

Q is, at each occurrence, independently a moiety comprising a reactive group, or protected analogue thereof, capable of forming a covalent bond with an analyte molecule, a targeting moiety, a solid support or a complementary reactive group Q';

L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (V);

$L^1$, $L^2$ and $L^3$ are, at each occurrence, independently optional bivalent linker moieties; and each x is independently an integer of 1 or greater; and y is an integer of 1 or greater.

In other embodiments of structure (V):
$A^1$ is H, OH, SH, alkyl, alkoxy, alkylthio, alkylether, —OP(=R$_a$)(R$_b$)R$_c$, Q, a linker comprising a covalent bond to Q, a linker comprising a covalent bond to an analyte molecule, a linker comprising a covalent bond to a solid support, a linker comprising a covalent bond to a further compound of structure (V) or a moiety comprising a first functional group having complementary reactivity to a second functional group, wherein: R$_a$ is O or S; R$_b$ is OH, SH, O$^-$, S$^-$, OR$_d$ or SR$_d$; R$_c$ is OH, SH, O$^-$, S$^-$, OR$_d$, SR$_d$, alkyl, alkoxy, alkylether, alkoxyalkylether, phosphate, thiophosphate, phosphoalkyl, thiophosphoalkyl, phosphoalkylether or thiophosphoalkylether; and $R_d$ is a counter ion;

T is absent or a polymer terminating group;

$G^4$ is a moiety comprising a functional group resulting from reaction of the second functional group on the first compound of structure (I) and the second functional group on the second compound of structure (I);

M is, at each occurrence, independently a fluorescent or colored dye moiety or Q, provided at least one occurrence of M is a fluorescent or colored dye moiety;

$R^1$ is, at each occurrence, independently H, alkyl or alkoxy;

$L^1$, $L^2$ and $L^3$ are, at each occurrence, independently optional bivalent linker moieties; and each x is independently an integer of 1 or greater; and y is an integer of 1 or greater.

For example, in some embodiments of Method 2, each second functional group is a cycloaddition reactive functional group. In other embodiments, each second functional group is an acrylate functional group.

In some different embodiments, the invention provides compounds. The compounds can be prepared according to the foregoing methods or other methods known in the art. For example, in some embodiments is provided a compound having one of the following structures (III), (IV) or (V):

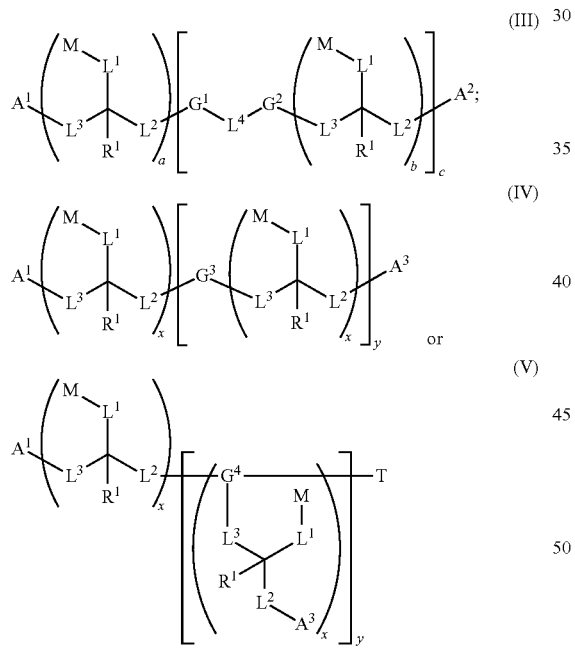

wherein:

$A^1$, $A^2$ and $A^3$ are each independently H, OH, SH, alkyl, alkoxy, alkylthio, alkylether, —OP($=R_a$)($R_b$)$R_c$, Q, L' or a moiety comprising a functional group capable of forming $G^1$, $G^2$, $G^3$ or $G^4$ upon reaction with a moiety comprising complementary functional group, wherein: $R_a$ is O or S; $R_b$ is OH, SH, O⁻, S⁻, O$R_d$, OL', S$R_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether; and $R_d$ is a counter ion;

$G^1$, $G^2$, $G^3$ and $G^4$ are each independently moieties comprising a urea, carbamate, urethane, thiocarbamate, amino-alcohol, thioether-alcohol, ether-alcohol, amine, thioether, thioester, double-stranded nucleic acid, alkene, alkyne or triazole functional group;

T is absent or a polymer terminating group;

M is, at each occurrence, independently a fluorescent or colored dye moiety or Q, provided at least one occurrence of M is a fluorescent or colored dye moiety for at least one integral value of a and b;

$R^1$ is, at each occurrence, independently H, alkyl or alkoxy;

Q is, at each occurrence, independently a moiety comprising a reactive group, or protected analogue thereof, capable of forming a covalent bond with an analyte molecule, a targeting moiety, a solid support or a complementary reactive group Q';

L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (I);

$L^1$, $L^2$ and $L^3$ are, at each occurrence, independently optional bivalent linker moieties;

$L^4$ is an optional multivalent linker moiety;

a, b and c are independently an integer of 1 or greater;

each x is independently an integer of 1 or greater; and y is an integer of 1 or greater.

In other embodiments of structures (III), (IV) or (V):

$A^1$, $A^2$ and $A^3$ are each independently H, OH, SH, alkyl, alkoxy, alkylthio, alkylether, —OP($=R_a$)($R_b$)$R_c$, Q, a linker comprising a covalent bond to Q, a linker comprising a covalent bond to an analyte molecule, a linker comprising a covalent bond to a solid support, a linker comprising a covalent bond to a further compound of structure (III), (IV) or (V) or a moiety comprising a functional group capable of forming $G^1$, $G^2$, $G^3$ or $G^4$ upon reaction with a moiety comprising complementary functional group, wherein: $R_a$ is O or S; $R_b$ is OH, SH, O⁻, S⁻, O$R_d$ or S$R_d$; $R_c$ is OH, SH, O⁻, S⁻, O$R_d$, S$R_d$, alkyl, alkoxy, alkylether, alkoxyalkylether, phosphate, thiophosphate, phosphoalkyl, thiophosphoalkyl, phosphoalkylether or thiophosphoalkylether; and $R_d$ is a counter ion;

$G^1$, $G^2$, $G^3$ and $G^4$ are each independently moieties comprising a urea, carbamate, urethane, thiocarbamate, amino-alcohol, thioether-alcohol, ether-alcohol, amine, thioether, thioester, double-stranded nucleic acid, alkene, alkyne or triazole functional group;

T is absent or a polymer terminating group;

M is, at each occurrence, independently a fluorescent or colored dye moiety or Q, provided at least one occurrence of M is a fluorescent or colored dye moiety for at least one integral value of a and b;

$R^1$ is, at each occurrence, independently H, alkyl or alkoxy;

$L^1$, $L^2$ and $L^3$ are, at each occurrence, independently optional bivalent linker moieties;

$L^4$ is an optional multivalent linker moiety;

a, b and c are independently an integer of 1 or greater;

each x is independently an integer of 1 or greater; and y is an integer of 1 or greater.

In some embodiments of the foregoing compounds, $L^4$ is alkylene.

In other embodiments of the foregoing compounds $L^3$, at each occurrence, independently has the following structure:

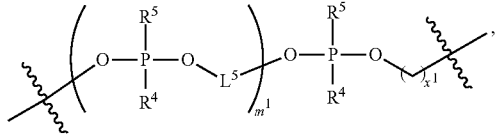

wherein:
$R^4$ is, at each occurrence, independently OH, SH, O$^-$, S$^-$, OR$_d$ or SR$_d$;
$R^5$ is, at each occurrence, independently oxo, thioxo or absent;
$m^1$ and $x^1$ are, at each occurrence, independently an integer from 0 to 10; and
$L^5$ is an alkylene, alkenylene, alkynylene, heteroalkylene, heteroalkenylene, heteroalkynylene, carbocyclic or heterocyclic linker. For example, in some embodiments heteroalkylene is alkylene oxide, such as a polyethylene oxide.

In some embodiments of the foregoing compounds, $L^3$ is, at each occurrence, independently an amino acid or peptide linker.

In some other embodiments of the foregoing compounds $L^3$ is, at each occurrence, independently a linker comprising one or more charged moieties.

In other embodiments of the compounds, $R^1$ is H.

In still different embodiments of the compounds, $A^1$, $A^2$ and $A^3$ are each independently OH or —OP(=R$_a$)(R$_b$)R$_c$.

M is selected based on the desired optical properties, for example based on a desired color and/or fluorescence emission wavelength. In some embodiments, M is the same at each occurrence; however, it is important to note that each occurrence of M need not be an identical M, and certain embodiments include compounds wherein M is not the same at each occurrence. For example, in some embodiments each M is not the same and the different M moieties are selected to have absorbance and/or emissions for use in fluorescence resonance energy transfer (FRET) methods. For example, in such embodiments the different M moieties are selected such that absorbance of radiation at one wavelength causes emission of radiation at a different wavelength by a FRET mechanism. Exemplary M moieties can be appropriately selected by one of ordinary skill in the art based on the desired end use. Exemplary M moieties for FRET methods include fluorescein and 5-TAMRA (5-carboxytetramethylrhodamine, succinimidyl ester) dyes.

M may be attached to the remainder of the molecule from any position (i.e., atom) on M. One of skill in the art will recognize means for attaching M to the remainder of molecule. Exemplary methods include the "click" reactions described herein.

In some embodiments, M is a fluorescent or colored moiety. Any fluorescent and/or colored moiety may be used, for examples those known in the art and typically employed in colorimetric, UV, and/or fluorescent assays may be used. Examples of M moieties which are useful in various embodiments of the invention include, but are not limited to: Xanthene derivatives (e.g., fluorescein, rhodamine, Oregon green, eosin or Texas red); Cyanine derivatives (e.g., cyanine, indocarbocyanine, oxacarbocyanine, thiacarbocyanine or merocyanine); Squaraine derivatives and ring-substituted squaraines, including Seta, SeTau, and Square dyes; Naphthalene derivatives (e.g., dansyl and prodan derivatives); Coumarin derivatives; oxadiazole derivatives (e.g., pyridyloxazole, nitrobenzoxadiazole or benzoxadiazole); Anthracene derivatives (e.g., anthraquinones, including DRAQ5, DRAQ7 and CyTRAK Orange); Pyrene derivatives such as cascade blue; Oxazine derivatives (e.g., Nile red, Nile blue, cresyl violet, oxazine 170); Acridine derivatives (e.g., proflavin, acridine orange, acridine yellow); Arylmethine derivatives: auramine, crystal violet, malachite green; and Tetrapyrrole derivatives (e.g., porphin, phthalocyanine or bilirubin). Other exemplary M moieties include: Cyanine dyes, xanthate dyes (e.g., Hex, Vic, Nedd, Joe or Tet); Yakima yellow; Redmond red; tamra; texas red and Alexa Fluor® dyes.

In still other embodiments of any of the foregoing, M comprises three or more aryl or heteroaryl rings, or combinations thereof, for example four or more aryl or heteroaryl rings, or combinations thereof, or even five or more aryl or heteroaryl rings, or combinations thereof. In some embodiments, M comprises six aryl or heteroaryl rings, or combinations thereof. In further embodiments, the rings are fused. For example in some embodiments, M comprises three or more fused rings, four or more fused rings, five or more fused rings, or even six or more fused rings.

In some embodiments, M is cyclic. For example, in some embodiments M is carbocyclic. In other embodiment, M is heterocyclic. In still other embodiments of the foregoing, M, at each occurrence, independently comprises an aryl moiety. In some of these embodiments, the aryl moiety is multicyclic. In other more specific examples, the aryl moiety is a fused-multicyclic aryl moiety, for example which may comprise at least 3, at least 4, or even more than 4 aryl rings.

In other embodiments of any of the foregoing methods or compounds, M, at each occurrence, independently comprises at least one heteroatom. For example, in some embodiments, the heteroatom is nitrogen, oxygen or sulfur.

In still more embodiments of any of the foregoing, M, at each occurrence, independently comprises at least one substituent. For example, in some embodiments the substituent is a fluoro, chloro, bromo, iodo, amino, alkylamino, arylamino, hydroxy, sulfhydryl, alkoxy, aryloxy, phenyl, aryl, methyl, ethyl, propyl, butyl, isopropyl, t-butyl, carboxy, sulfonate, amide, or formyl group.

In some even more specific embodiments of the foregoing, M, at each occurrence, independently is a dimethylaminostilbene, quinacridone, fluorophenyl-dimethyl-BODIPY, his-fluorophenyl-BODIPY, acridine, terrylene, sexiphenyl, porphyrin, benzopyrene, (fluorophenyl-dimethyl-difluorobora-diaza-indacene)phenyl, (bis-fluorophenyl-difluorobora-diaza-indacene)phenyl, quaterphenyl, bi-benzothiazole, ter-benzothiazole, bi-naphthyl, bi-anthracyl, squaraine, squarylium, 9, 10-ethynylanthracene or ter-naphthyl moiety. In other embodiments, M is, at each occurrence, independently p-terphenyl, perylene, azobenzene, phenazine, phenanthroline, acridine, thioxanthrene, chrysene, rubrene, coronene, cyanine, perylene imide, or perylene amide or a derivative thereof. In still more embodiments, M is, at each occurrence, independently a coumarin dye, resorufin dye, dipyrromethenboron difluoride dye, ruthenium bipyridyl dye, energy transfer dye, thiazole orange dye, polymethine or N-aryl-1,8-naphthalimide dye.

In still more embodiments of any of the foregoing, M at each occurrence is the same. In other embodiments, each M is different. In still more embodiments, one or more M is the same and one or more M is different.

In some embodiments, M is pyrene, perylene, perylene monoimide or 6-FAM or a derivative thereof. In some other embodiments, M has one of the following structures:

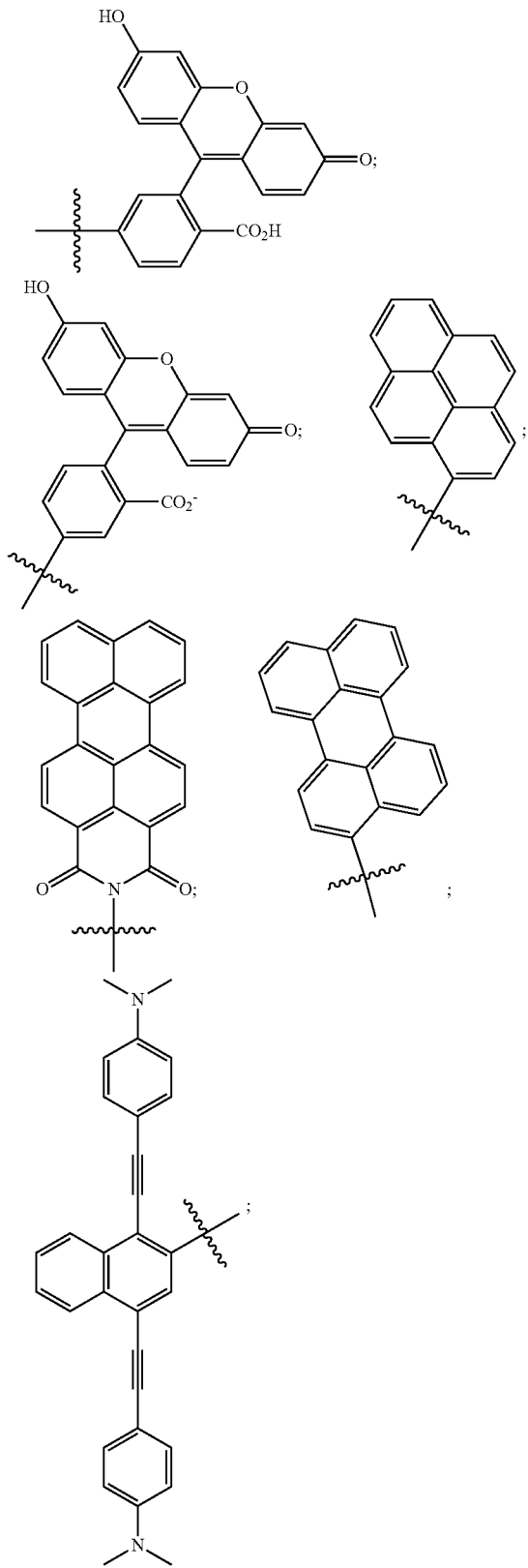

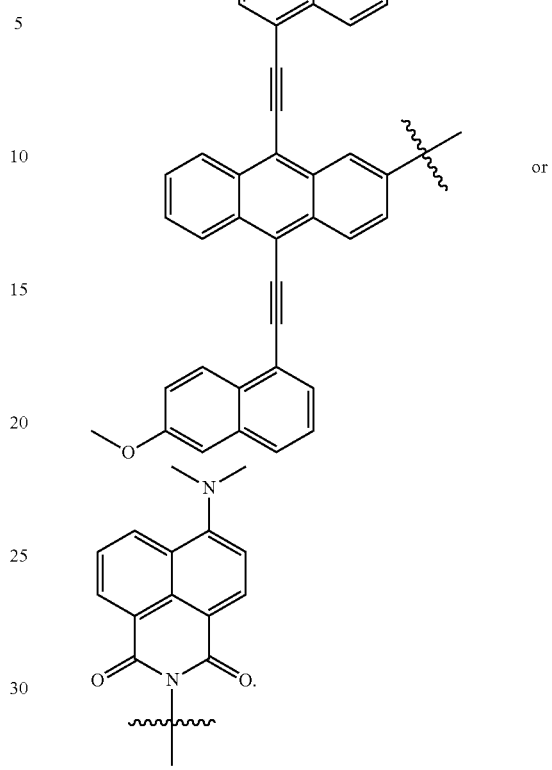

Although M moieties comprising carboxylic acid groups are depicted in the anionic form ($CO_2^-$) above, one of skill in the art will understand that this will vary depending on pH, and the protonated form ($CO_2H$) is included in various embodiments.

In still other embodiments of any of the foregoing methods or compounds, Q is, at each occurrence, independently a moiety comprising a reactive group capable of forming a covalent bond with an analyte molecule or a solid support. In other embodiments, Q is, at each occurrence, independently a moiety comprising a reactive group capable of forming a covalent bond with a complementary reactive group Q'.

The type of Q group and connectivity of the Q group to the remainder of the compound is not limited, provided that Q comprises a moiety having appropriate reactivity for forming the desired bond.

In certain embodiments, Q is a moiety which is not susceptible to hydrolysis under aqueous conditions, but is sufficiently reactive to form a bond with a corresponding group on an analyte molecule or solid support (e.g., an amine, azide or alkyne).

In certain embodiments of the methods and compounds, Q comprises groups commonly employed in the field of bioconjugation. For example in some embodiments, Q comprises a nucleophilic reactive group, an electrophilic reactive group or a cycloaddition reactive group. In some more specific embodiments, Q comprises a sulfhydryl, disulfide, activated ester, isothiocyanate, azide, alkyne, alkene, diene, dienophile, acid halide, sulfonyl halide, phosphine, α-halo-amide, biotin, amino or maleimide functional group. In some embodiments, the activated ester is an N-succinimide ester, imidoester or polyflourophenyl ester. In other embodiments, the alkyne is an alkyl azide or acyl azide.

The Q groups can be conveniently provided in protected form to increase storage stability or other desired properties, and then the protecting group removed at the appropriate time for conjugation with, for example, a targeting moiety or analyte. Accordingly, Q groups include "protected forms" of a reactive group, including any of the reactive groups described above and in the Table 1 below. A "protected form" of Q refers to a moiety having lower reactivity under predetermined reaction conditions relative to Q, but which can be converted to Q under conditions, which preferably do not degrade or react with other portions of the compound of structure (I). One of skill in the art can derive appropriate protected forms of Q based on the particular Q and desired end use and storage conditions. For example, when Q is SH, a protected form of Q includes a disulfide, which can be reduce to reveal the SH moiety using commonly known techniques and reagents.

Exemplary Q moieties are provided in Table I below.

TABLE 1

| Exemplary Q Moieties | |
|---|---|
| Structure | Class |
| 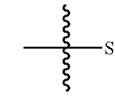 | Sulfhydryl |
| | Isothiocyanate |
| | Imidoester |
| | Acyl Azide |
| | Activated Ester |
| | Activated Ester |

TABLE 1-continued

| Exemplary Q Moieties | |
|---|---|
| Structure | Class |
| 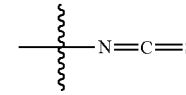 | Activated Ester |
| | Activated Ester |
| | Activated Ester |
| | Activated Ester |
| | Sulfonyl halide |
| X = halo | |
| 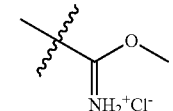 | Maleimide |
| | Maleimide |
| | Maleimide |
| | α-haloimide |

TABLE 1-continued

Exemplary Q Moieties

| Structure | Class |
|---|---|
| X = halo | Disulfide |
| (pyridyl disulfide structure) | Disulfide |
| (methyl benzoate with diphenylphosphine and ketone) | Phosphine |
| —N₃ | Azide |
| (alkyne) | Alkyne |
| (biotin structure) | Biotin |
| (diene structure) | Diene |
| (alkene) | Alkene/dienophile |
| (alkene)—EWG | Alkene/dienophile |
| EWG = eletron withdrawing group | |
| —NH₂ | Amino |

It should be noted that in some embodiments, wherein Q is SH, the SH moiety will tend to form disulfide bonds with another sulfhydryl group on another compound. Accordingly, some embodiments include the foregoing compounds, which are in the form of disulfide dimers, the disulfide bond being derived from SH Q groups.

In some specific embodiments, the compound is a compound selected from Table 2 and/or compounds prepared therefrom (e.g., Compounds 1, 1', 1", 2, 3, 3', 4, 4', 5 and 5').

The compounds in Table 2 were prepared according to the procedures set forth in the Examples.

The presently disclosed dye compounds are "tunable," meaning that by proper selection of the variables (e.g., M, a, b, c, x, y, $m^1$ and/or L4) in any of the foregoing compounds, one of skill in the art can arrive at a compound having a desired and/or predetermined molar fluorescence (molar brightness). The tunability of the compounds allows the user to easily arrive at compounds having the desired fluorescence and/or color for use in a particular assay or for identifying a specific analyte of interest. Molar fluorescence in certain embodiments can be expressed in terms of the fold increase or decrease relative to the fluorescence emission of the parent fluorophore (e.g., monomer). In some embodiments the molar fluorescence of the present compounds is 1.1×, 1.5×, 2×, 3×, 4×, 5×, 6×, 7×, 8×, 9× 10× or even higher relative to the parent fluorophore.

For ease of illustration, various compounds comprising phosphorous moieties (e.g., phosphate and the like) are depicted in the anionic state (e.g., —OPO(OH)O⁻, —OPO₃²⁻). One of skill in the art will readily understand that the charge is dependent on pH and the uncharged (e.g., protonated or salt, such as sodium or other cation) forms are also included in the scope of embodiments of the invention.

Compositions comprising any of the foregoing compounds and one or more analyte molecules (e.g., biomolecules) are provided in various other embodiments. In some embodiments, use of such compositions in analytical methods for detection of the one or more analyte molecules are also provided.

In still other embodiments, the compounds are useful in various analytical methods. For example, in certain embodiments the disclosure provides a method of staining a sample, the method comprising adding to said sample a compound of structure (III), (IV) or (V), for example wherein one of $A^1$, $A^2$ and $A^3$ is a linker comprising a covalent bond to an analyte molecule (e.g., biomolecule) or solid support, and another one of $A^1$, $A^2$ and $A^3$ is H, OH, alkyl, alkoxy, alkylether or —OP(=$R_a$)($R_b$)$R_c$, in an amount sufficient to produce an optical response when said sample is illuminated at an appropriate wavelength.

In some embodiments of the foregoing methods, $A^1$ is a linker comprising a covalent linkage to an analyte molecule, such as a biomolecule. For example, a nucleic acid, amino acid or a polymer thereof (e.g., polynucleotide or polypeptide). In still more embodiments, the biomolecule is an enzyme, receptor, receptor ligand, antibody, glycoprotein, aptamer or prion.

In yet other embodiments of the foregoing method, $A^1$ is a linker comprising a covalent linkage to a solid support such as a microparticle. For example, in some embodiments the microparticle is a polymeric bead or nonpolymeric bead.

In even more embodiments, said optical response is a fluorescent response.

In other embodiments, said sample comprises cells, and some embodiments further comprise observing said cells by flow cytometry.

In still more embodiments, the method further comprises distinguishing the fluorescence response from that of a second fluorophore having detectably different optical properties.

In other embodiments, the disclosure provides a method for visually detecting an analyte molecule, such as a biomolecule, comprising:
(a) providing a compound of structure (III), (IV) or (V), for example, wherein one of $A^1$, $A^2$ and $A^3$ is a linker comprising a covalent bond to the analyte molecule, and the other of $A^1$, $A^2$ and $A^3$ is H, OH, alkyl, alkoxy, alkylether or $-OP(=R_a)(R_b)R_c$; and (b) detecting the compound by its visible properties.

In some embodiments the analyte molecule is a nucleic acid, amino acid or a polymer thereof (e.g., polynucleotide or polypeptide). In still more embodiments, the analyte molecule is an enzyme, receptor, receptor ligand, antibody, glycoprotein, aptamer or prion.

In other embodiments, a method for visually detecting an analyte molecule, such as a biomolecule is provided, the method comprising:

(a) admixing any of the foregoing compounds with one or more analyte molecules; and (b) detecting the compound by its visible properties.

In other embodiments is provided a method for visually detecting an analyte molecule, the method comprising:

(a) admixing a compound of structure (III), (IV) or (V), wherein $A^1$, $A^2$ or $A^3$ is Q or a linker comprising a covalent bond to Q, with the analyte molecule;

(b) forming a conjugate of the compound and the analyte molecule; and (c) detecting the conjugate by its visible properties.

Other embodiments provide a method for visually detecting an analyte, the method comprising:

(a) providing a compound of structure (III), (IV) or (V), wherein $A^1$ or $A^2$ comprises a linker comprising a covalent bond to a targeting moiety having specificity for the analyte;

(b) admixing the compound and the analyte, thereby associating the targeting moiety and the analyte; and (c) detecting the compound by its visible properties.

In addition to the above methods, embodiments of the disclosed compounds (e.g., compounds of structure (III), (IV) or (V)) find utility in various disciplines and methods, including but not limited to: imaging in endoscopy procedures for identification of cancerous and other tissues; single-cell and/or single molecule analytical methods, for example detection of polynucleotides with little or no amplification; cancer imaging, for example by conjugating a disclosed compound to an antibody or sugar or other moiety that preferentially binds cancer cells; imaging in surgical procedures; binding of histones for identification of various diseases; drug delivery, for example by replacing the M moiety in a disclosed compound with an active drug moiety; and/or contrast agents in dental work and other procedures, for example by preferential binding of the disclosed compound to various flora and/or organisms.

It is understood that any embodiment of the disclosed compounds, as set forth above, and any specific choice set forth herein for the variables in the compounds, as set forth above, may be independently combined with other embodiments and/or variables of the compounds to form embodiments of the invention not specifically set forth above. In addition, in the event that a list of choices is listed for any particular variable in a particular embodiment and/or claim, it is understood that each individual choice may be deleted from the particular embodiment and/or claim and that the remaining list of choices will be considered to be within the scope of the invention.

It is understood that in the present description, combinations of substituents and/or variables of the depicted formulae are permissible only if such contributions result in stable compounds.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include $-C(O)-R''$ (where R'' is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

Furthermore, embodiments of compounds of the invention which exist in free base or acid form can be converted to their salts by treatment with the appropriate inorganic or organic base or acid by methods known to one skilled in the art. Salts of the compounds of the invention can be converted to their free base or acid form by standard techniques.

The following Reaction Schemes illustrate exemplary methods of making compounds of this invention. It is understood that one skilled in the art may be able to make these compounds by similar methods or by combining other methods known to one skilled in the art. It is also understood that one skilled in the art would be able to make, in a similar manner as described below, other disclosed compounds not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

Reaction Scheme I

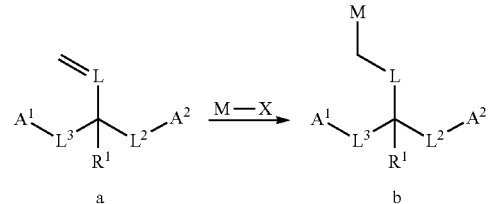

Reaction Scheme I illustrates an exemplary method for preparing an intermediate useful for preparation of compounds of structure (I), where $R^1$, $L^2$, $L^3$ and M are as defined above, $A^1$ and $A^2$ are as defined above or are protected variants thereof and L is an optional linker. Referring to Reaction Scheme 1, compounds of structure a can be purchased or prepared by methods well-known to those of ordinary skill in the art. Reaction of a with M-X, where x is a halogen such as bromo, under Suzuki coupling conditions known in the art results in compounds of structure b. Compounds of structure b can be used for preparation of further compounds as described below.

Reaction Scheme II

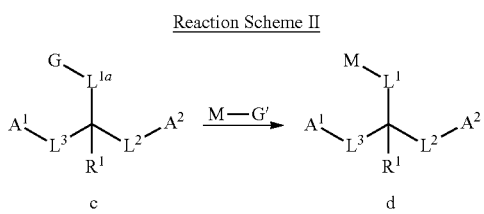

Reaction Scheme II illustrates an alternative method for preparation of intermediates useful for preparation of the disclosed compounds. Referring to reaction Scheme II, where $L^1$, $L^2$, $L^3$, and M are as defined above, and $A^1$ and $A^2$ are as defined above or are protected variants thereof, a compound of structure c, which can be purchased or prepared by well-known techniques, is reacted with M-G' to yield compounds of structure d. Here, G and G' represent functional groups having complementary reactivity (i.e., functional groups which react to form a covalent bond, such as alkyne and azide). G' may be pendant to M or a part of the structural backbone of M. G may be any number of functional groups described herein, such as alkyne.

The compounds may be prepared from one of structures b or d by reaction under well-known automated DNA synthesis conditions with a phosphoramidite compound having the following structure (e):

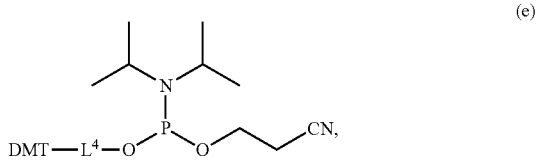

wherein A is as defined herein and each L is independently an optional linker.

DNA synthesis methods are well-known in the art. Briefly, two alcohol groups, for example $R^2$ and $R^3$ in intermediates b or d above, are functionalized with a dimethoxytrityl (DMT) group and a 2-cyanoethyl-N,N-diisopropylamino phosphoramidite group, respectively. The phosphoramidite group is coupled to an alcohol group, typically in the presence of an activator such as tetrazole, followed by oxidation of the phosphorous atom with iodine. The dimethoxytrityl group can be removed with acid (e.g., chloroacetic acid) to expose the free alcohol, which can be reacted with a phosphoramidite group. The 2-cyanoethyl group can be removed after oligomerization by treatment with aqueous ammonia.

Preparation of the phosphoramidites used in the oligomerization methods is also well-known in the art. For example, a primary alcohol (e.g., $A^2$) can be protected as a DMT group by reaction with DMT-Cl. A secondary alcohol (e.g., $A^1$) is then functionalized as a phosphoramidite by reaction with an appropriate reagent such as 2-cyanoethyl N,N-dissopropylchlorophosphoramidite. Methods for preparation of phosphoramidites and their oligomerization are well-known in the art and described in more detail in the examples.

The compounds are prepared by oligomerization of intermediates b or d and e according to the well-known phosphoramidite chemistry described above. The desired number of repeating units is incorporated into the molecule by repeating the phosphoramidite coupling the desired number of times.

The following examples are provided for purposes of illustration, not limitation.

EXAMPLES

General Methods

Mass spectral analysis was performed on a Waters/Micromass Quattro micro MS/MS system (in MS only mode) using MassLynx 4.1 acquisition software. Mobile phase used for LC/MS on dyes was 100 mM 1,1,1,3,3,3-hexafluoro-2-propanol (HFIP), 8.6 mM triethylamine (TEA), pH 8. Phosphoramidites and precursor molecules were also analyzed using a Waters Acquity UHPLC system with a 2.1 mm×50 mm Acquity BEH-C18 column held at 45° C., employing an acetonitrile/water mobile phase gradient. Molecular weights for monomer intermediates were obtained using tropylium cation infusion enhanced ionization on a Waters/Micromass Quattro micro MS/MS system (in MS only mode). Excitation and emission profiles experiments were recorded on a Cary Eclipse spectra photometer.

All reactions were carried out in oven dried glassware under a nitrogen atmosphere unless otherwise stated. Commercially available DNA synthesis reagents were purchased from Glen Research (Sterling, VA). Anhydrous pyridine, toluene, dichloromethane, diisopropylethyl amine, triethylamine, acetic acid, pyridine, and THF were purchased from Aldrich. All other chemicals were purchase from Aldrich or TCI and were used as is with no additional purification.

Example 1

Synthesis of Phosphoramidite Dye Monomers

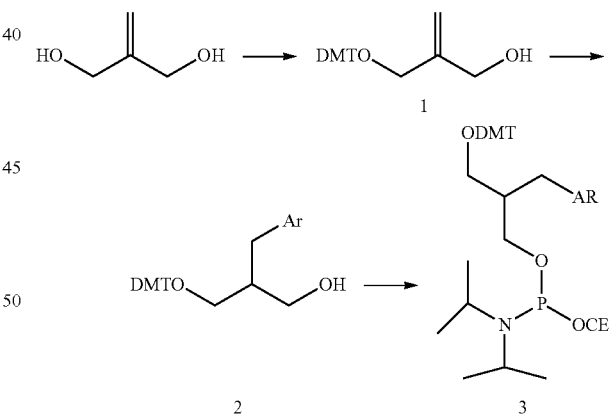

Ar = pyrene
DMT = 4,4'-dimethoxytrityl
CE = 2-cyanoethyl

1-O-(4,4'-dimethoxytrityl-2-methylene-1,3-propanediol (1)

Into a dry 500 mL round bottom flask was put a stir bar. After flushing with nitrogen, dry pyridine (240 mL) was added, and the flask was cooled in an ice bath for 15 minutes. Upon cooling DMTrCl (7.65 g, 22.5 mmol) was added after which the flask was stirred overnight in a refrigerator at 4°

C. under a nitrogen atmosphere. Several drops of methanol were then added and the reaction was concentrated in vacuo to a viscous gum. The resulting gum was dissolved in EtOAc (200 mL) and washed with NaHCO$_3$ (250 mL) and sat. NaCl (250 mL). The organic layer was dried over Na$_2$SO$_4$ and concentrated in vacuo to a viscous gum. The isolated crude product wash then purified by silica gel column chromatography eluting with a gradient of EtOAc:hexanes (25:75 v/v)-(1:1 v/v) to give 1 as a clear gum (5.21 g, 60%). $^1$H NMR was recorded and found to be consistent with the structure of compound 1.

1-O-(4,4'-dimethoxytrityl)-2-hydroxymethyl-3-pyrenylpropanol (2)

Into a dry 250 mL round bottom flask fitted with a condenser was put a stir bar. The flask was purged with nitrogen, and dry THF (40 mL) and compound 1 (5.0 g, 12.8 mmol) were added. 0.5 M 9-BBN in THF (65 mL, 32 mmol) was added via syringe and the reaction was heated to reflux for 12 hrs. After allowing the reaction to cool to room temperature, 3M K$_2$CO$_3$ (11 ml) and dry DMF (100 mL) were added. 1-Bromopyrene (2.0 g, 6.5 mmol) and PdCl$_2$(dppf) (0.65 g, 0.8 mmol) were added, and the solution was allowed to stir for 15 hrs at room temperature. The reaction mixture was poured into CH$_2$Cl$_2$ (300 mL) and washed with H$_2$O (500 mL). The aqueous layer was then back extracted with additional CH$_2$Cl$_2$ (200 mL). The combined organic layers were washed with sat. NaCl (300 mL), dried over Na$_2$SO$_4$, and concentrated in vacuo to a viscous gum. The isolated crude product wash then purified by silica gel column chromatography eluting with a gradient of EtOAc:hexanes (25:75 v/v)-(1:1 v/v) to give 2 as a clear gum (3.0 g, 79%). The $^1$H NMR spectrum was recorded and found to be consistent with the structure of compound 2.

1-O-(4,4'-dimethoxytrityl)-2-methylpyrene-3-O-(2-cyanoethyl-N,N-diisopropyl) propane phosphoramidite (3)

Into a dry 100 mL round bottom flask was put a stir bar. After purging the flask with nitrogen, CH$_2$Cl$_2$ (20 mL) and compound 2 (0.30 g, 0.50 mmol) were added. N,N-Diisopropylethylamine (0.88 mL, 5.0 mmol) and 2-cyanoethyl diisopropylchlorophosphoramidite (0.45 mL, 2.0 mmol) were added via syringe. After 1 hour of stirring at room temperature, the reaction was determined to be complete by TLC analysis. The crude reaction mixture was then purified directly by silica gel column chromatography eluting with a gradient of EtOAc:hexanes:TEA (22.5:72.5:5 v/v/v) to give 3 as a white foam (0.28 g, 70%). The $^{31}$P NMR spectrum was recorded and found to be consisted with the structure of compound 3: Purity was determined by HPLC analysis with detection at 254 and 340 nm.

Other compounds with different Ar groups (e.g., any of the "M" groups described herein) were prepared in an analogous manner.

Example 2

Synthesis of Perylene Carbodiimide Dye Monomer

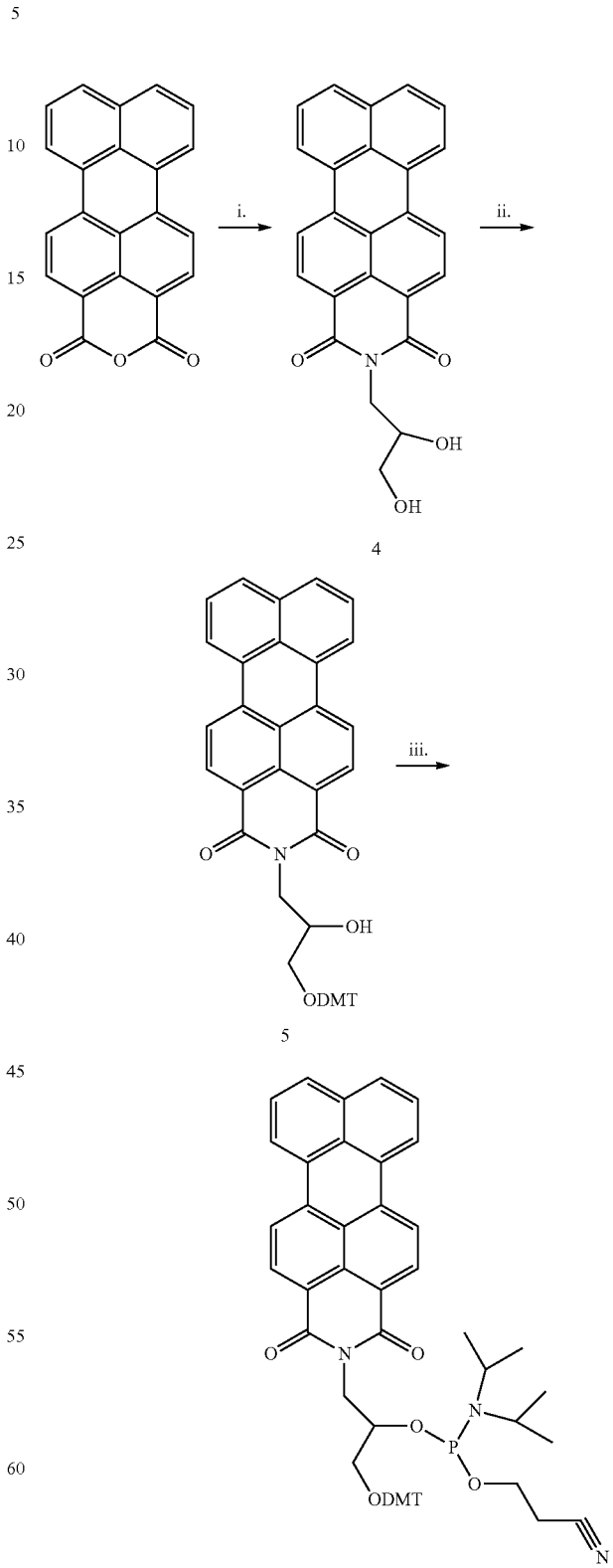

N-(2,3-propanediol) perylenemonoimide (4)

Into a dry 200 mL round bottom flask fitted with a condenser was put a stir bar and perylene monoanhydride[1] (1.83 g, 5.67 mmol). After adding 3-amino-1,2-propanediol (1.1 g, 2.1 mmol) and imidazole (14.3 g, 0.21 mol), the vessel was heated to 140° C. in an oil bath for 15 hours. The reaction was allowed to cool to room temperature and then 10% HCl was added (500 mL). The resulting deep red precipitate was collected by filtration, washed well with water and dried at 180° C. for several hours to yield 4 as a deep red solid (1.95 g, 86%).

N-(3-O-(4,4'-dimethoxytrityl-2-hydroxypropane) perylenemonoimide (5)

Into a dry 200 mL round bottom flask was put a stir bar. After purging the flask with nitrogen, dry pyridine (120 mL), compound 4 (0.44 g, 1.1 mmol), and dimethoxytritylchloride (0.45 g, 1.3 mmol) were all added, and the reaction was allowed to stir at room temperature for 48 hours. Several drops of methanol were then added, and the reaction was concentrated in vacuo to a viscous gum. The resulting gum was dissolved in $CH_2Cl_2$ (200 mL) and washed with sat. NaCl (200 mL). The aqueous layer was washed with in $CH_2Cl_2$ (3×100 mL). The combined organic layers were dried over $Na_2SO_4$ and concentrated in vacuo to a viscous gum. The isolated crude product wash then purified by silica gel column chromatography eluting with a gradient of EtOAc: $CH_2Cl_2$ (0:100 v/v)-(2:3 v/v) to give 5 as a red foam (0.25 g, 50%).

N-(3-O-(4,4'-dimethoxytrityl-2-O-(2-cyanoethyl-N, N-diisopropylamino phosphoramidite) perylenemonoimide (6)

Into a dry 50 mL round bottom flask was put a stir bar. After purging the flask with nitrogen, $CH_2Cl_2$ (5 mL) and compound 5 (0.25 g, 0.36 mmol) were added. N,N-diisopropylethylamine (0.24 mL, 1.79 mmol) and 2-cyanoethyl N,N-diisopropychlorophosphoramidite (0.16 mL, 0.72 mmol) were added via syringe. After 1 hour of stirring at room temperature, the reaction was determined to be complete by TLC analysis. The crude reaction mixture was then purified directly by silica gel column chromatography eluting with $CH_2Cl_2$:TEA (95:5 v/v) to give 6 as a dark red foam (0.26 g, 80%). The purified compound was analyzed by RP-HPLC with observation at 254 and 500 nm. Two diastereomers were found to be present.

Other dye monomers with different M groups were prepared in an analogous manner.

Example 3

Synthesis of Oligomer Dyes

Oligomer dyes were synthesized on an Applied Biosystems 394 DNA/RNA synthesizer or on GE AKTÄ 10 OligoPilot on either 1 µmol or 10 µmol scales and possessed a 3'-phosphate group. Dyes were synthesized directly on CPG beads or on polystyrene solid support. The dyes were synthesized in the 3' to 5' direction by standard solid phase DNA methods. Coupling methods employed standard β-cyanoethyl phosphoramidite chemistry conditions. Different number of "m" repeating units were incorporated by repeating the synthesis cycle the desired number of times with an appropriate phosphoramidite. All phosphoramidite monomers were dissolved in acetonitrile/dichloromethane (0.1 M solutions), and were added in successive order using the following synthesis cycles: 1) removal of the 5'-dimethoxytrityl protecting group with dichloroacetic acid in toluene, 2) coupling of the next phosphoramidite with activator reagent in acetonitrile, 3) oxidation with iodine/pyridine/water, and 4) capping with acetic anhydride/1-methylimidizole/acetonitrile. The synthesis cycle was repeated until the 5' Oligofluoroside was assembled. At the end of the chain assembly, the monomethoxytrityl (MMT) group or dimthoxytrityl (DMT) group was removed with dichloroacetic acid in dichloromethane or dichloroacetic acid in toluene.

The dyes were cleaved from the solid support and deprotected as follows:

A 1 mL micropipettor was used to add 450 µL of concentrated $NH_4OH$ to ~25 mg of reacted CPG solid support in a 1.5 mL Eppendorf tube. The slurry was mixed briefly using a Vortex mixer and allowed to settle before placing (open) on a 55° C. heating block until gas formation (and bubbling) started to diminish, at which point the tube was tightly closed. Heat treatment was for 2 hours (+/−15 minutes) and tubes were then removed to cool to room temperature. The tube and its contents were spun in a centrifuge at its maximum speed (13400 rpm) for 1 minute, and then the supernatant was removed with a glass pipette and placed into a second, labeled, 1.5 mL Eppendorf tube, taking care not to include the support. The support was washed and spun-down 2× with ~150 µL of acetonitrile to help maximize dye removal, and the washings were carefully removed from support and added to the labeled secondary tubes. Clarified supernatant was dried completely in a CentriVap concentrator at 40° C. to remove $NH_4OH$.

Example 4

Synthesis of Oligomer Dyes

The compounds in Table 2 were prepared according to the above general procedures and used for preparation of higher polymeric dyes according to the procedures which follow. For ease of illustration, the compounds are often depicted schematically in the following examples; however, it is understood that the schematics represent the specific compounds depicted in Table 2.

TABLE 2
Exemplary Compounds
| No. | Structure |
|---|---|
| 1 | 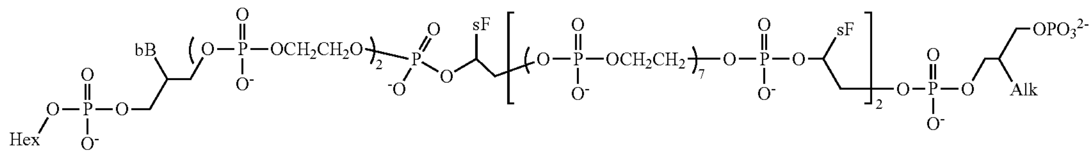 |
| 2 | 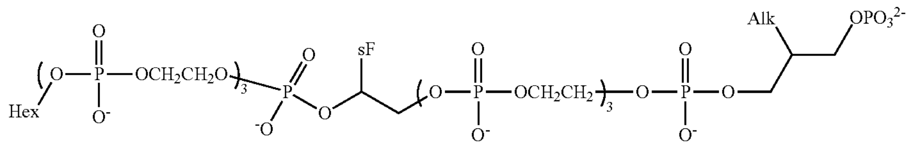 |
| 3 | 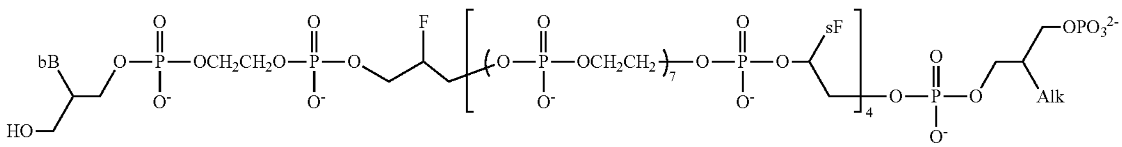 |
| 4 | 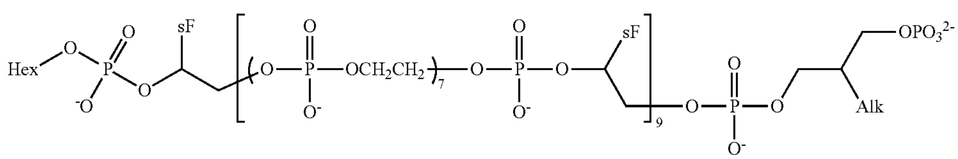 |
| 5 | 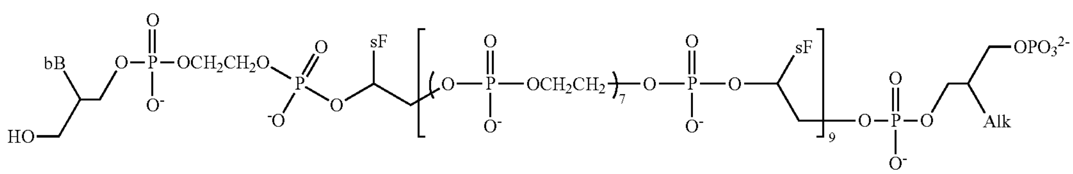 |
The abbreviations in Table 2 and throughout the application represent the following structures:
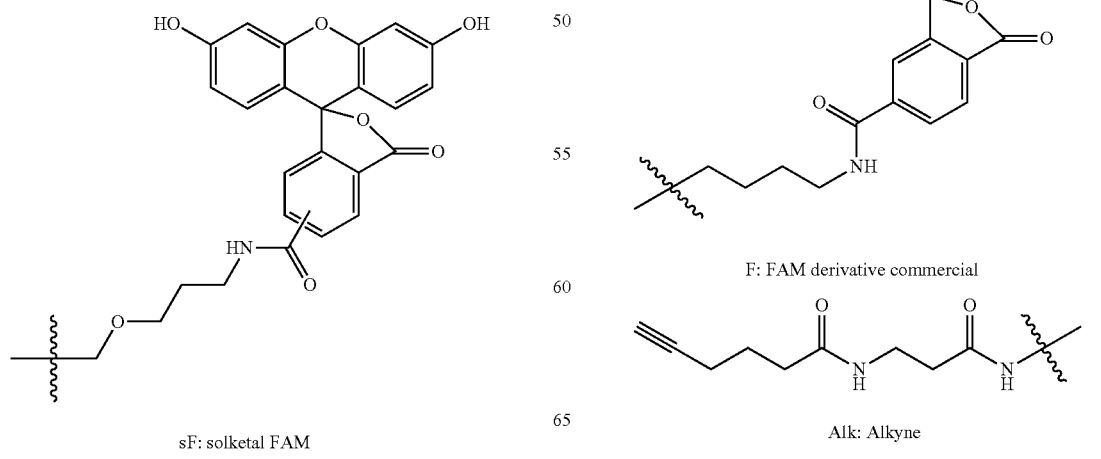
sF: solketal FAM
F: FAM derivative commercial
Alk: Alkyne

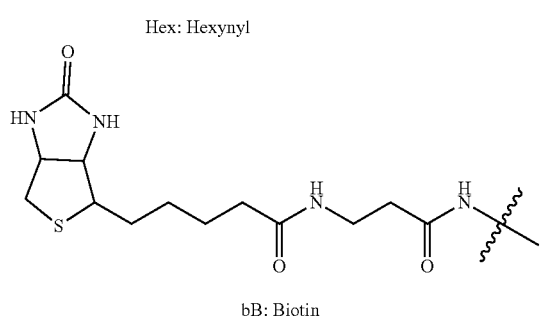

Hex: Hexynyl

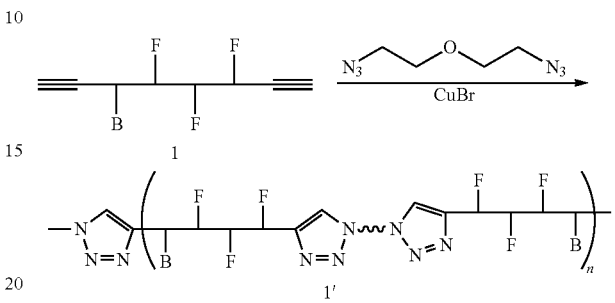

bB: Biotin

Example 5

Polymerization of Compound 4

Compound 4 was polymerized using triazole chemistry according to the following scheme, wherein 4 represents compound 4 above, 4' represents a dimer or polymer of 4 linked by triazole groups and n is an integer of 1 or more:

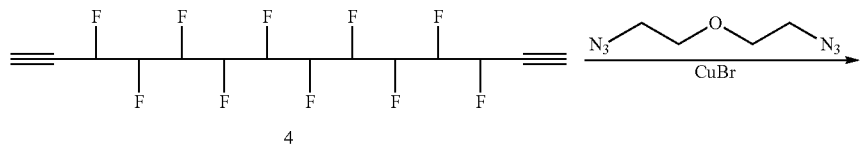

4

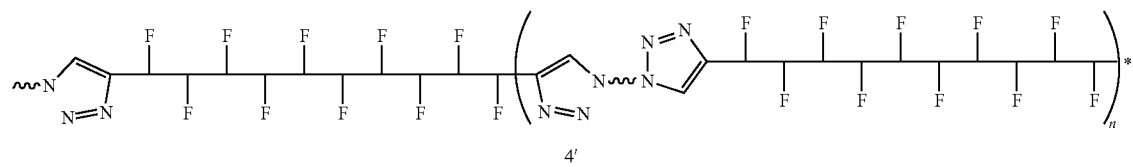

4'

In a 200 μL polypropylene tube was placed sodium phosphate buffer (8.8 μL, 150 mM, pH=7.2) and a solution of compound 4 (2.25 μL, 5 mM in water). To this was added a solution of 1,5-diazido-3-oxapentane (1.0 μL, 7.5 mM in water) and copper bromide (3.0 μL, 100 mM in DMSO). The tube was capped, vortexed and then heated to 85° C. for 36 h. The reaction mixture was examined by analytical SEC (column:Superdex 200 Increase 5/150GL (28-9409-45), Isocratic elution with 100% PBS buffer, flow rate: 0.25 mL/min, UV monitoring at 280 and 494 nm, run time: 17 min). The HPLC chromatogram showed an earlier eluting peak (relative to starting material), indicating formation of compound 4'.

Example 6

Polymerization of Compound 1

Compound 1 was polymerized using triazole chemistry according to the following scheme, wherein 1 represents compound 1 above, 1' represents a dimer or polymer of 1 linked by triazole groups and n is an integer of 1 or more:

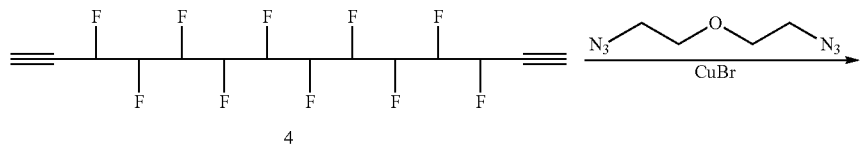

In a 200 μL polypropylene tube was placed 50/50 DMSO/water (3.0 μL) and a solution of 1 (4.0 μL, 12.5 mM). To this was added a solution of 1,5-diazido-3-oxapentane (2.0 μL, 25 mM in water) and copper bromide (1.0 μL, 50 mM in DMSO). The tube was capped and vortexed. The tube was placed in a commercial microwave and irradiated for 4 min at 450 watts (½ power) and then allowed to stand for 1 min. This cycle was repeated seven times. The mixture was analyzed by LC/MS and analytical SEC. The data was consistent with formation of a higher molecular weight species (i.e., 1').

Example 7

Dimerization of Compound 5

Compound 5 was dimerized using triazole chemistry according to the following scheme, wherein 5 represents compound 5 above and 5' represents a dimer of 5 linked by a triazole group:

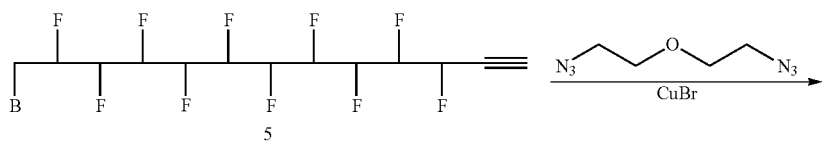

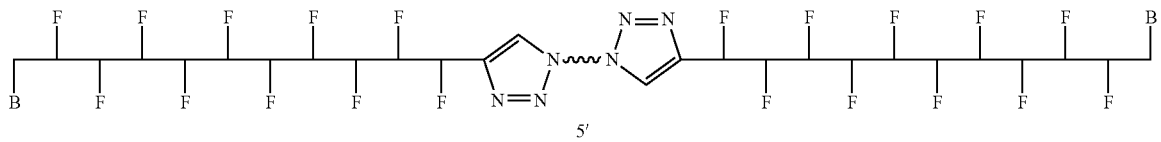

Compound 5 was purified by a semiprep SEC column (Column:Superdex 200, isocratic elution with PBS, flow rate 10 mL/min, monitor at 494 nm). Fractions were examined by SDS-PAGE gel (4-20% Tris-Gly, Invitrogen) and pooled according to purity. In a 200 μL polypropylene tube was placed sodium phosphate buffer (1.4 μL, 600 mM, pH=7.2) and a solution of purified compound 5 (5.56 μL, 1.8 mM). To this was added a solution of 1,5-diazido-3-oxapentane (1.0 μL, 5 mM in water) and copper bromide (2.0 μL, 100 mM in DMSO). The tube was capped, vortexed and allowed to incubate at room temperature overnight. The reaction mixture was examined by analytical SEC (column: Superdex 200 Increase 5/150GL (28-9409-45), Isocratic elution with 100% PBS buffer, flow rate: 0.25 mL/min, UV monitoring at 280 and 494 nm, run time: 17 min).

Analysis by SDS-PAGE and SEC confirmed formation of the dimer 5'.

Example 8

Dimerization of Compound 3

Compound 3 was dimerized using triazole chemistry according to the following scheme, wherein 3 represents compound 3 above and 3' represents a dimer of 3 linked by a triazole group:

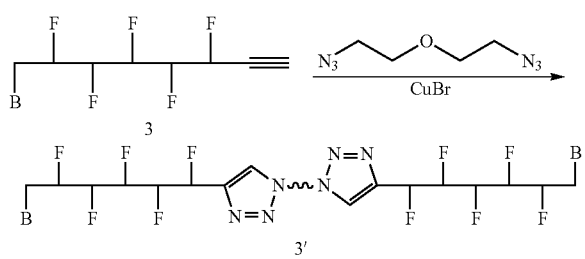

In a 200 μL polypropylene tube was placed sodium phosphate buffer (9.5 μL, 150 mM, pH=7.2) and a solution of 3 (3.0 μL, 5 mM in water). To this was added a solution of 1,5-diazido-3-oxapentane (1.0 μL, 7.5 mM in water) and copper bromide (1.5 μL, 100 mM in DMSO). The tube was capped, vortexed and incubated for 72 h. The reaction mixture was examined by analytical SEC (column: Superdex 200 Increase 5/150GL (28-9409-45), Isocratic elution with 100% PBS buffer, flow rate: 0.25 mL/min, UV monitoring at 280 and 494 nm, run time: 17 min). The SEC trace showed formation of a new, earlier eluting peak, consistent with formation of dimer 3'.

Example 9

Preparation of Azido-Modified Compound 1 and Polymerization Thereof

Compound 1 was modified to include azide groups at both termini according to the following scheme, wherein 1 represents compound 1 above and 1" represents the azido modified compound 1:

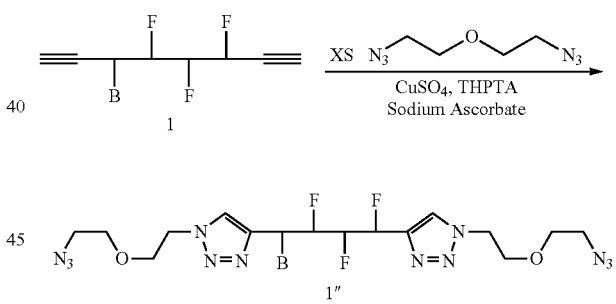

In a 200 μL polypropylene tube was placed sodium phosphate buffer (14.4 μL, 200 mM, pH=7.2), a solution of 1 (1.2 μL, 12.5 mM in water) and a solution of 1,5-diazido-3-oxapentane (6.0 μL, 50 mM in water). In a separate tube, aqueous solutions of copper sulfate (3.0 μL, 20 mM), tris(3-hydroxypropyltriazolylmethyl)amine, (THPTA, 2.4 μL, 50 mM in water) and sodium ascorbate (3.0 μL, 100 mM) were combined and mixed. The entire contents of the copper solution were added the azide-alkyne solution, the tube capped, mixed and allowed to incubate overnight at room temperature. The reaction was diluted to 75 μL with water and desalted (Pierce Zeba mini desalting column 7K MWCO (cat #89882)). Concentration determination was made on a nanodrop (e=22500 1/M cm).

Azido-modified compound 1 was polymerized using triazole chemistry as follows, wherein 1' represents a polymer of 1 and "alkyne" represents any one of compounds 1-5.

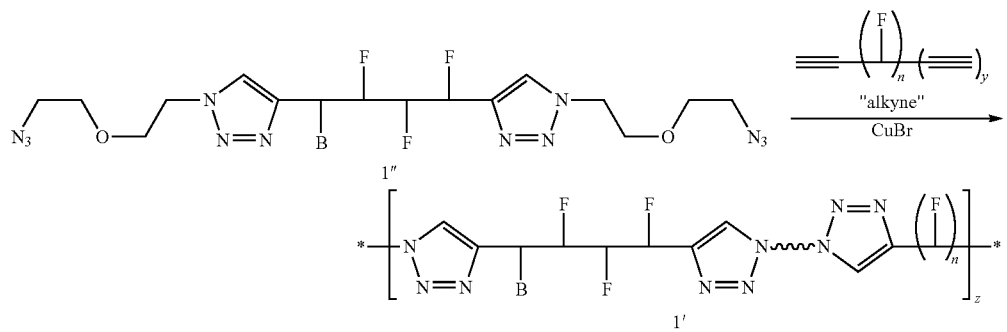

A series of FAM-phosphate alkynes (e.g., compounds 1-5) were reacted with the azide modified compound 1 as follows:

In a 200 μL polypropylene tube was placed sodium phosphate buffer (8.3 μL, 300 mM, pH=7.2) and a solution of 1″ (2.5 μL, 30 μM). To this was added a solution of 1 (1.2 μL, 63 μM) and copper bromide (3.0 μL, 100 mM in DMSO). The tube was capped, vortexed and incubated overnight. The reaction mixture was examined by analytical SEC (column: Superdex 200 Increase 5/150GL (28-9409-45), Isocratic elution with 100% PBS buffer, flow rate: 0.25 mL/min, UV monitoring at 280 and 494 nm, run time: 17 min). Compounds 2-5 were reacted with 1″ in an analogous manner. In each instance, analytical SEC indicated formation of compound 1′

Example 10

Nucleophilic Polymerizations

Analogues of compounds 1-5 including nucleophilic groups at both termini (represented by A below) are prepared and reacted with a bis electrophile (represented by B below) to form a dimer or higher polymer (represented by C below) according to the following scheme:

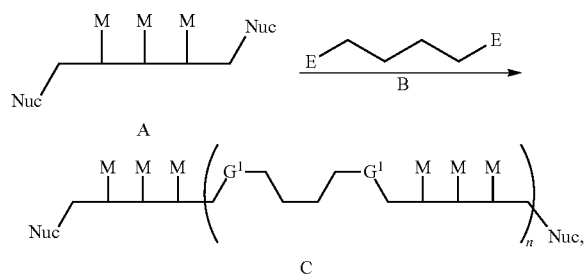

where nuc is a nucleophile, E is an electrophile and n is an integer of one or more. Exemplary nucleophiles, complementary electrophiles and the resulting product "$G^1$" are provided in Table 3.

TABLE 3

Nucleophiles, Electrophiles and Products

| Nucleophile (Nuc) | Electrophile (E) | Product ($G^1$) |
|---|---|---|
| $NH_2$ | Acid Chloride, NHS ester | Amide |

TABLE 3-continued

Nucleophiles, Electrophiles and Products

| Nucleophile (Nuc) | Electrophile (E) | Product ($G^1$) |
|---|---|---|
| $NH_2$, NHR, SH, OH; R = alkyl | NCO, NCS | Urea, Carbamate, Urethane, Thio-Carbamate |
| $NH_2$, NHR, SH, OH; R = alkyl | Epoxide | Amino-alcohol, Thio-ether-alcohol, ether-alcohol |
| $NH_2$, NHR, SH, R = alkyl | Alkyl Halide, Alkyl tosylate, Mesylate, Triflate | Amine, Thio-ether |
| SH | Maleimide | Alkyl sulfide |
| SH | Alkene | |

Example 11

Electrophilic Polymerizations

In a manner analogous to Example 10, analogues of compounds 1-5 including electrophilic groups at both termini (represented by D below) are prepared and reacted with a bis nucleophile (represented by E below) to form a dimer or higher polymer (represented by F below) according to the following scheme:

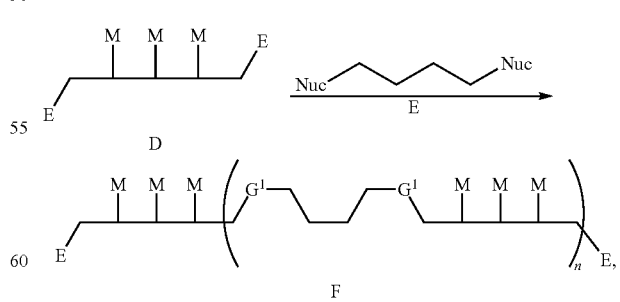

where nuc is a nucleophile, E is an electrophile and n is an integer of one or more. Exemplary nucleophiles, complementary electrophiles and the resulting product "G¹" are provided in Table 4.

TABLE 4

Electrophiles, Nucleophiles and Products

| Electrophile (E) | Nucleophile (Nuc) | Product (G¹) |
|---|---|---|
| NHS Ester, Phenolate Ester | NH$_2$, NHR, SH, R = alkyl | Amide, Thioester |
| Alkyl Halide, Alkyl Tosylate, Mesylate, Triflate | NHR, SH, R = alkyl | Amine, Thioether |

Example 12

Polyphosphate Condensation

Analogues of compounds 1-5 including a phosphate group at least one terminus (represented by F below) are prepared and polymerized under heat and/or acid conditions according to the following scheme:

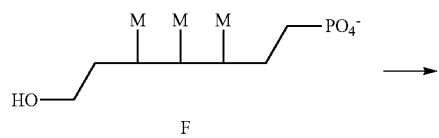

F

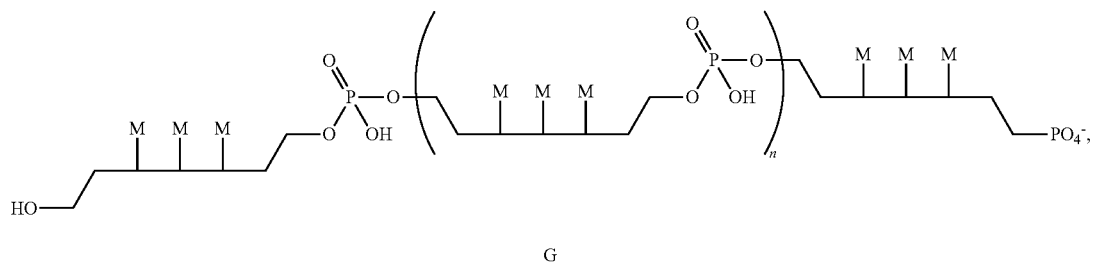

G where n is an integer of one or more.

Example 13

Ring Opening Metathesis Polymerizations (ROMP)

Analogues of compounds 1-5 including a cyclic olefin group at one terminus (represented by H below) are prepared and treated under ring opening metathesis conditions to form a dimer or higher polymer (represented by I and I' below) according to one of the following schemes:

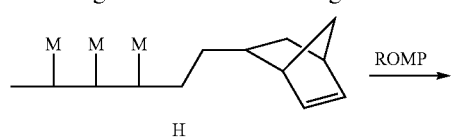

H

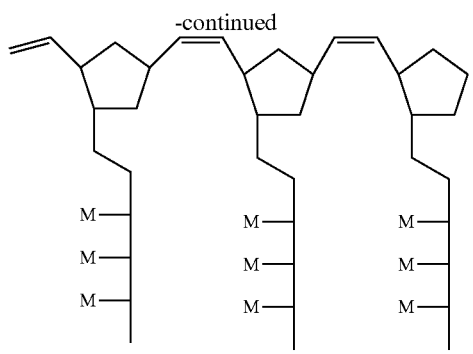

I or

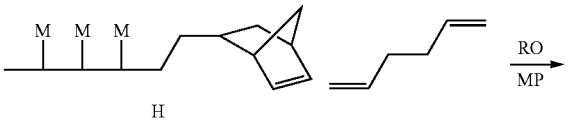

H

I'

Example 14

Olefin Cross Metathesis Polymerizations (ROMP)

Analogues of compounds 1-5 including an alkene group at each terminus (represented by J below) are prepared and treated under ring opening metathesis conditions to form a dimer or higher polymer (represented by K and K' below) according to one of the following schemes:

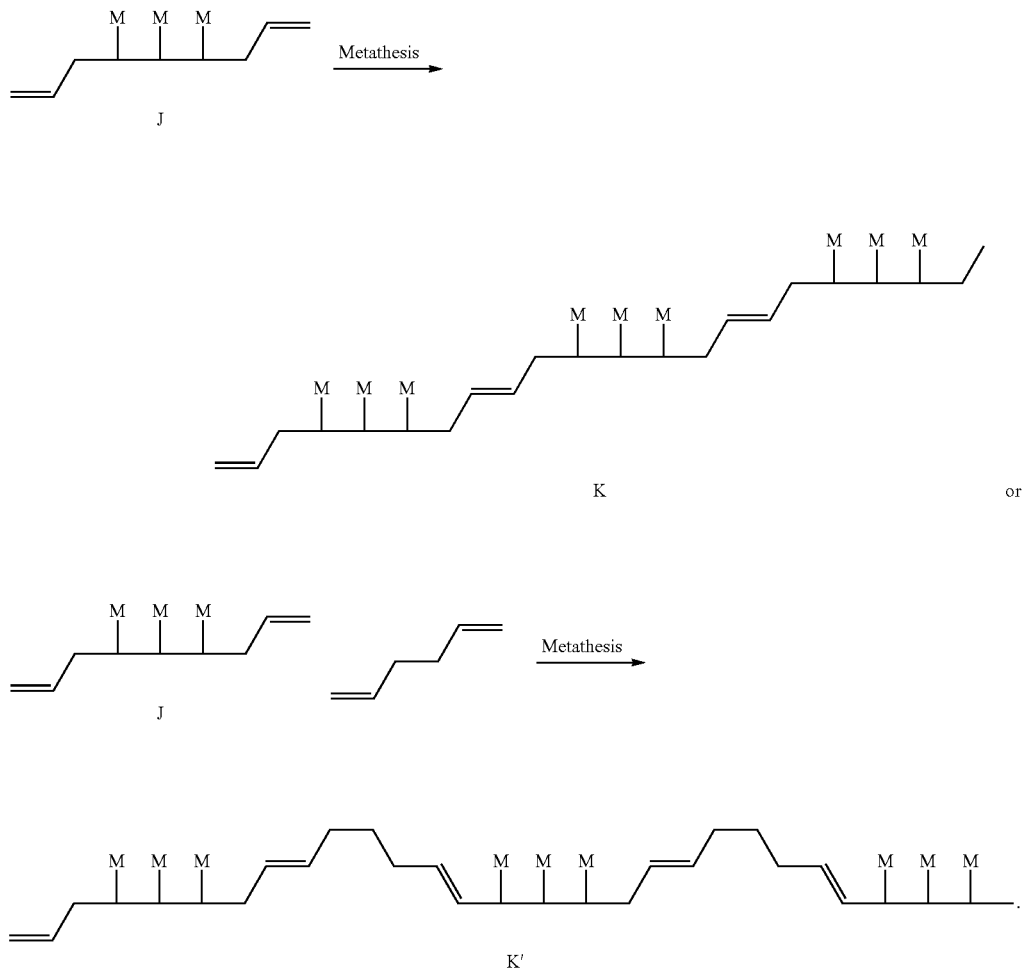

Example 15

Atom Transfer Radical Polymerizations (ATRP)

Analogues of compounds 1-5 including an acrylate group at one terminus (represented by L below, R=alkyl) are prepared and treated under ATRP conditions to form a dimer or higher polymer (represented by N below) according to one of the following schemes:

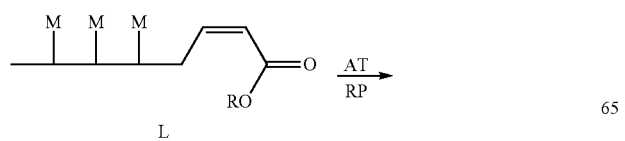

-continued

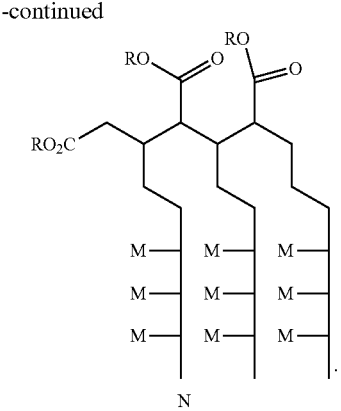

Example 16

DNA Base Pairing

Analogues of compounds 1-5 including a DNA base sequence at both termini (represented by O) are prepared and annealed to form a dimer or higher polymer (represented by P below) according to the following scheme, wherein n is an integer of 0 or greater:

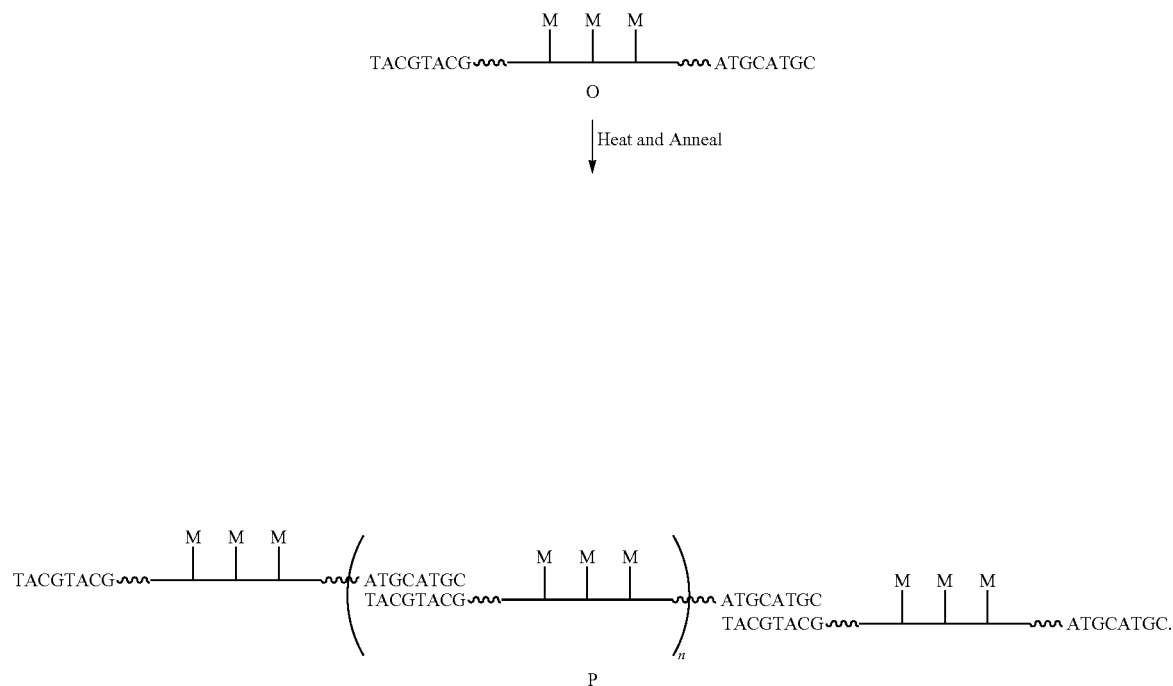

In a related embodiment, a polyalkyne is prepared and conjugated to a DNA sequence comprising a terminal azide to form a triazole/DNA-containing polymer as shown below. Separately, analogues of compounds 1-5 having a terminal DNA base sequence (O') are prepared and annealed to form P'.

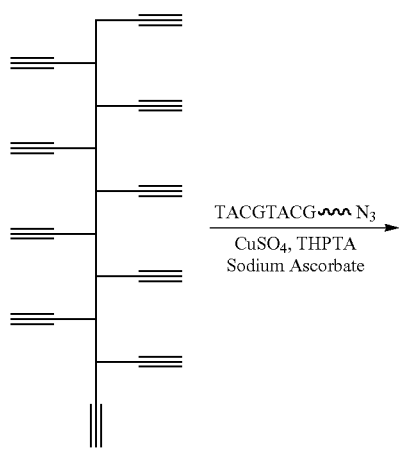

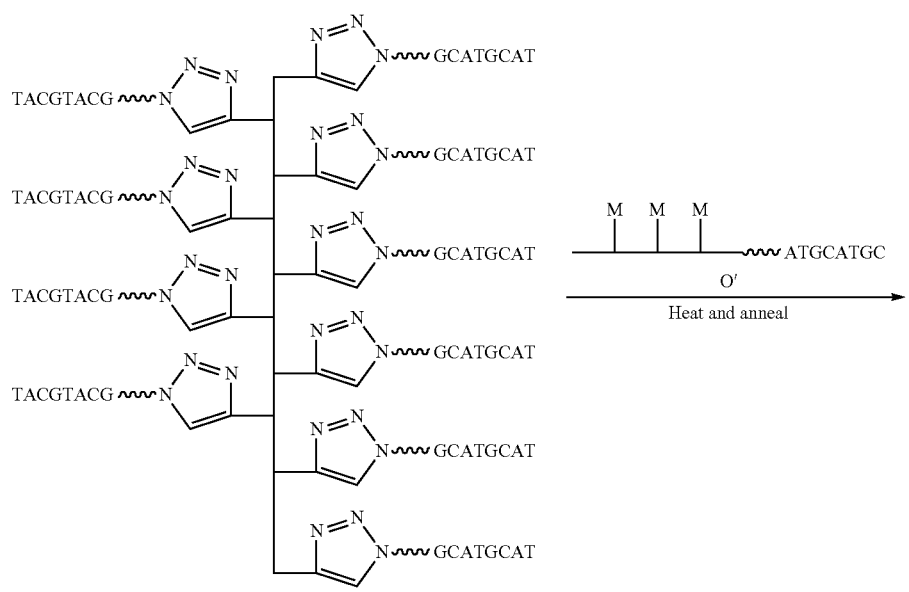

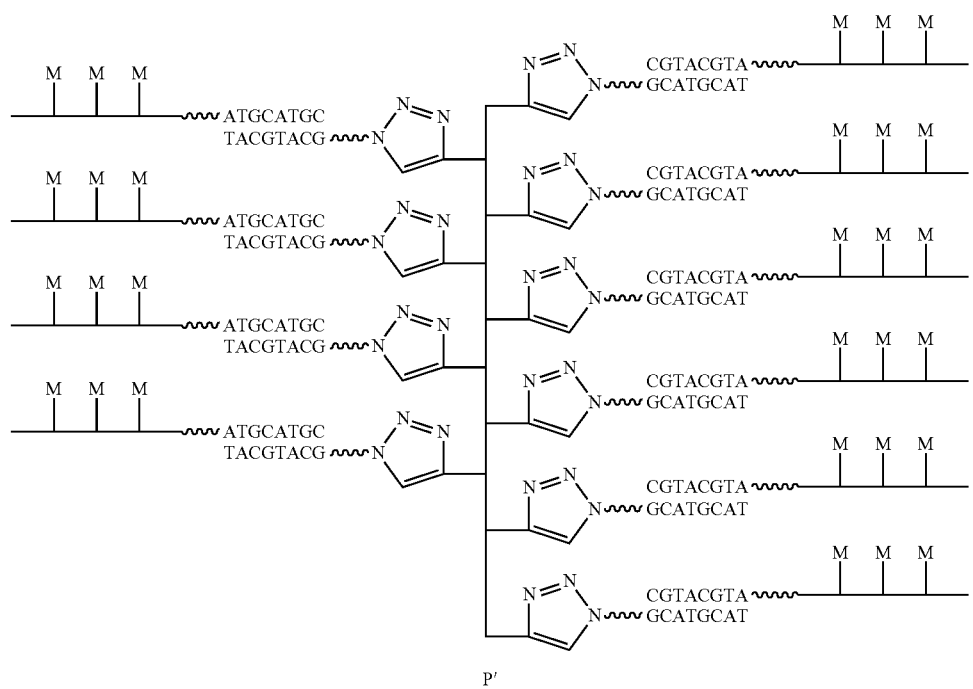

Example 17

Palladium Coupling Reactions

Analogues of compounds 1-5 including an appropriate group for palladium coupling reactions at one or both termini (represented by Q, Q' and Q", X=halogen) are prepared and reacted under appropriate conditions to form a dimer or higher polymer (represented by R, R', R" and R''' below) according to one of the following schemes, wherein n is an integer of 1 or greater:

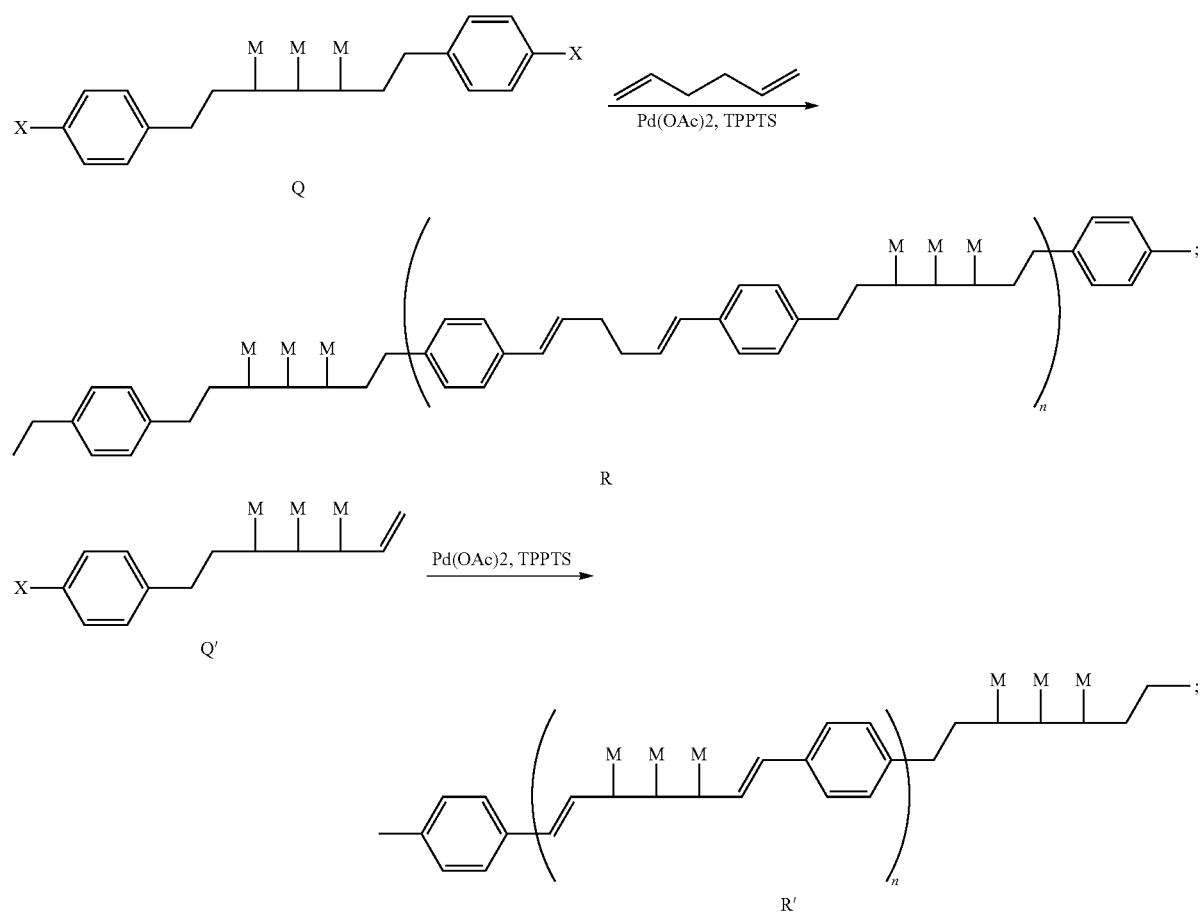
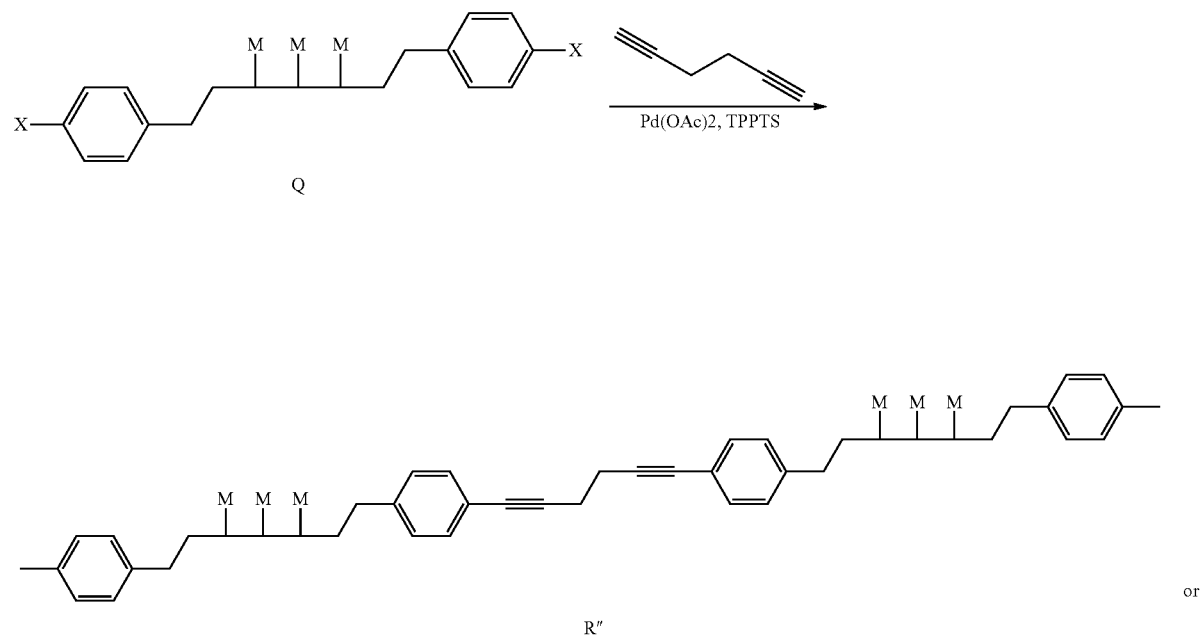

-continued

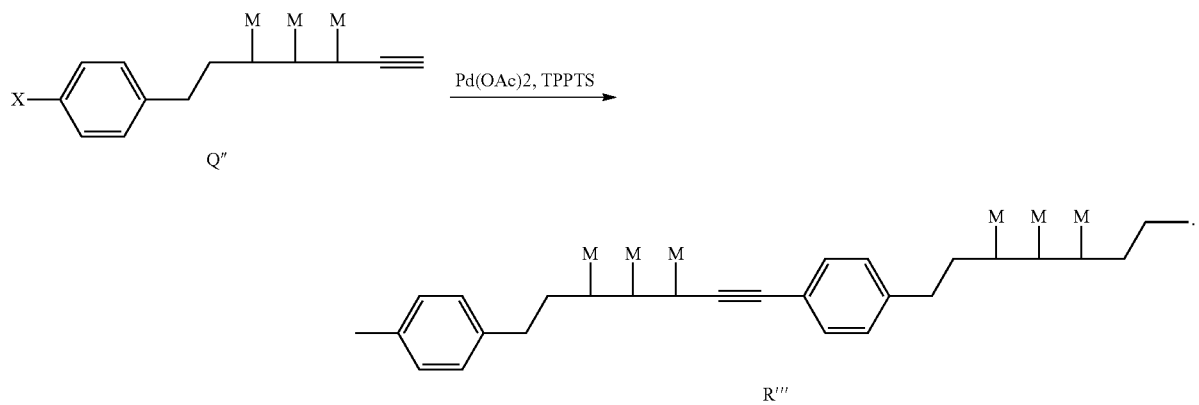

In related examples, analogues of compounds 1-5 including an appropriate group Suzuki (boronic acid/ester+aryl halide or alkyl halide), Stille (alkyl or aryl stannane+aryl or alkyl halide) or Buchwald (amine+aryl or alkyl halide) coupling are prepared and coupled with a complementary functional group, which may be present in the same compound or in a separate compound, to form dimer and higher polymers.

Example 18

Grafting to Existing Polymers

Analogues of compounds 1-5 including a reactive group (e.g., nucleophile, such as amino) for reaction with a complementary reactive group on a polymer (represented by S below) are prepared and reacted under appropriate conditions to form a grafted polymer according to one of the following schemes, wherein T is an NHS-activated polyethylene glycol and U is a polyglutamic acid or polyacrylic acid:

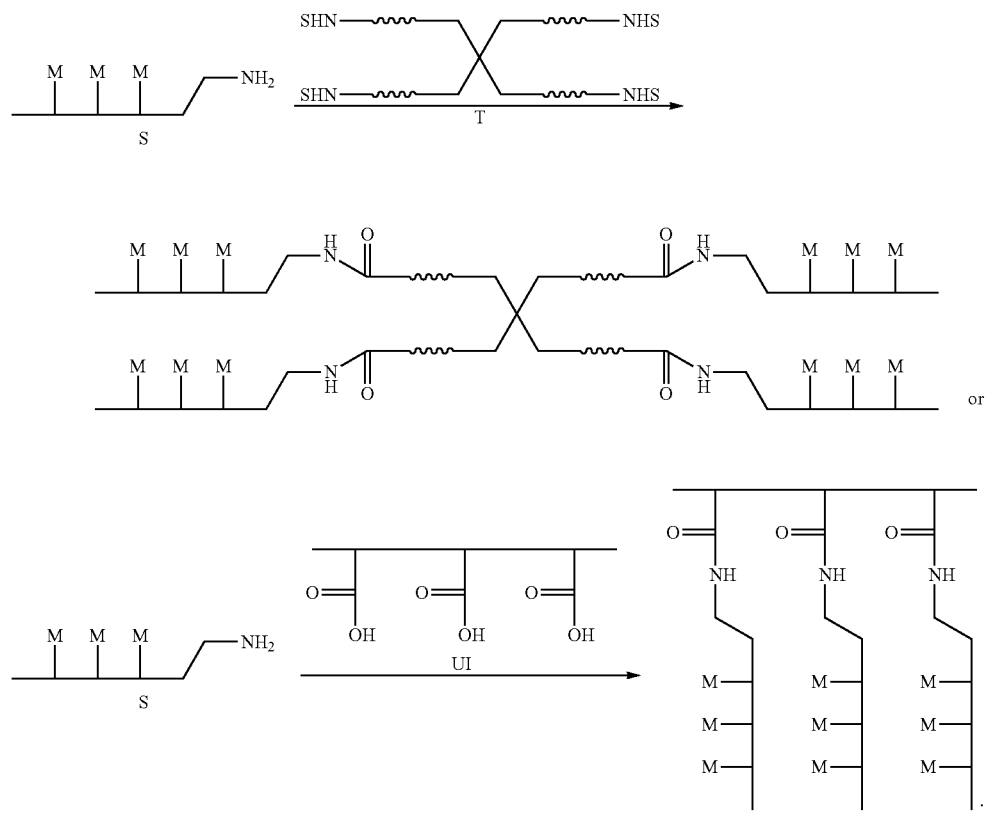

All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound having one of the following structures (III) or (IV):

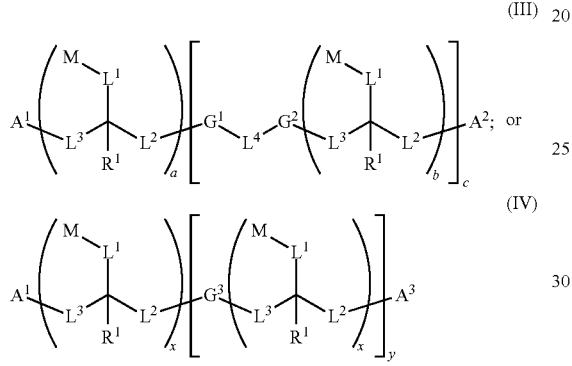

wherein:
- $A^1$, $A^2$ and $A^3$ are each independently alkyne, OH, —OP(=$R_a$)($R_b$)$R_c$ or Q, wherein: $R_a$ is O; $R_b$ is O⁻ or O$R_d$; $R_c$ is O⁻, O$R_d$ or OL'; and $R_d$ is a counter ion;
- $G^1$, $G^2$, and $G^3$ are each independently moieties selected from the group consisting of a urea, carbamate, urethane, thiocarbamate, amino-alcohol, thioether-alcohol, ether-alcohol, amine, thioether, thioester, double-stranded nucleic acid, and triazole functional group;
- M is, at each occurrence, independently a fluorescent or colored dye moiety or Q, wherein at least one occurrence of M is a fluorescent or colored dye moiety for at least one integral value of a and b;
- $R^1$ is, at each occurrence, independently H, alkyl or alkoxy;
- Q is, at each occurrence, independently a moiety having one of the following structures:

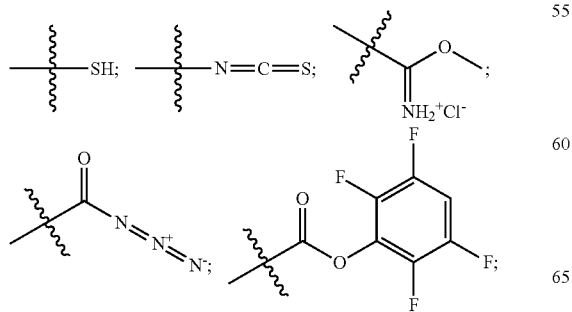

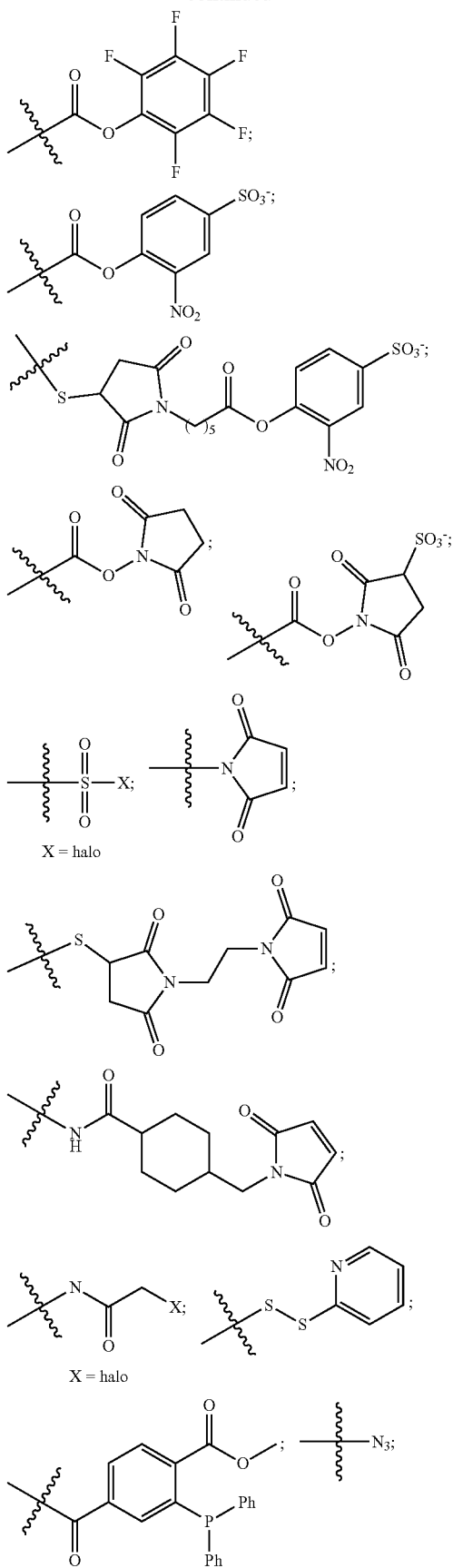

-continued

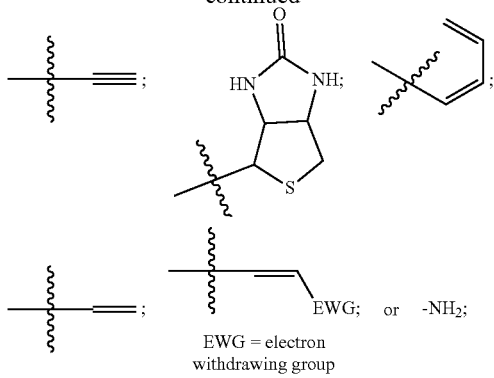

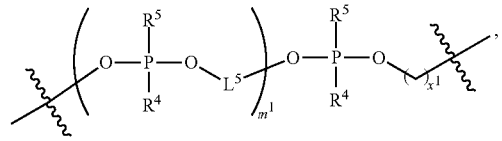

EWG = electron withdrawing group

L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (III) or (IV);

$L^1$ and $L^2$ are, at each occurrence, independently optional bivalent linker moieties;

$L^3$, at each occurrence, independently has the following structure:

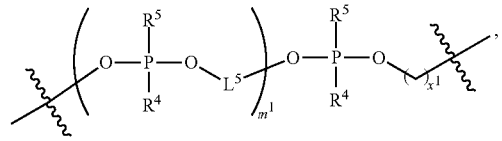

wherein:
$R^4$ is, at each occurrence, independently OH, SH, O$^-$, S$^-$, OR$_d$ or SR$_d$;
$R^5$ is, at each occurrence, independently oxo, thioxo or absent; and
$m^1$ and $x^1$ are, at each occurrence, independently an integer from 0 to 10;
$L^5$ is an alkylene, alkenylene, alkynylene, heteroalkylene, heteroalkenylene, heteroalkynylene, carbocyclic or heterocyclic linker;
$L^4$ is an optional multivalent linker moiety;
a, b and c are independently an integer of 1 or greater;
each x is independently an integer of 1 or greater; and
y is an integer of 1 or greater.

2. A compound having one of the following structures:

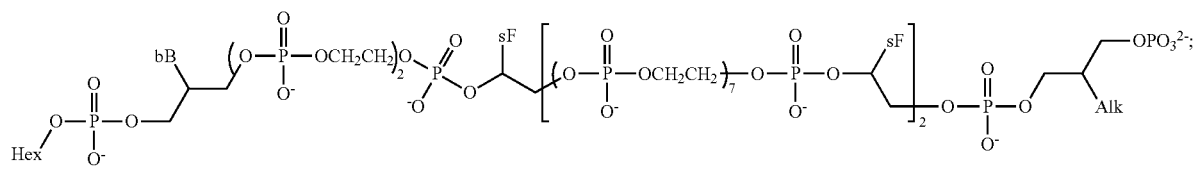

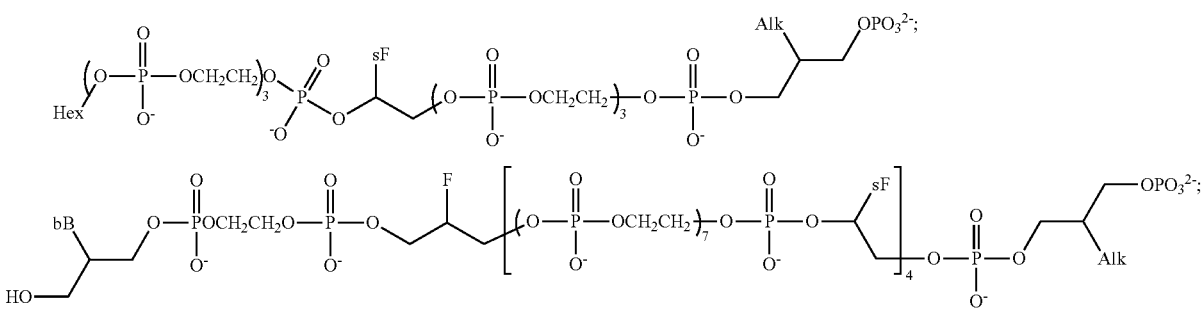

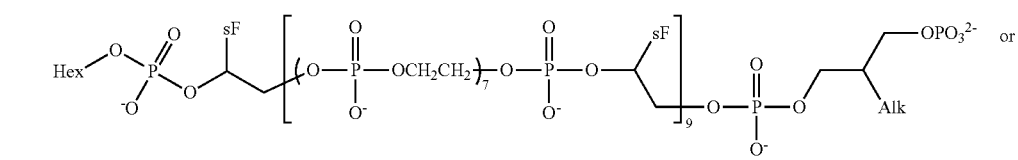

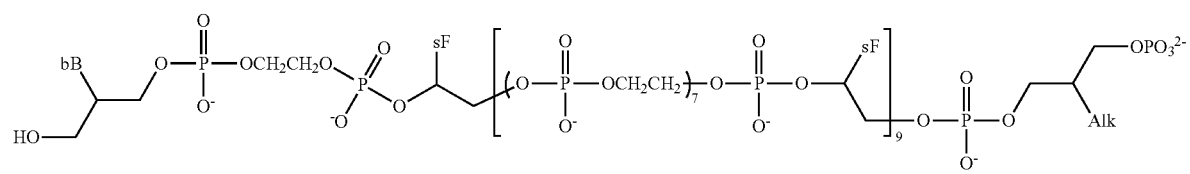

wherein:
Hex has the following structure:
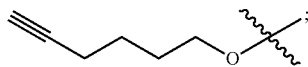
bB has the following structure:
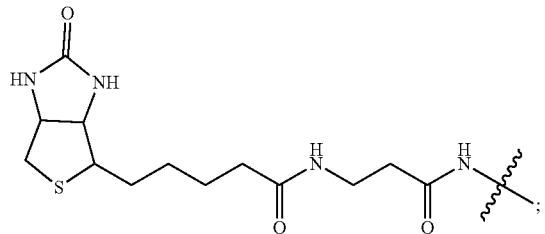
sF has the following structure:
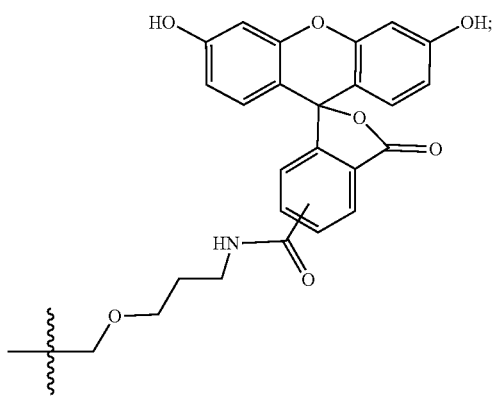
Alk has the following structure:
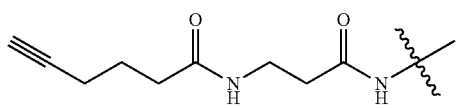 [SMILES: *NC(=O)CCNC(=O)CCCC#C]
and
F has the following structure:
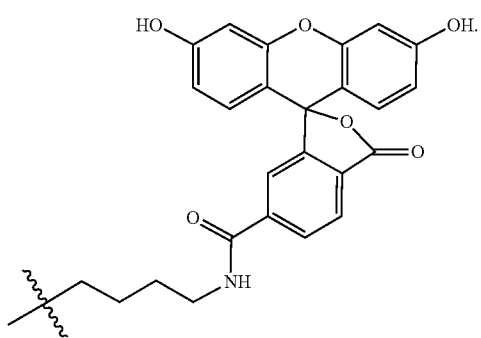 [SMILES: *CCCCNC(=O)c1ccc2c(c1)C1(OC2=O)c2ccc(O)cc2Oc2cc(O)ccc21]
3. The compound of claim 1, wherein M, at each occurrence, independently has one of the following structures:
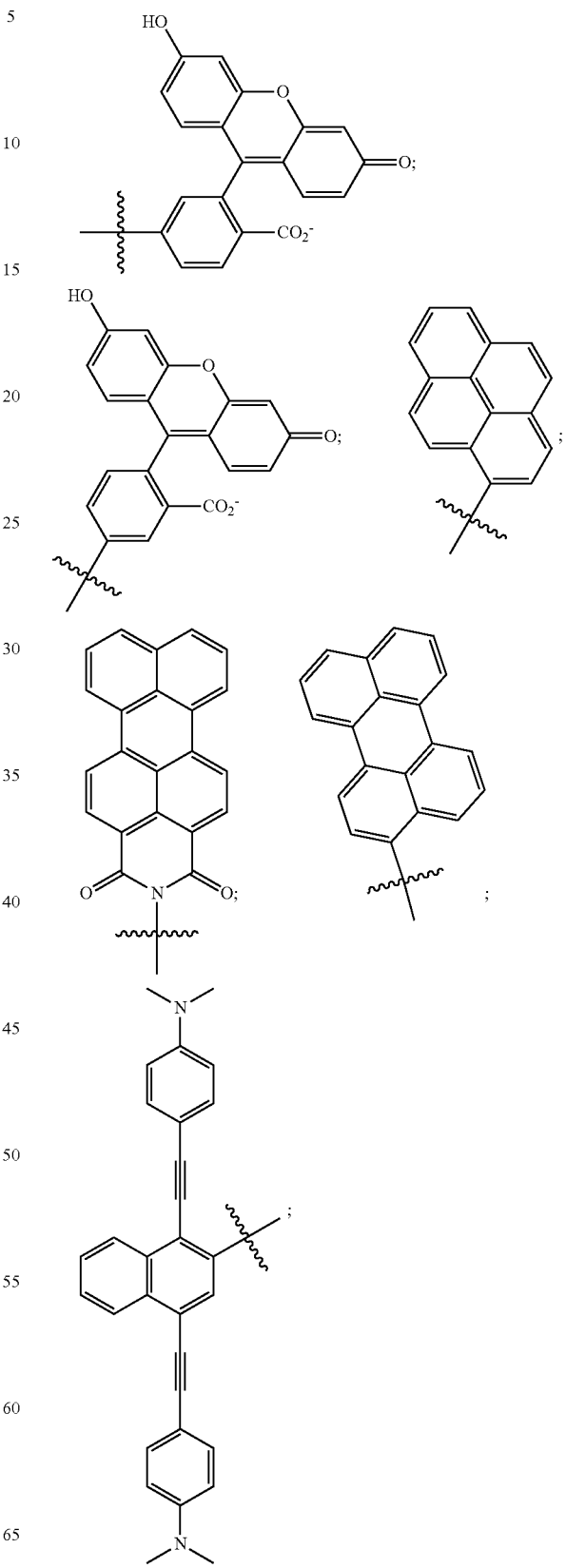

-continued

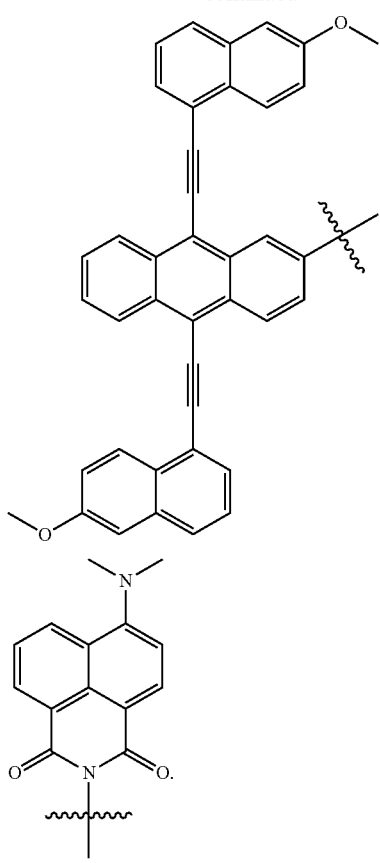

or

4. The compound of claim 1, wherein $L^4$ is alkylene.

5. The compound of claim 1, wherein $L^3$ is, at each occurrence, independently an amino acid or peptide linker.

6. The compound of claim 1, wherein $L^3$ is, at each occurrence, independently a linker comprising one or more charged moieties.

7. The compound of claim 1, wherein $R^1$ is H.

8. The compound of claim 1, wherein $A^1$, $A^2$ and $A^3$ are each independently OH or $-OP(=R_a)(R_b)R_c$.

9. A composition comprising the compound of claim 1 and one or more analyte molecules.

10. A method of staining a sample, comprising adding to said sample the compound of claim 1 in an amount sufficient to produce an optical response when said sample is illuminated at an appropriate wavelength.

11. A method for preparing the compound of structure (III) of claim 1, the method comprising:

reacting a second and third compound of structure (I):

$$(A^1\underset{L^3}{\overset{M\sim L^1}{\diagdown}}\underset{R^1}{\overset{}{C}}\underset{}{\overset{L^2}{\diagdown}}A^2)_x \quad (I)$$

with a fourth compound of structure (II):

$$(B^1)_y\text{—}L^4\text{—}(B^2)_z, \quad (II)$$

wherein:

$A^1$ and $A^2$ are each independently, alkyne, OH, $-OP(=R_a)(R_b)R_c$, Q, or a moiety comprising a first functional group having complementary reactivity to $B^1$, $B^2$ or both, provided at least one of $A^1$ and $A^2$ is a moiety comprising a first functional group having complementary reactivity to $B^1$, $B^2$ or both, wherein: $R_a$ is O; $R_b$ is $O^-$ or $OR_d$; $R_c$ is $O^-$, $OR_d$, or $OL'$; and $R_d$ is a counter ion;

$B^1$ and $B^2$ are each independently a second functional group having complementary reactivity to the first functional group;

M is, at each occurrence, independently a fluorescent or colored dye moiety or Q, provided at least one occurrence of M is a fluorescent or colored dye moiety;

$R^1$ is, at each occurrence, independently H, alkyl or alkoxy;

Q is, at each occurrence, independently a moiety having one of the following structures:

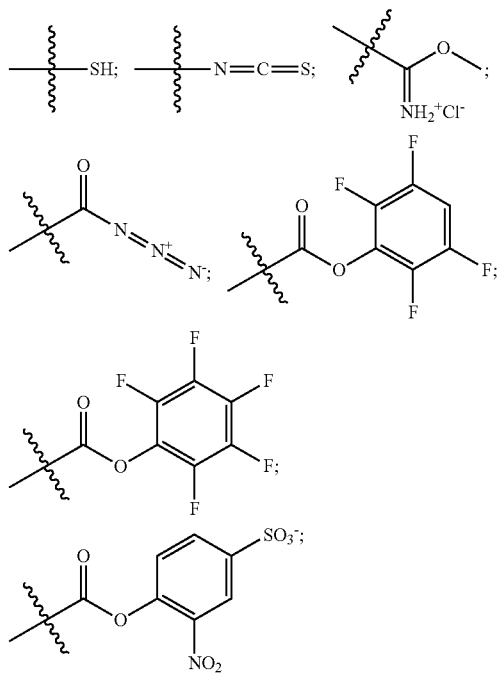

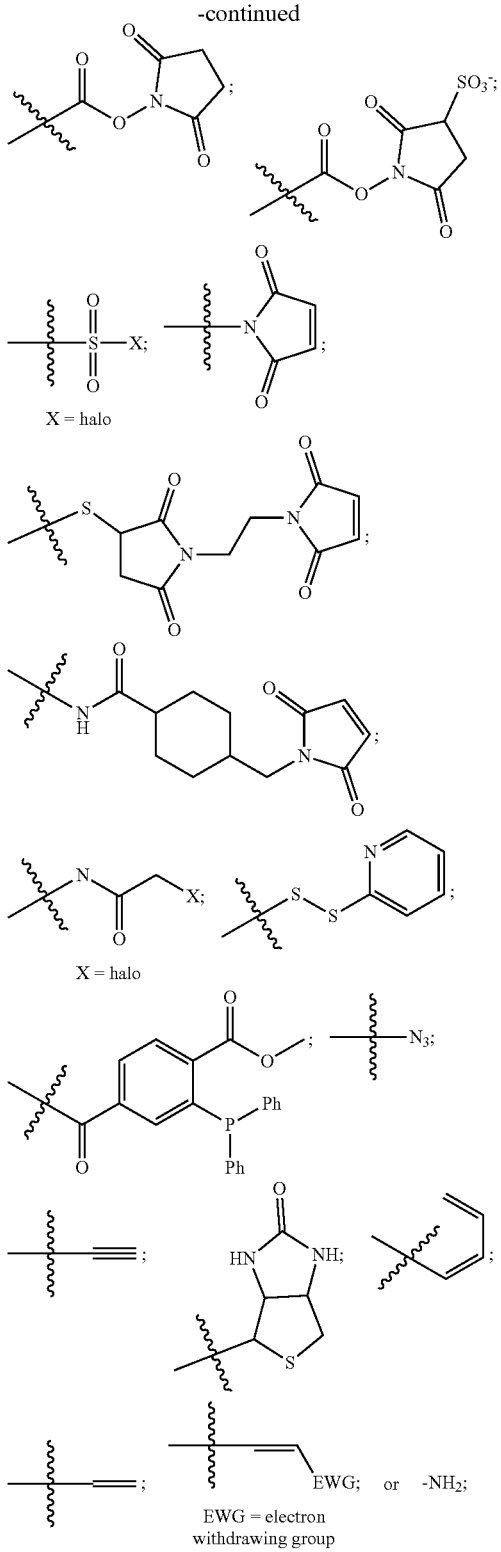

L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (I);

$L^1$ and $L^2$ are, at each occurrence, independently optional bivalent linker moieties;

$L^3$, at each occurrence, independently has the following structure:

$$\left(\!\!\left(O-\underset{R^4}{\overset{R^5}{\underset{|}{P}}}-O\right)\!\!\!L^5\right)_{m^1}\!\!\!\left(O-\underset{R^4}{\overset{R^5}{\underset{|}{P}}}-O\right)_{x^1}\!\!\!,$$

wherein:
$R^4$ is, at each occurrence, independently OH, SH, O⁻, S⁻, $OR_d$ or $SR_d$;
$R^5$ is, at each occurrence, independently oxo, thioxo or absent; and
$m^1$ and $x^1$ are, at each occurrence, independently an integer from 0 to 10;
$L^5$ is an alkylene, alkenylene, alkynylene, heteroalkylene, heteroalkenylene, heteroalkynylene, carbocyclic or heterocyclic linker;
$L^4$ is an optional multivalent linker moiety; and
x, y and z are independently an integer of 1 or greater,
thereby: i) forming a first bond between the second compound of structure (I) and the fourth compound of structure (II) by reaction of $B^1$ with the first functional group of the second compound of structure (I); and ii) forming a second bond between the third compound of structure (I) and the fourth compound of structure (II) by reaction of $B^2$ with the first functional group of the third compound of structure (I).

12. The method of claim 11, wherein $A^1$, $A^2$ are each independently a nucleophilic functional group, wherein the nucleophilic functional group is amino, alkylamino, sulfhydryl or hydroxyl.

13. The method of claim 11, wherein $B^1$ and $B^2$ are each independently an electrophilic functional group, wherein the electrophilic functional group is an acid halide, N-hydroxysuccinimide ester, isocyanate, isothiocyanate, epoxide, halide, tosylate, mesylate, triflate, maleimide, phosphate or alkene.

14. The method of claim 11, wherein $A^1$, $A^2$ are each independently an electrophilic functional group, wherein the electrophilic functional group is an N-hydroxysuccinimide ester, phenolate ester, halide, tosylate, mesylate, phosphate or triflate.

15. The method of claim 11, wherein $B^1$ and $B^2$ are each independently nucleophilic functional group, wherein the nucleophilic functional group is amino, alkylamino, sulfhydryl or hydroxyl.

16. The method of claim 11, wherein $A^1$ and $A^2$ are each independently an alkyne and $B^1$ and $B^2$ are each independently an azide or $A^1$ and $A^2$ are each independently an azide and $B^1$ and $B^2$ are each independently an alkyne.

17. The method of claim 11, wherein $A^1$ and $A^2$ comprise an aryl halide, boronic acid, boronic ester, alkylstannane, arylstannane, amine, and each of $B^1$ and $B^2$ are alkene or alkyne functional groups, aryl halide or alkyl halide functional groups.

18. The method of claim 11, wherein $L^4$ is alkylene.

* * * * *